(12) United States Patent
Romanczyk, Jr. et al.

(10) Patent No.: US 7,115,656 B2
(45) Date of Patent: *Oct. 3, 2006

(54) COMPOSITIONS FOR, AND METHODS OF, ANTI-PLATELET THERAPY

(75) Inventors: Leo J. Romanczyk, Jr., Hackettstown, NJ (US); Harold H. Schmitz, Bethesda, MD (US)

(73) Assignee: Mars, Incorporated, McLean, VA (US)

( * ) Notice: Subject to any disclaimer, the term of this patent is extended or adjusted under 35 U.S.C. 154(b) by 22 days.

This patent is subject to a terminal disclaimer.

(21) Appl. No.: 10/780,298

(22) Filed: Feb. 17, 2004

(65) Prior Publication Data

US 2004/0228936 A1 Nov. 18, 2004

Related U.S. Application Data

(63) Continuation of application No. 09/459,171, filed on Dec. 10, 1999, now Pat. No. 6,747,059, which is a continuation-in-part of application No. 08/831,245, filed on Apr. 2, 1997, now Pat. No. 6,297,273, which is a continuation-in-part of application No. 08/631,661, filed on Apr. 2, 1996, now abandoned.

(51) Int. Cl.
*A61K 31/352* (2006.01)
(52) U.S. Cl. .................................... 514/456
(58) Field of Classification Search ............... 549/400, 549/415; 514/456
See application file for complete search history.

(56) References Cited

U.S. PATENT DOCUMENTS 5,720,956 A 2/1998 Rohdewald ............... 424/770

FOREIGN PATENT DOCUMENTS

JP 02184626 7/1990

OTHER PUBLICATIONS

Chang, Wen-Chang and Hsu, Feng-Lin, *Inhibition of Platelet Aggregation and Arachidonate Metabolism in Platelets by Procyanidins, Prostaglandins Leukotrienes and Essential Fatty Acids*, vol. 38, pp. 181-188 (1989).

Polette, A., et al., *N-3 Fatty Acid-induced Lipid Peroxidation in Human Platelets is Prevented by Catechins, Thromb. Haemost.*, vol. 75, No. 6, pp. 945-949 (1996).

Kelly, Collete, et al., *Modulation of Human Platelet Function by Food Flavonoids, Biochemical Society Transactions* 24:197S (1996).

Uchida, Shinji, et al., *Inhibitory Effects of Condensed Tannins on Angiotensin Converting Enzyme, Japan. J. Pharmacol.* 43:242-246 (1987).

Chang, W.C., et al., *Inhibition of Platelet Activation and Endothelial Cell Injury by Flavan-3-ol and Saikosaponin Compounds, Prostaglandins Leukotrienes and Essential Fatty Acids* (1991).

Ferrandiz, M.L., et al., *Inhibition of Sheep Platelet Arachiodonate Metabolism by Flavonoids form Spanish and Indian Medicinal Herbs, Pharmazie 45*, pp. 206-208 (1990).

Rohrbach, Michael S., et al., *Structural Deeterminants of the Platelet Agonist Activity of Cotton Bract Condensed Tannin, Environmental Research* 52:199-209 (1990).

Pace-Asciak, Cecil R., et al., *The Red Wine Phenolics trans-resveratrol and Quercetin Block Human Platelet Aggregationand Eicosanoid Synthesis: Implications for Protection Against Coronary Heart Disease, Clinica Chimica Acta* 235:207-219 (1995).

Pace-Asciak, Cecil R., et al., *Wines and Grape Juices as Modulators of Platelet Aggregation in Healthy Human Subjects, Clinica Chimica Acta* 246:163-182 (1996).

Van Acher et al., *Flavonoids as Scavengers of Nitric Oxide Radical, Biochem. Biophysical Res. Comm.*, 214: 755-759 (1995).

Primary Examiner—Taofiq A. Solola
(74) Attorney, Agent, or Firm—Nada Jain, P.C.

(57) ABSTRACT

This invention discloses methods of anti-platelet therapy or prophylaxis comprising administering to a subject in need thereof a composition comprising an effective amount of a procyanidin oligomer or a derivative thereof.

47 Claims, 46 Drawing Sheets

Summary of the current purification protocol

Chart showing the major contributing factors in the progression of Coronary Heart Disease (CHD) and how the activity of cocoa procyanidins contributes to the prevention of the progression of the disease state

FIG. 2C

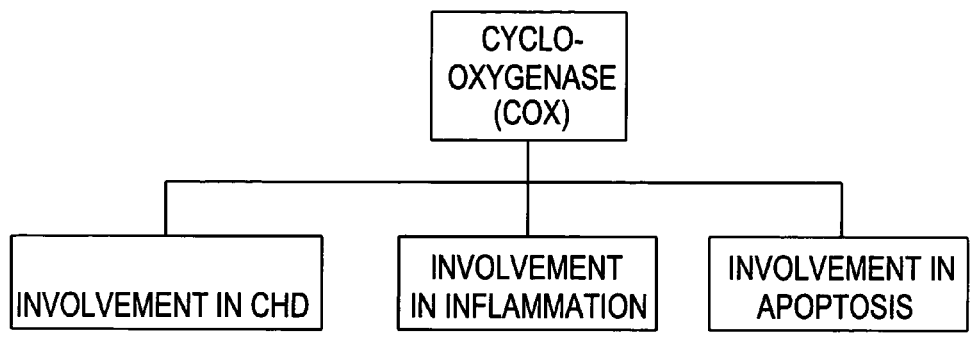

COX-1 is essential in the arachidonic acid pathway which results in the production of thromboxane.

→ thromboxane and prostaglandins which promote platelet aggregation and vasoconstriction → resulting in progression of atherosclerosis.

COX-1 is an essential enzyme in the inflammatory pathway, the penultimate products of which (the prostaglandins) are largely responsible for the inflammatory pathway, the results of which contribute to a variety of diseases including:

→ bowel disease, arthritis, edema, gingivitis/peridontitis, etc.

COX-2 producing cells lines show enhanced expression of genes known to be involved in apoptosis:

→ potential putative mechanism of killing tumor cells.

The cocoa procyanidins inhibit the production of cyclo-oxygenase, thereby blocking the arachidonic acid pathway, which is responsible for the inflammatory response and the vasoconstrictive and platelet aggregating responses which contribute to the disease progression of CHD.

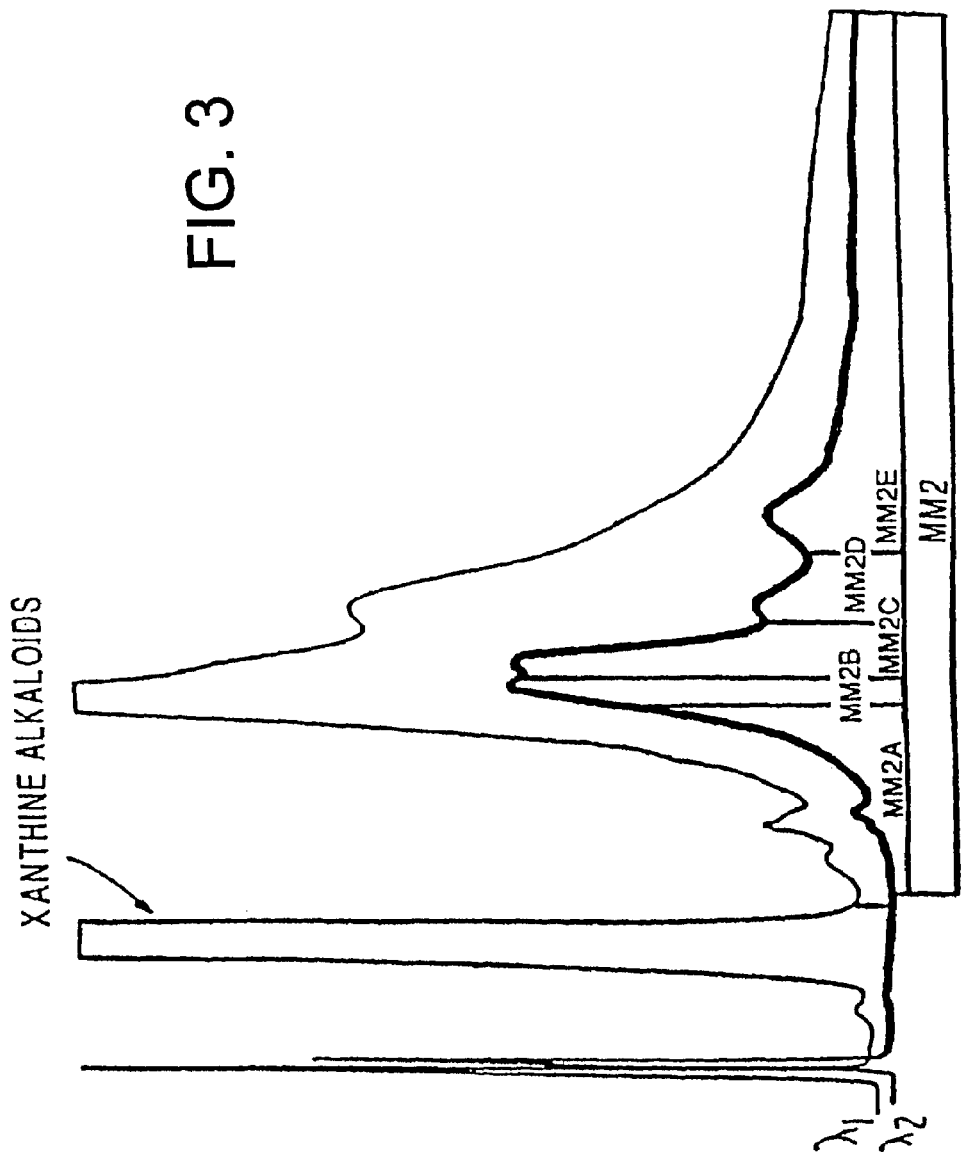

EFFECT OF COCOA PROCYANIDIN FRACTION A ON BLOOD PRESSURE

BP decreased by 21.43% within 1min
BP back to normal value after 1.5 min

EFFECT OF COCOA PROCYANIDIN FRACTION C ON BLOOD PRESSURE

BP decreased by 50.5% within 1 min
BP back to normal value after 5 min

EFFECT OF COCOA PROCYANIDIN FRACTIONS ON ARTERIAL BLOOD PRESSURE IN ANESTHESIZED GUINEA PIGS

EFFECT OF L-NMMA ON THE ALTERATIONS OF ARTERIAL BLOOD PRESSURE IN ANESTHESIZED GUINEA PIGS INDUCED BY COCOA PROCYANIDIN FRACTION C

EFFECT OF BRADYKININ ON NO PRODUCTION BY HUVEC

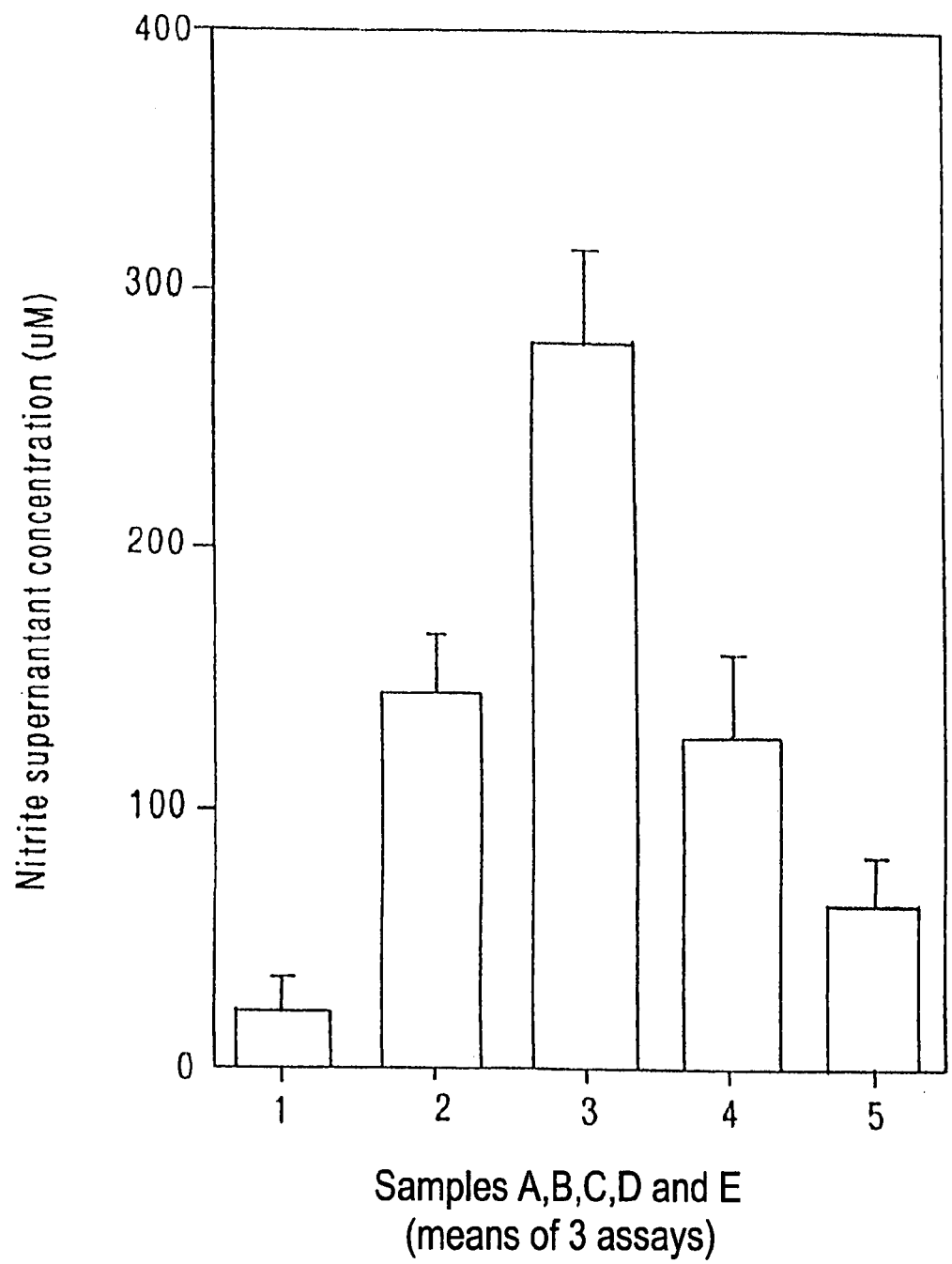

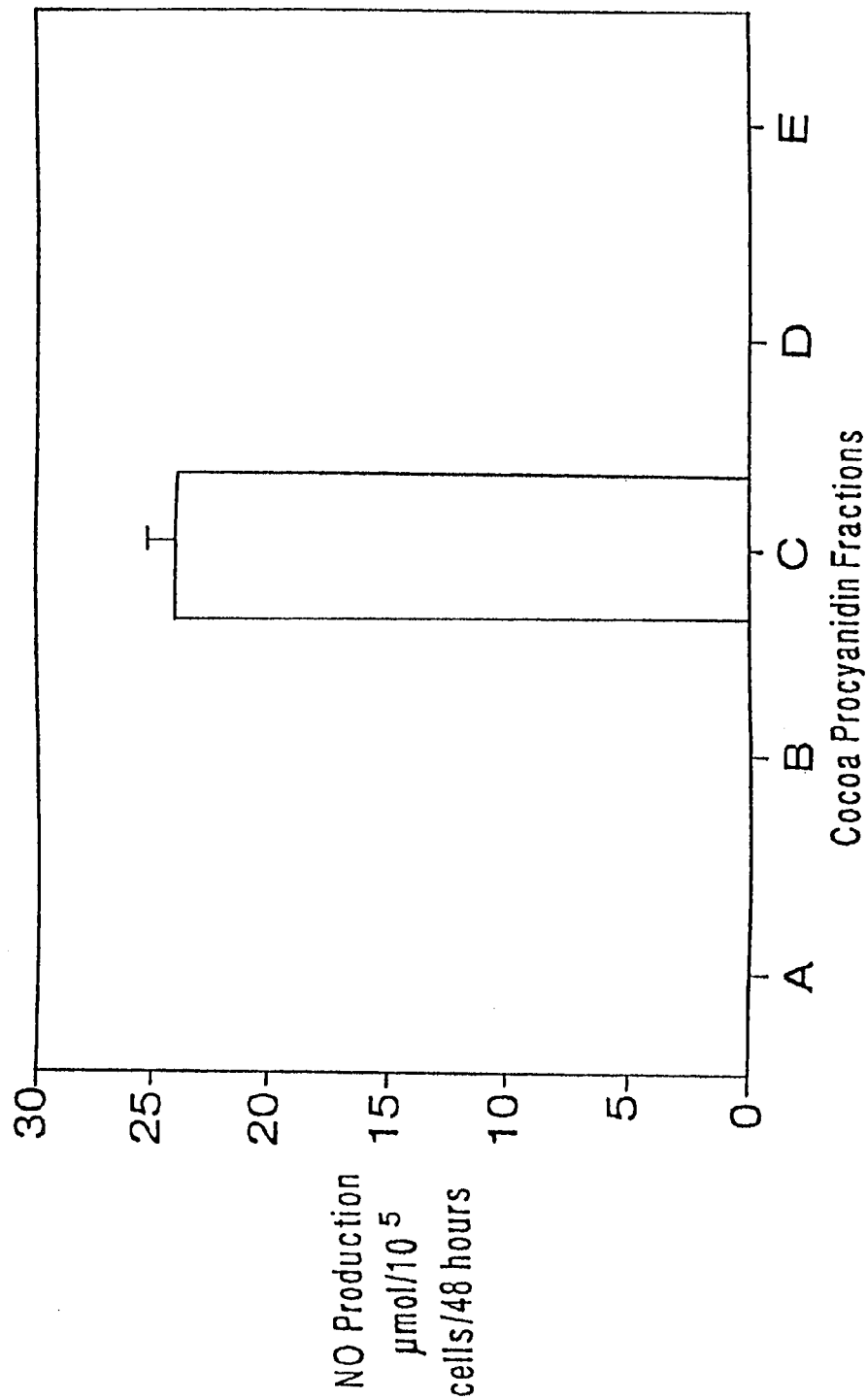

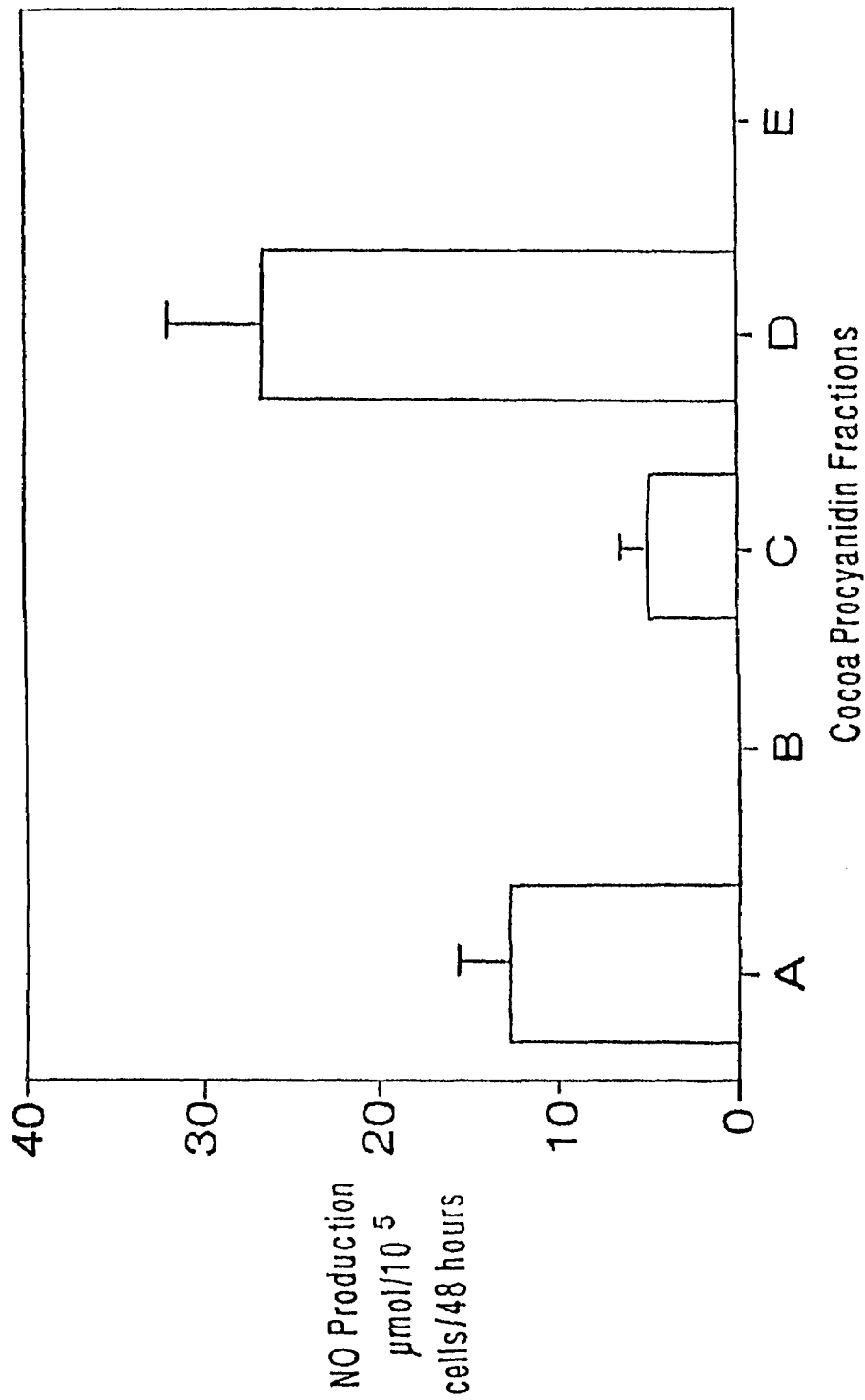

DEGREE OF POLYMERIZATION (SAMPLE #)
(*) WITH THE EXCEPTION OF SAMPLE S11 EXPRESSED AS mg/ml (*) WITH THE EXEPTION OF SAMPLE S11

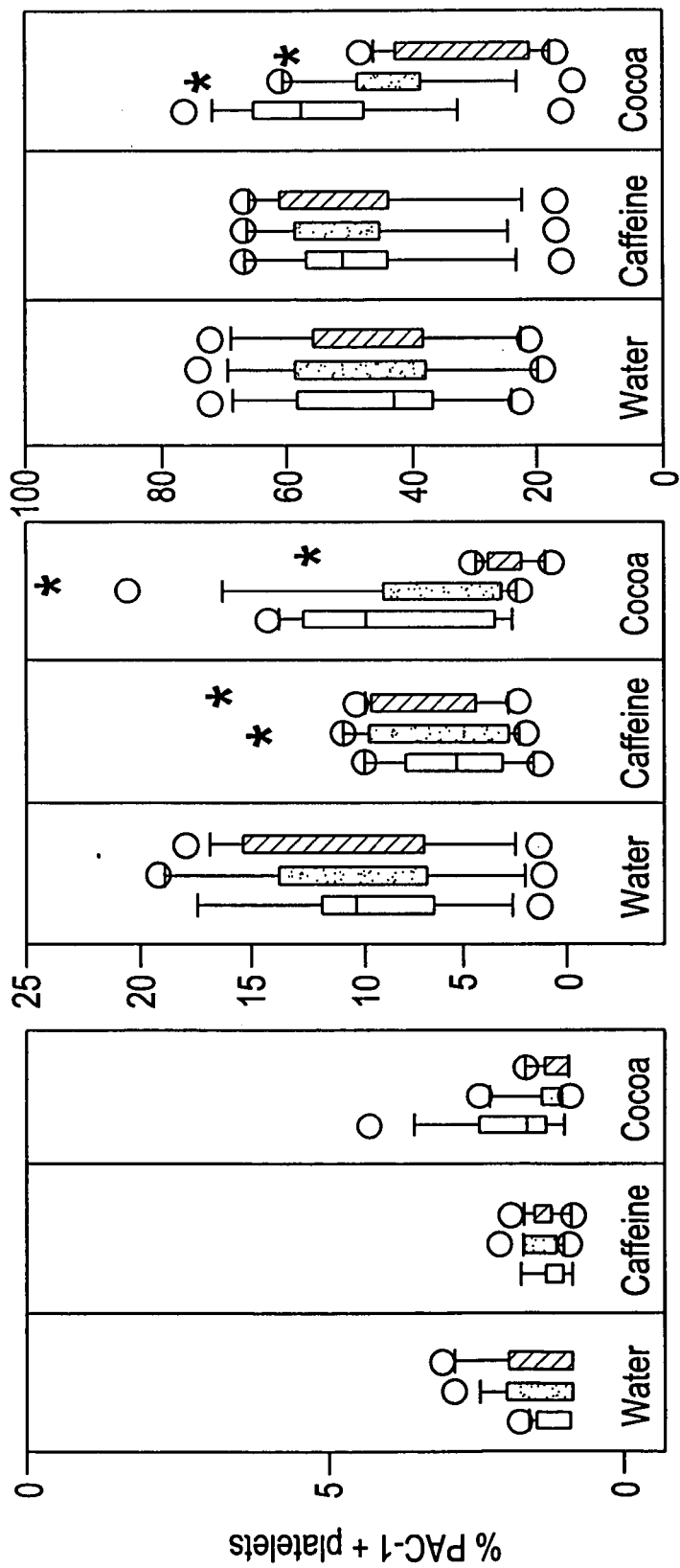

COMPOSITIONS FOR, AND METHODS OF, ANTI-PLATELET THERAPY

REFERENCE TO RELATED APPLICATIONS

This application is a continuation application of U.S. Ser. No. 09/459,171, filed Dec. 10, 1999, (now U.S. Pat. No. 6,747,059), which is a continuation-in-part application of U.S. Ser. No. 08/831,245 filed Apr. 2, 1997, now U.S. Pat. No. 6,297,273, which is a continuation-in-part application of abandoned U.S. Ser. No. 08/631,661 filed Apr. 2, 1996 now abandoned. The application Ser. Nos. 09/459,171 and 08/631,661 are hereby incorporated herein by reference.

FIELD OF THE INVENTION

This invention relates to medical and nutritional uses of extracts and products containing cocoa polyphenols including cocoa procyanidins.

BACKGROUND OF THE INVENTION

Polyphenols are an incredibly diverse group of compounds (Ferriera et al., 'Diversity of Structure and Function in Oligomeric Flavanoids, Tetrahedron, 48:10, 1743–1803, 1992). They widely occur in a variety of plants, some of which enter into the food chain. In some cases they represent an important class of compounds for the human diet. Although some of the polyphenols are considered to be non-nutritive, interest in these compounds has arisen because of their possible beneficial effects on health.

For instance, quercetin (a flavonoid) has been shown to possess anticarcinogenic activity in experimental animal studies (Deshner et al., 'Quercertin and Rutin as Inhibitors of Azoxymethanol-induced Colonic Neoplasia', Carcinogenesis, 7:1193–1196, 1991: and Kato et al., 'Inhibition of 12-O-tetradecanoylphorbol-13-acetate Induced Tumor Promotion and Ornithine Decarboxylase Activity by Quercitin: Possible Involvement of lipoxygenase Inhibition', Carcinogenesis, 4, 1301–1305 1983). (+)-catechin and (−)-epicatechin (flavan-3-ols) have been shown in inhibit Leukemia virus reverse transcriptase activity (Chu et al., Inhibitory Effects of Flavonoids on Maloney Murine Leukemia Virus Reverse Transcriptase Activity, J. of Natural Products, 55:2, 179–183, 1992). Nobotanin (an oligomeric hydrolyzable tannin) has also been shown to possess anti-tumor activity (Okuda et al., 'Molecular Structures and Pharmacological Activities of Polyphenols—Oligomeric Hydrolyzable Tannins and Others'—Presented at the XVIth International Conference of the Groupe Polyphenols, Lisbon, Portugal, Jul. 13–16, 1992). Statistical reports have also shown that stomach cancer mortality is significantly lower in the tea producing districts of Japan. Epigallocatechin gallate has been reported to be the pharmacologically active material in green tea that inhibits mouse skin tumors (Okuda et al, 'Molecular Structures and Pharmacological Activities of Polyphenols—Oligomeric Hydrolyzable Tannins and others. Presented at the XVIth International Conference of the Groupe polyphenols, Lisbon, Portugal, 1992). Osakabe et al. (JP 7274894 "Food and Drink For Preventing Gastric Ulcers—Contains Antioxidation Substance Extracted from Cacao Beans using Hot Water or Ethanol" October 1995; JP 7213251 "Method on Manufacturing an Antioxidation Substance and a Health Food or Drink Item Containing an Antioxidation Substance" August 1995) have reported that the antioxidant properties of cocoa bean extract, thought to contain epicatechin and analogous compounds, are responsible for inhibiting formation of gastric ulcers in rats. Ellagic acid has also been shown to possess anticarcinogen activity in various animal tumor models (Boukharta et al., Efficacy of Ellagitannins and Ellagic Acid as Cancer Chemopreventive Agents—Presented at the XVIth International Conference of the Groupe Polyphenols, Lisbon, Portugal, Jul. 13–16, 1992). Lastly, proanthocyanidin oligomers have been reported by the Kikkoman Corporation for use as antimutagens ('Antimutagenic Agent Containing Proanthocyanidin Oligomer Preferably Having Flavan-3-ol-diol Structure' JP 04190774A, Jul. 7, 1992). Indeed, the area of phenolic compounds in foods and their modulation of tumor development in experimental animal models has been recently presented to the 202nd National Meeting of The American Chemical Society (Phenolic Compounds in Foods and Their Effects on Health II. Antioxidants & Cancer Prevention, Huang, M.-T., Ho, C.-T., and Lee, C. Y. editors, ACS Symposium Series 507, Am. Chem. Soc., Washington, D.C. 1992).

SUMMARY OF THE INVENTION

It has been surprisingly discovered that cocoa extract, and compounds therefrom, have anti-tumor, anti-cancer or anti-neoplastic activity or, is an antioxidant composition or, inhibits DNA topoisomerase II enzyme activity or, is an antimicrobial or, is a cyclo-oxygenase and/or lipoxygenase modulator or, is a NO or NO-synthase modulator or, is a blood or in vivo glucose modulator.

Accordingly, the present invention provides a substantially pure cocoa extract and compounds therefrom. The extract or compounds preferably comprises polyphenol(s) such as polyphenol(s) enriched with cocoa procyanidin(s), such as polyphenols of at least one cocoa procyanidin selected from (−) epicatechin, (+) catechin, procyanidin B-2, procyanidin oligomers 2 through 12, preferably 2 through 4 or 4 through 12, more preferably 3 through 12, and most preferably 5 through 12, procyanidin B-5, procyanidin A-2 and procyanidin C-1.

The present invention also provides an anti-tumor, anti-cancer or antineoplastic or antioxidant or DNA topoisomerase II inhibitor, or antimicrobial, or cyclo-oxygenase and/or lipoxygenase modulator, or an NO or NO-synthase modulator, or blood or in vivo glucose modulator composition comprising a substantially pure cocoa extract or compound therefrom or synthetic cocoa polyphenol(s) such as polyphenol(s) enriched with procyanidin(s) and a suitable carrier, e.g., a pharmaceutically, veterinary or food science acceptable carrier. The extract or compound therefrom preferably comprises cocoa procyanidin(s). The cocoa extract or compounds therefrom is preferably obtained by a process comprising reducing cocoa beans to powder, defatting the powder and, extracting and purifying active compound(s) from the powder.

The present invention further comprehends a method for treating a patient in need of treatment with an anti-tumor, anti-cancer, or antineoplastic agent or an antioxidant, or a DNA topoisomerase II inhibitor, or antimicrobial, or cyclo-oxygenase and/or lipoxygenase modulator, or an NO or NO-synthase modulator, or blood or in vivo glucose modulator comprising administering to the patient a composition comprising an effective quantity of a substantially pure cocoa extract or compound therefrom or synthetic cocoa polyphenol(s) or procyanidin(s) and a carrier, e.g., a pharmaceutically, veterinary or food science acceptable carrier. The cocoa extract or compound therefrom can be cocoa procyanidin(s); and, is preferably obtained by reducing cocoa beans to powder, defatting the powder and, extracting and purifying active compound(s) from the powder.

Anti-cancer, anti-tumor or antineoplastic or, antioxidant, DNA topoisomerase II enzyme inhibiting, antimicrobial, cyclo-oxygenase and/or lipoxygenase modulator NO— or NO-synthase and blood or in vivo glucose modulating activities, or compositions containing the inventive cocoa polyphenols or procyanidins can be prepared in accordance with standard techniques well known to those skilled in the pharmaceutical or food science or veterinary art(s).

Such compositions can be administered to a subject or patient in need of such administration in dosages and by techniques well known to those skilled in the medical, nutritional or veterinary arts taking into consideration such factors as the age, sex, weight, and condition of the particular subject or patient, and the route of administration. The compositions can be co-administered or sequentially administered with other antineoplastic, anti-tumor or anti-cancer agents, antioxidants, DNA topoisomerase II enzyme inhibiting agents, or cyclo-oxygenase and/or lipoxygenase, blood or in vivo glucose or NO or NO-synthase modulating agents and/or with agents which reduce or alleviate ill effects of antineoplastic, anti-tumor, anti-cancer agents, antioxidants, DNA topoisomerase II enzyme inhibiting agents, cyclo-oxygenase and/or lipoxygenase, blood or in vivo glucose or NO or NO-synthase modulating agents; again, taking into consideration such factors as the age, sex, weight, and condition of the particular subject or patient, and, the route of administration.

Further, the invention also comprehends a kit wherein the active cocoa extract is provided. The kit can include a separate container containing a suitable carrier, diluent or excipient. The kit can also include an additional anti-cancer, anti-tumor or antineoplastic agent, antioxidant, DNA topoisomerase II enzyme inhibitor or antimicrobial, or cyclo-oxygenase and/or lipoxygenase, NO or NO-synthase or blood or in vivo glucose modulating agent and/or an agent which reduces or alleviates ill effects of antineoplastic, anti-tumor or anti-cancer agents, antioxidant, DNA topoisomerase II enzyme inhibitor or antimicrobial, or cyclo-oxygenase and/or lipoxygenase, NO or NO-synthase or blood or in vivo glucose modulating agents for co- or sequential-administration. The additional agent(s) can be provided in separate container(s) or in admixture with the active cocoa extract. Additionally, the kit can include instructions for mixing or combining ingredients and/or administration.

A cocoa polyphenol-containing composition, which is useful for modulating inflammatory pathways in a mammal, for maintaining vascular health, and as an antibacterial treatment, comprising a cocoa ingredient containing the cocoa polyphenols and optionally a carrier, diluent, or excepient. The composition is useful as a food, a dietary supplement, or a pharmaceutical. The food or dietary supplement can be a beverage or an elixir (i.e., ethanol extract), or a powder.

The cocoa polyphenols can be from ingredients or prepared synthetically. They can be present in cocoa ingredients. They can be extracted from cocoa beans, cocoa nibs, or cocoa ingredients such as chocolate liquor, partially defatted cocoa solids, and/or fully defatted cocoa solids. The cocoa procyanidins are monomers and/or oligomers of epicatechin and catechin. The oligomers include dimers through octadecamers.

When extracted from cocoa beans, cocoa nibs, cocoa nib fractions, chocolate liquor, partially defatted cocoa solids, and/or fully defatted cocoa solids, a solvent which dissolves the cocoa polyphenols is used. Suitable solvents include water, methanol, ethanol, acetone, ethyl acetate, or mixtures thereof. Preferred solvents are mixtures of water and methanol or acetone. When water is used as the solvent, it is preferable if it is slightly acidified. In some cases the extract is purified, for example by removal of the caffeine and/or theobromine, and then further purified by gel permeation chromatography and/or high pressure liquid chromatography. During the high pressure liquid chromatography, the extract can be fractionated into monomeric and oligomeric fractions containing at least 50% by weight of the monomers or specific oligomers. When the fractions contain the monomers and lower oligomers (up to and including the tetramer), the fractions contain about 90 to 95% by weight of the particular oligomeric fraction.

Use of the above composition provides a method for modulating a mammalian inflammatory pathway by inhibiting COX activity, for modulating the production of eicosanoids and endothelin, for preventing diseases (such as bowel disease edema, arthritis, gingivitis or peridontitis) caused by chronic inflammation, for preventing vascular disease, for enhancing nitric oxide synthesis, for inhibiting LOX activity, for reducing vasoconstriction, for reducing platelet aggregation, for inhibiting monocyte adhesion, for inhibiting vascular smooth muscle proliferation associated with vascular disease, for reducing thrombosis, for reducing blood pressure, and for modulating oxidative stress to prevent associated inflammatory disorders and vascular diseases. Modulation of oxidative stress, for example, by preventing (LDL) oxidation, is another method of which the above composition can modulate mammalian inflammatory pathways and vascular function and disease.

The products comprising the cocoa polyphenol-containing composition are preferably in forms suitable for oral delivery, such as tablets, capsules, pills, concentrates, powders, liquids, or food ingredients, food additives or dietary supplements. The tablet may comprise an effective amount of the cocoa polyphenol-containing composition and optionally a carrier, such as sorbitol, lactose, cellulose, or dicalcium phosphate. The capsule may comprise a gelatin capsule containing a predetermined dosage of the cocoa polyphenol-containing composition. The oral delivery product may also comprise a dietary supplement nutrient such as dicalcium phosphate, magnesium stearate, calcium nitrate, vitamins, and minerals.

The compositions comprising the cocoa extract, sub-fractions thereof or mixtures thereof further comprise a liquid or a solid carrier suitable for use in foods, food supplements or pharmaceuticals. Such products include food and beverage products, in addition to capsule, tablet and pressed powder compositions. For the purposes of this application, the following definitions will enable a clearer understanding of what is disclosed and claimed:

As used herein a "food" is a material consisting essentially of protein, carbohydrate and/or fat, which is used in the body of an organism to sustain growth, repair and vital processes and to furnish energy. Foods may also contain supplementary substances such as minerals, vitamins and condiments. See Merriam-Webster's Collegiate Dictionary, 10th Edition, 1993.

As used herein, a "pharmaceutical" is a medicinal drug. See Merriam-Webster's Collegiate Dictionary, 10th Edition, 1993.

As used herein, a "Food Supplement" is a product (other than tobacco) that is intended to supplement the diet that bears or contains the one or more of the following dietary ingredients: a vitamin, a mineral, an herb or other botanical, an amino acid, a dietary substance for use by man to supplement the diet by increasing the total daily intake, or a concentrate, metabolite, constituent, extract or combination of these ingredients. See Merriam-Webster's Collegiate Dictionary, 10th Edition, 1993. As used on food labels, 'supplement' means that nutrients have been added in amounts greater than 50% above the U.S. RDA ("Understanding Normal and Clinical Nutrition, Third Edition", Eds. Whitney, Cataldo and Rolfes, p. 525).

The compositions comprising the cocoa extracts, subfractions thereof, or mixtures thereof, are usefull for inhibiting COX activity, inhibiting LOX activity, enhancing nitric oxide production, reducing vasoconstriction, reducing platelet aggregation, inhibiting monocyte adhesion, inhibiting excessive proliferation of vascular smooth muscle, reducing thrombosis, reducing blood pressure and modulating the production of eicosanoids and endothelin. Diseases, such as bowel disease, arthritis, edema, gingivitis and peridontitis, which are caused by chronic inflammation, are also prevented.

BRIEF DESCRIPTION OF THE DRAWINGS

The following Detailed Description will be better understood by reference to the accompanying drawings wherein:

FIG. 2*a*–*c* is a schematic diagram showing the relationship between the biological activity of the cocoa polyphenols and their utility in the prevention of coronary heart disease.

FIG. 3 shows a representative gel permeation chromatogram from the fractionation of crude cocoa procyanidins.

FIG. 12 shows the effect of cocoa procyanidin fractions on macrophage NO production by HUVEC.

FIG. 13 shows the effect of cocoa procyanidin fractions on macrophage NO production.

FIG. 14 shows the effect of cocoa procyanidin fractions on macrophage NO production.

FIG. 21A–C shows the effect of cocoa beverage consumption on platelet surface expression of activated GPIIb-IIIa with and without stimulation with weak agonists. Platelet activation marker expression is presented as Tukey box plots at times zero (white boxes), 2 hours (dotted boxes) and 6 hours (cross-hatched boxes) post consumption of water, a caffeine-containing control beverage (caffeine) or a cocoa beverage (cocoa). (A)—percentage of platelets expressing activated GPIIb-IIIa (PAC1+platelets) without stimulation;

(B)—after stimulation with epinephrine (20 μM); or (C)—with ADP (20 μM). Activated GPIIb-IIIa is expressed on the surface of activated platelets. Each box shows the 25–75$^{th}$ percentile, the horizontal bar in the box shows the median. The lines outside of the box show the 10$^{th}$ and 90$^{th}$ percentile. Asterisks indicate P<0.05 between zero time and 6 hour time points of each respective data set (repeated measure ANOVA on ranks, Student-Newman-Keuls multiple comparison method, n=10 in each).

Figures 22A, 22B, 22C:
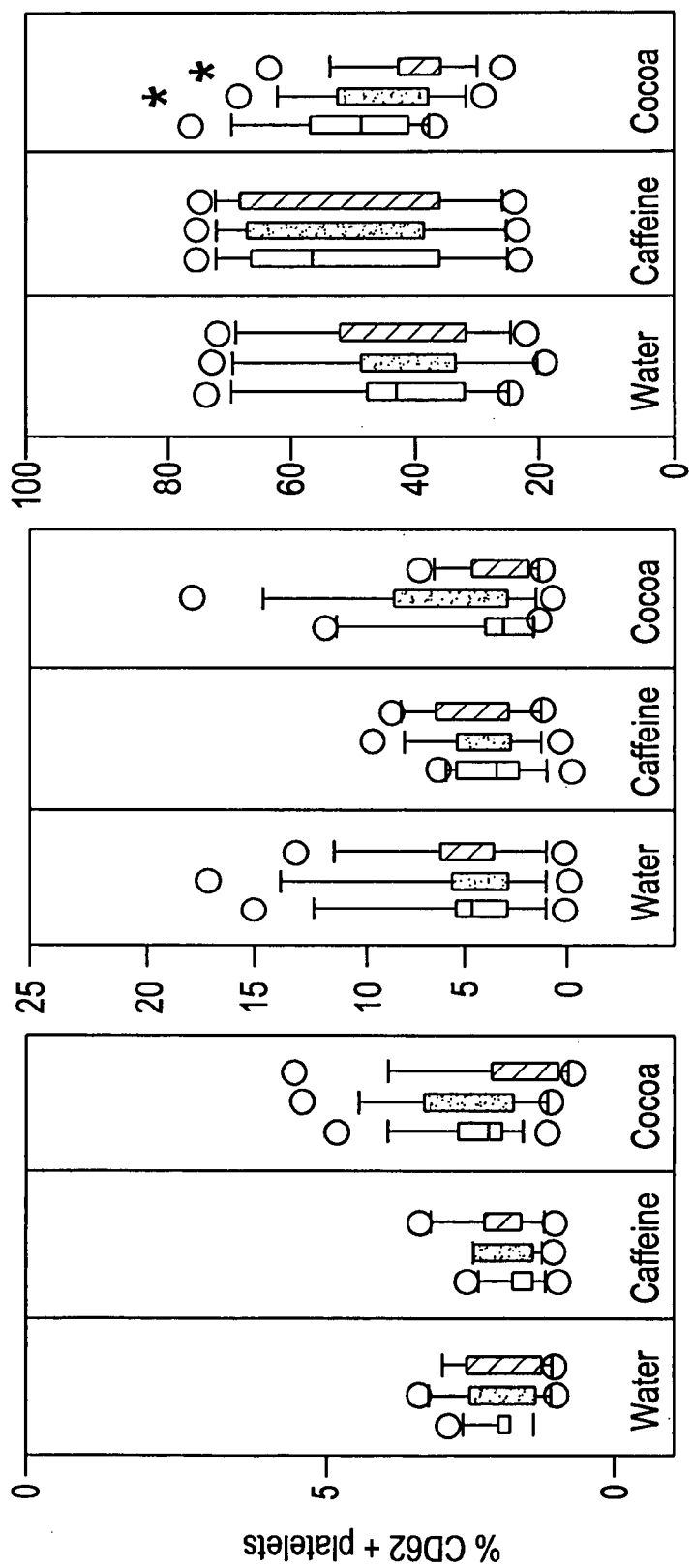

FIG. 22A–C shows the effect of cocoa beverage consumption on platelet surface expression of activated P-selectin with and without stimulation with weak agonists. Platelet activation marker expression presented as Tukey box plots at times zero (white boxes), 2 hours (dotted boxes) and 6 hours (cross-hatched boxes) post consumption of water, a caffeine-containing control beverage (caffeine) or a cocoa beverage (cocoa). (A)—percentage of platelets expressing P-selectin (CD62P+platelets) without stimulation; (B)—after stimulation with epinephrine (20 μM); or (C)—with ADP (20 μM). P-selectin is expressed on the surface of activated platelets. Each box shows the 25–75$^{th}$ percentile, the horizontal bar in the box shows the median. The lines outside of the box show the 10$^{th}$ and 90$^{th}$ percentile. Asterisks indicate P< 0.05 between zero time and 6 hour time points of each respective data set (repeated measure ANOVA on ranks, Student-Newman-Keuls multiple comparison method, n=10 in each).

DETAILED DESCRIPTION

Monomers comprising procyanidins have the structure:

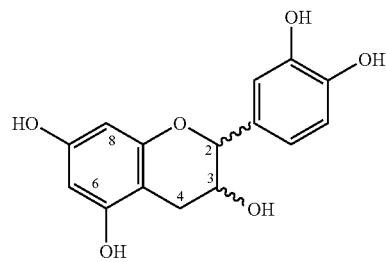

Procyanidins include those found in cocoa beans obtained from *Theobroma cacao* and various related cocoa species, as well as the genus *Herrania* and their inter- and intra-genetic crosses.

Monomers comprising procyanidins include (+)-catechin, (−)-epicatechin and their respective epimers (e.g. (−)-catechin and (+)-epicatechin).

Synthetic linear and/or branched oligomers having the following structures are illustrative of the cocoa procyanidins.

Linear oligomers where n is an integer from 0 to 16

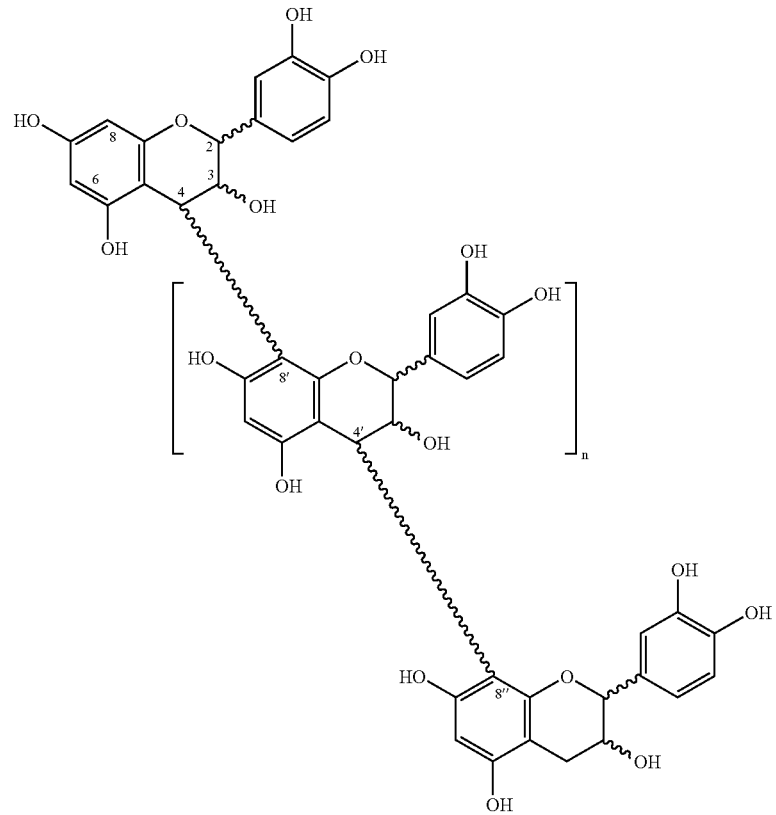

Branched oligoniers where A and B are independently oligomers from 1 to 15 which total 3–18 in final oligomer.

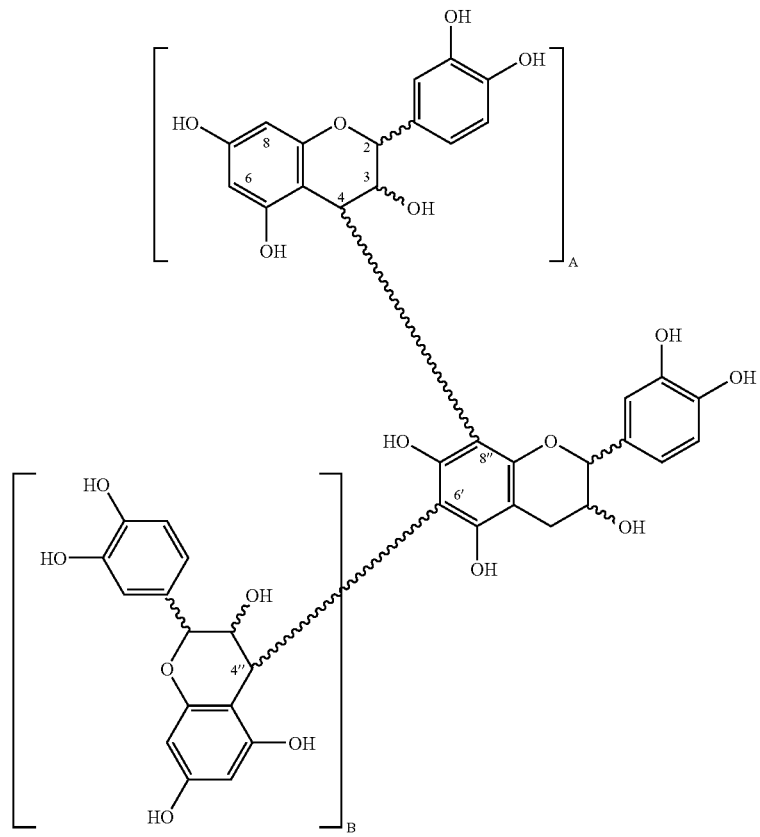

In the oligomers n is an integer from 2 through 18, preferably 3 through 12, more preferably 5 through 12, and most preferably 5. The oligomers have interflavan linkages of (4→6) and and/or (4→8). The oligomers may be represented by the structures above. For the linear oligomer, when x is 0, the oligomer is termed a "dimer"; when x is 1 the oligomer is termed a "trimer"; when x is 2, the oligomer is termed a "tetramer"; when x is 3, the oligomer is termed a "pentamer"; and similar recitations may be designated for oligomers having x up to and including 16 and higher, such that when x is 16, the oligomer is termed an "octadecamer." For the branched oligomer, when A or B is 1, the oligomer is termed a "trimer"; with similar recitations such as those described for the linear oligomers.

Derivatives of the synthetic cocoa polyphenols include the gallated monomers and oligomers (a method for the preparation of the dimer di-gallate is disclosed in U.S. Ser. No. 09/289,565 filed Apr. 9, 1999, (now U.S. Pat. No. 6,156,912), the disclosure of which is incorporated by referenc), the glycosylated monomers and oligomers, and mixtures thereof. Also included are metabolites of the monomers and oligomers, and including the sulphated, glucuronidated, and methylated forms. Further included are the enzyme cleavage products generated by colonic microflora metabolism or internal mammalian metabolism.

The cocoa extracts are generally prepared by reducing cocoa beans to cocoa powder, defatting the powder, extracting the cocoa polyphenols, and purifying the extract. The cocoa powder can be prepared by freeze-drying the cocoa beans and pulp, depulping and dehulling the freeze-dried cocoa beans, and grinding the dehulled beans. The cocoa polyphenols can be extracted from the powder by solvent extraction techniques. The cocoa extracts can be purified, e.g., to be substantially pure, for instance, by gel permeation chromatography or by preparative High Performance Liquid Chromatography (HPLC) techniques or by a combination of such techniques.

With reference to the extraction and purification of the cocoa extracts, it will be understood that any species of *Theobroma, Herrania* or inter- and intra-species crosses thereof may be employed. In this regard, reference is made to Schultes, Synopsis of *Herrania*," Journal of the Arnold Arboretum, Vol. XXXIX, pp 217 to 278, plus plates I to XVII (1985), Cuatrecases, "Cocoa and Its Allies, A Taxonomic Revision of the Genus *Theobroma*, " Bulletin of the United States National Museum, Vol. 35, page 6, pp. 379 to 613, plus plates 1 to 11 (Smithsonian Institution, 1964), and Addison, et al., 'Observations on the Species of the Genus *Theobroma* Which Occurs in the Amazon," Bol. Tehc. Inst. Agronomico de Nortes, 25(3)(1951). The cocoa procyanidins can be isolated from cocoa or from any species within the *Theobroma* and *Herrania* genera. Additionally, Table 4 lists the heretofore never reported concentrations of the cocoa procyanidins found in *Theobroina* and *Herrania* species and their inter- and intra-species crosses.

Figure 1:
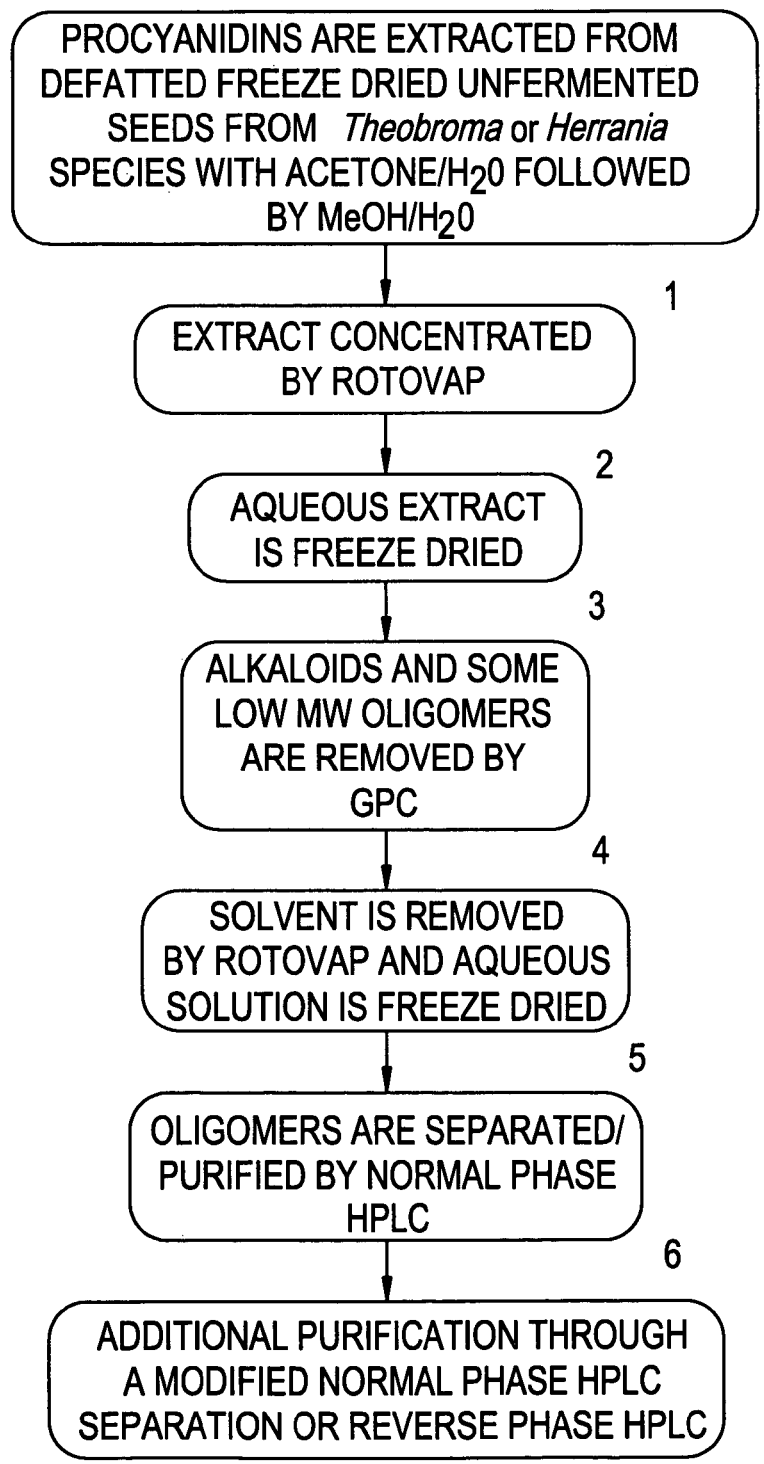
FIG. 1 shows a purification scheme for the isolation of procyanidins from cocoa.

An outline of the purification protocol utilized in the isolation of substantially pure cocoa procyanicins is shown in FIG. 1. The steps of the purification process are outlined in Examples 1–5. The skilled artisan would appreciate and envision modification in the purification scheme outlined in FIG. 1 to obtain the active compounds without departing from the spirit or scope thereof and without undue experimentation.

The extracts and/or fractions derived therefrom having activity, without wishing to necessarily be bound by any particular theory, have been identified as cocoa polyphenol(s), which include procyanidins. These cocoa procyanidins have to function as NO (Nitric Oxide) modulators, as non-steroidal anti-inflammatory agents, as modulators of platelet activation, and as cyclo-oxygenase and/or lipoxygenase modulators.

With regard to the cocoa procyanidins, it has been surprisingly found that the cocoa procyanidins have discrete activities, and as such, the cocoa procyanidins have broad applicability to the treatment of a variety of disease conditions, discussed herein below.

COX/LOX-Associated Utilities

Figure 2A:
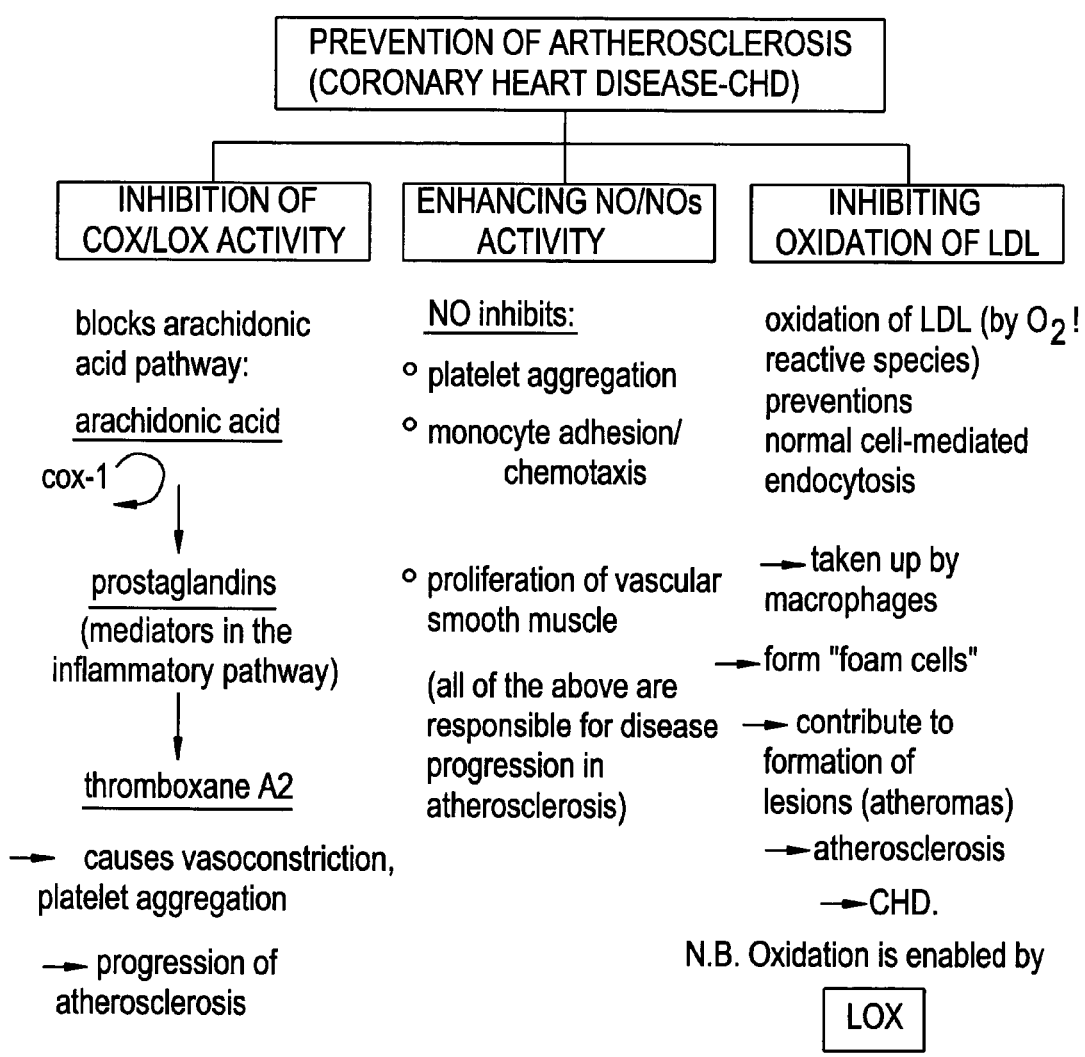
Figure 2B:
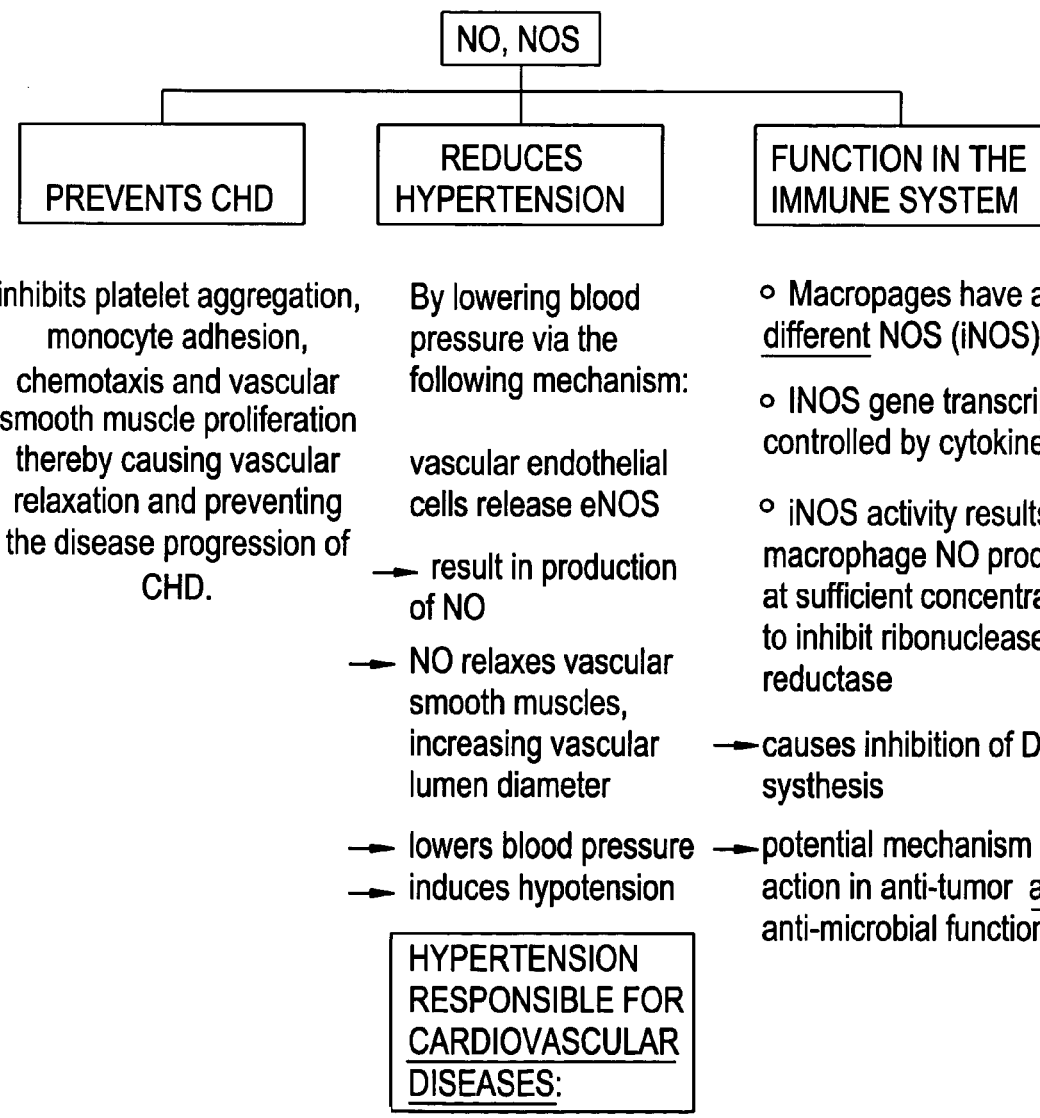

Atherosclerosis, the most prevalent of cardiovascular diseases, is the principle cause of heart attack, stroke and vascular circulation problems. Atherosclerosis is a complex disease which involves many cell types, biochemical events and molecular factors. There are several aspects of this disease, its disease states and disease progression which are distinguished by the interdependent consequences of Low Density Lipoprotein (LDL) oxidation, cyclo-oxygenase (COX)/lipoxygenase (LOX) activity, eicosanoid and endothelin activities and Nitric Oxide (NO) biochemistry. See FIG. 2.

Clinical studies have firmly established that elevated plasma concentrations of LDL are associated with accelerated atherogenesis. The cholesterol that accumulates in atherosclerotic lesions originate primarily in plasma lipoproteins, including LDL. The oxidation of LDL is a critical event in the initiation of atheroma formation and is associated with the enhanced production of the superoxide anion radical ($O_2!$-). Oxidation of LDL by $O_2!\bullet$- or other reactive species (e.g., !OH, ONOO!•-, lipid peroxy radical, copper ion, and iron based proteins) reduces the affinity of LDL for uptake in cells via receptor mediated endocytosis. The oxidatively-modified LDLs are then rapidly taken up by macrophages which subsequently transform into cells closely resembling the "foam cells" observed in early atherosclerotic lesions.

Oxidized lipoproteins can also promote vascular injury through the formation of lipid hydroperoxides within the LDL particle. This event initiates radical chain oxidation reactions of unsaturated LDL lipids, thus producing more oxidized LDL for macrophage incorporation.

The collective accumulation of foam cells engorged with oxidized LDL from these processes results in early "fatty streak" lesions, which eventually progress to the more advanced complex lesions of atherosclerosis leading to coronary disease.

As discussed generally by Jean Marx at page 320 of Science, Vol. 265 (Jul. 15, 1994), each year about 330,000 patients in the United States undergo coronary and/or peripheral angioplasty, a procedure designed to open up blood vessels, e.g., coronary arteries, clogged by dangerous atherosclerotic plaques (atherosclerosis) and thereby restore normal blood flow. For a majority of these patients, the operation works as intended. Nearly 33% of these patients (and maybe more by some accounts), however, develop restenosis, wherein the treated arteries become quickly clogged again. These patients are no better off, and sometimes worse off, than they were before angioplasty. Excessive proliferation of smooth muscle cells (SMCs) in blood vessel walls contributes to restenosis. Increased accumulation of oxidized LDL within lesion SMCs might contribute to an atherogenic-related process like restenosis, as discussed by Zhou et al., "Association Between Prior Cytomegalovirus Infection And The Risk Of Restenosis After Coronary Atherectomy," New England Journal of Medicine, 335:624–630, Aug. 29, 1996, and documents cited therein. Accordingly, utility of the present invention with respect to atherosclerosis can apply to restenosis.

With regard to the inhibition by the cocoa procyanidins of cyclo-oxygenases (COX; prostaglandin endoperoxide synthase), it is known that cyclo-oxygenases are central enzymes in the production of prostaglandins and other arachidonic acid metabolites (i.e., eicosanoids) involved in many physiological processes. COX-1 is a constitutive enzyme expressed in many tissues, including platelets, whereas COX-2, a second isoform of the enzyme, is inducible by various cytokines, hormones and tumor promoters. COX-1 produces thromboxane A2, which is involved in platelet aggregation, which in turn is involved in the progression of atherosclerosis. Its inhibition is the basis for the prophylactic effects on vascular disease.

The activity of COX-1 and COX-2 is inhibited by aspirin and other nonsteroidal anti-inflammatory drugs (NSAIDs). The gastric side effects of NSAIDs are believed to be associated with the inhibition of COX-1. Moreover, it has been found that patients taking NSAIDs on a regular basis have a 40 to 50% lower risk of contracting colorectal cancer when compared to persons not being administered these type of medications. COX-2 mRNA levels are markedly increased in 86% of human colorectal adenocarcinomas.

One significant property of COX-2 expressing cell lines is the enhanced expression of genes which participate in the modulation of apoptosis, i.e., programmed cell death. Several NSAIDs have been implicated in increased cell death and the induction of apoptosis in chicken embryo fibroblasts.

Cellular lipoxygenases are also involved in the oxidative modification of LDL through the peroxidation of unsaturated lipids. The generation of lipid peroxy radicals contributes to the further radical chain oxidation of unsaturated LDL lipids, producing more oxidized LDL for macrophage incorporation.

Lipoxygenase is a highly specific catalyst for the oxidation of unsaturated fatty acids containing a cis,cis-1,4-pentadiene system (Tappel et al, in "The Enzymes" Academic Press, New York, N.Y., pp. 275–283, 1963). The hydroperoxide products are structurally similar to those obtained by autoxidation. Lipoxygenase is a nonheme iron protein. The metal, however, is essential for its enzymatic activity (Grossman et al. Methods. Biochem. Anal. 25:303–329, 1979). The mechanism of lipid oxidation is thus distinct from heme containing lipid oxidation catalysts, i.e., hemoglobin, myoglobin and cytochromes.

A variety of animal cells (i.e. leukocytes, mast cells and tissue cells) contain specific 5-, 12- and 15-lipoxygenase activities catalyzing the formation of leukotrienes and lipoxins. Leukotrienes are generated by 5-lipoxygenase from membrane derived arachidonic acid via the 5-hydroperoxytetraenoic acid intermediate (Samuelsson et al., Science, 237:1171–1176). Leukotrienes mediate a variety of signals in inflammation and immunity, and lipoxins serve as intra- and intercellular messengers in a variety of functions of vasculature and inflammation (Serhan et al, J. Bioenerg. Biomembr. 23:105–122, 1991.) Several flavonoids inhibit animal 5-lipoxygenase (Laughton et al., Biochem. Pharmacol. 42:1673–1681). The inhibition of soybean lipoxygenase activity by select cocoa polyphenol extracts was tested in this work, and it was shown that cocoa polyphenol extract sub-fractions inhibit lipoxygenase activity in vitro. Therefore the cocoa extracts have a utility in the prevention of atherosclerosis via the inhibition of lipid oxidation by lipoxygenase.

It has been surprisingly found that the cocoa procyanidins have utility in the treatment of diseases associated with COX/LOX. In Example 12, COX was inhibited by individual cocoa procyanidins at concentrations similar to the known NSAID Indomethacin.

For COX inhibition, the preferred cocoa procyanidins are oligomers, where n is 2 to 18. In a preferred embodiment, the cocoa procyanidins are oligomers where n is 2 to 10, more preferably 2 to 5. Examples of compounds eliciting inhibitory activity with respect to COX/LOX include dimers, trimers, tetramers and pentamers.

Hence, given the significant inhibitory potency of the cocoa procyanidins on COX-2, coupled with the cytotoxic effects on a putative COX-2 expression colon cancer cell line, the cocoa procyanid ins should possess apoptotic activity as inhibitors of the multi step progression leading to carcinomas, as well as activity as members of the NSAID family of medications possessing a broad spectrum of prophylactic activities.

Further, prostaglandins, the penultimate products of the COX catalyzed conversion of arachidonic acid to prostaglandin $H_2$, are involved in inflammation, pain, fever, fetal development, labor and platelet aggregation. Therefore, the cocoa procyanidins are efficacious for the same conditions as NSAIDs, e.g., against vascular disease, and stroke, etc. Indeed, the inhibition of platelet COX-1, which reduces thromboxane $A_2$ production, is the basis for the prophylactic effects of aspirin on vascular disease.

Inflammation is the response of living tissues to injury. It involves a complex series of enzyme activation, mediator release, extravasation of fluid, cell migration, tissue breakdown and repair. Inflammation is activated by phospholipase $A_2$, which liberates arachidonic acid, the substrate for COX and LOX enzymes. COX converts arachidonic acid to the prostaglandin $PGE_2$, the major eicosanoid detected in inflammatory conditions ranging from acute edema to chronic arthritis. Its inhibition by NSAIDs is a mainstay for treatment.

Arthritis is one of the rheumatic diseases which encompass a wide range of diseases and pathological processes, most of which affect joint tissue. The basic structure affected by these diseases is the connective tissue which includes synovial membranes, cartilage, bone, tendons, ligaments, and interstitial tissues. Temporary connective tissue syndromes include sprains and strains, tendonitis, and tendon sheath abnormalities. The most serious forms of arthritis are rheumatoid arthritis, osteoarthritis, gout and systemic lupus erythematosus.

In addition to the rheumatic diseases, other diseases are characterized by inflammation. Gingivitis and periodontitis follows a pathological picture resembling rheumatoid arthritis. Inflammatory bowel disease refers to idiopathic chronic inflammatory conditions of the intestine, ulcerative colitis and Crohn's disease. Spondylitis refers to chronic inflammation of the joints of the spine. There is also a high incidence of osteoarthritis associated with obesity.

Thus, the cocoa procyanidins have utility in the treatment of conditions involving inflammation, pain, fever, and platelet aggregation.

The prostanoids and endothelins participate not only in animal development (e.g. nerve crest-derived structures) but also in the regulation of the cardiorespiratory systems of adult organisms (Huggins et al., 'ET-1 Induction Of Cyclooxygenase-2 Expression In Rat Mesangial Cells' 1993; Harbome, J. B., The Flavonoids: Advances in Research since 1986', Chapman and Hall, London, 1994; Prins et al., 'Prostglandin E2 and Prostacyclin Inhibit the Production of Endothelin from Cultured Endothelial Cells, J. Biol. Chem., 269:11938–11944, 1994). Vascular effects of prostacyclin include decreased vessel contraction, platelet aggregation, thrombosis formation, smooth muscle cell proliferation, and the entry of low-density lipoproteins into the arterial wall, while the endothelins (ET-1, ET-2, ET-3), $PGE_2$, and thromboxane induce vasoconstriction and platelet aggregation (Kuwaki et al., 'Physiological role of Brain ET on the Central Autonomic Control: From Neuron to Knockout Mouse', 1997; Luscher T. F. 'Platelet-vessel Wall Interactions: Role of Nitric Oxide, Prostglandins, and ET's. Balliere's Clin. Haemotol. 6:609–627, 1993). It has been shown by the inventors that, in an endothelial cell monolayer culture system, cocoa procyanidin extracts induce prostacyclin cell release and inhibit endothelin cell release, hence promoting a state of vessel relaxation and decreased platelet aggregation. The claimed compounds therefore have utility as vasoprotectors in the treatment of vascular disease.

The inhibition of COX by the cocoa procyanidins would also inhibit the formation of postaglandins, e.g., $PGD_2$, $PGE_2$. Thus, the cocoa procyanidins have utility in the treatment of conditions associated with prostaglandins $PGD_2$ and $PGE_2$.

NO-Associated Utilities

Nitric oxide (NO) is known to inhibit platelet aggregation, monocyte adhesion and chemotaxis, and proliferation of vascular smooth muscle tissue which are critically involved in the process of atherogenesis. Evidence supports the view that NO is reduced in atherosclerotic tissues due to its reaction with oxygen free radicals. The loss of NO due to these reactions leads to increased platelet and inflammatory cell adhesion to vessel walls to further impair NO mechanisms of relaxation. In this manner, the loss of NO promotes atherogenic processes, leading to progressive disease states.

Hypertension is a leading cause of vascular diseases, including stroke, heart attack, heart failure, irregular heart beat and kidney failure. Hypertension is a condition where the pressure of blood within the blood vessels is higher than normal as it circulates through the body. When the systolic pressure exceeds 150 mm Hg or the diastolic pressure exceeds 90 mm Hg for a sustained period of time, damage is done to the body. For example, excessive systolic pressure can rupture blood vessels anywhere. When it occurs within the brain, a stroke results. It can also cause thickening and narrowing of the blood vessels which can lead to atherosclerosis. Elevated blood pressure can also force the heart muscle to enlarge as it works harder to overcome the elevated resting (diastolic) pressure when blood is expelled. This enlargement can eventually produce irregular heart beats or heart failure. Hypertension is called the "silent killer" because it causes no symptoms and can only be detected when blood pressure is checked.

The regulation of blood pressure is a complex event where one mechanism involves the expression of constitutive $Ca^{+2}$/calmodulin dependent form of nitric oxide synthase (NOS), abbreviated eNOS. NO produced by this enzyme produces muscle relaxation in the vessel (dilation), which lowers the blood pressure. When the normal level of NO produced by eNOS is not produced, either because production is blocked by an inhibitor or in pathological states, such as atherosclerosis, the vascular muscles do not relax to the appropriate degree. The resulting vasoconstriction increases blood pressure and may be responsible for some forms of hypertension.

Vascular endothelial cells contain eNOS. NO synthesized by eNOS diffuses in diverse directions, and when it reaches the underlying vascular smooth muscle, NO binds to the heme group of guanylyl cyclase, causing an increase in cGMP. Increased cGMP causes a decrease in intracellular free $Ca^{+2}$. Cyclic GMP may activate a protein kinase that phosphorylates $Ca^{+2}$ transporters, causing $Ca^{+2}$ to be sequestered in intracellular structures in the muscle cells. Since muscle contraction requires $Ca^{+2}$, the force of the contraction is reduced as the $Ca^{+2}$ concentration declines. Muscle relaxation allows the vessel to dilate, which lowers the blood pressure. Inhibition of eNOS therefore causes blood pressure to increase.

When the normal level of NO is not produced, either because production is blocked by administration of an NOS inhibitor or possibly, in pathological states, such as atherosclerosis, the vascular muscles do not relax to the appropriate degree. The resulting vasoconstriction increases blood pressure and may be responsible for some forms of hypertension. There is considerable interest in finding therapeutic ways to increase the activity of eNOS in hypertensive patients, but practical therapies have not been reported. Pharmacological agents capable of releasing NO, such as nitroglycerin or isosorbide dinitrate, remain mainstays of vasorelaxant therapy.

Although the cocoa procyanidins inhibit the oxidation of LDL, the more comprehensive effects of these compounds is their multidimensional effects on atherosclerosis via NO. NO modulation by the cocoa procyanidins brings about a collage of beneficial effects, including the modulation of hypertension, lowering NO affected hypercholesterolemia, inhibiting platelet aggregation and monocyte adhesion, all of which are involved with the progression of atherosclerosis.

The role of NO in the immune system is different from its function in blood vessels. Macrophages contain a form of NOS that is inducible, rather than constitutive, referred to as iNOS. Transcription of the iNOS gene is controlled both positively and negatively by a number of biological response modifiers called cytokines. The most important inducers are gamma-interferon, tumor necrosis factor, interleukin-1, interleukin-2 and lipopolysaccharide (LPS), which is a component of the cell walls of gram negative bacteria. Stimulated macrophages produce enough NO to inhibit ribonuclease reductase, the enzyme that converts ribonucleotides to the deoxyribonucleotides necessary for DNA synthesis. Inhibition of DNA synthesis may be an important way in which macrophages and other tissues possessing iNOS can inhibit the growth of rapidly dividing tumor cells or infectious bacteria.

With regard to the effects of NO and infectious bacteria, microorganisms play a significant role in infectious processes which reflect body contact and injury, habits, profession, environment of the individual, as well as food borne diseases brought about by improper storage, handling and contamination.

The cocoa procyanidins, combinations thereof, and compositions containing them are useful in the treatment of conditions associated with modulating NO concentrations.

Inhibition of Platelet Aggregation

Blood platelets play a major role in coronary artery disease. Platelets are found at the site of early atherosclerotic lesions. When activated, they secrete potent mitogenic factors such as platelet derived growth factor, transforming growth factor-β and epidermal growth factor, which lead to smooth muscle proliferation and progression of atherosclerotic lesions.

Additionally, enhanced platelet reactivity and spontaneous platelet aggregates are crucially involved in thrombus formation, which is largely responsible for the pathogenesis of acute myocardial infarction, unstable angina and percutaneous coronary intervention. Therapy with antiplatelet agents (such as aspirin) significantly decrease the incidence of primary and secondary coronary events (Schafer, A. I. 'Antiplatelet Therapy", Am. J. Med. 101:199–209, 1996).

Platelet function depends on the interactions of membrane glycoproteins, such as GPIIb/IIIa, which act as receptors for adhesive proteins on the platelet surface. Agonists of GPIIb/IIIa facilitate the conformational change necessary for the receptor to become receptive to ligands which bind simultaneously to two separate platelets, thereby cross-linking and aggregating the platelets. Antagonists of the GPIIb/IIIa receptor prevent activation of the receptor, thereby preventing platelet activation. Pharmacological intervention directed against the GPIIb/IIIa receptor is therefore being pioneered in the treatment of ischemic heart disease. Several GPIIb/IIIa agonists have been used in clinical trials in recent years, and have been shown to have considerable benefit in various treatment regimes (Vorchheimer et al, JAMA, 281: 15:1407–1413, 1999).

It has been found that consumption of a cocoa beverage with an enhanced cocoa procyanidin content results in the suppression of activation of the GPIIbIIIa receptor. Therefore, the cocoa procyanidins have a utility in the treatment and prevention of atherosclerosis.

It has been shown that the cocoa procyanidins have a potent antioxidant activity (as disclosed in Romanczyk et al, U.S. Ser. No. 5,554,645), which is known to be due to the inhibition of free radicals. Given that NO is a free radical and that the cocoa procyanidins are strong antioxidants, it was suspected that the administration of the cocoa procyanidins to experimental in vitro and in vivo models would have caused a reduction in NO levels. Any reduction in NO would have resulted in a hypertensive, rather than a hypotensive effect. Contrary to expectations, the cocoa procyanidins elicited increases in NO in the in vitro experiments and produced a hypotensive effect in the in vivo studies (Examples 17 and 18). These results were not anticipated and completely unexpected.

Example 8 describes the hypotensive effects elicited by the cocoa procyanidins in an in vivo animal model, thus demonstrating the efficacy of the cocoa procyanidins in the treatment of hypertension. In this example, the cocoa procyanidins, combinations thereof and compositions comprising the same comprise oligomers wherein n is 2 to 18, and preferably, n is 2 to 10.

Example 9 describes the modulation of NO production by the cocoa procyanidins in an in vitro model. In this example, the cocoa procyanidins, combinations thereof and compositions comprising the same comprise oligomers wherein n is 2 to 18, and preferably n is 2 to 10.

Further, Example 6 provides evidence for the formation of $Cu^{+2}$-, $Fe^{+2}$- and $Fe^{+3}$-oligomer complexes detected by MALDI/TOF/MS. These results indicate that the cocoa procyanidins can complex with copper and/or iron ions to minimize their effects on LDL oxidation.

Example 10 describes the effects of the cocoa procyanidins on macrophage NO production. In this example, the results demonstrate that the cocoa procyanidins induce monocyte/macrophage NO production, both independent and dependent of stimulation by lipopolysaccharide (LPS) or cytokines. Macrophages producing NO can inhibit the growth of infectious bacteria.

Formulations and Methods

Therefore, collectively, the cocoa procyanidins, combinations thereof and compositions containing them have exhibited a wide array of activities and functions including NO or NO-synthase modulator, non-steroidal anti-inflammatory agent, platelet activation modulator, nonsteroidal anti-inflammatory agent, modulator of the immune system, and cyclo-oxygenase and/or lipoxygenase modulator.

For treatment or prevention of vascular diseases including restenosis and atherosclerosis, a cocoa procyanidin or mixture of cocoa procyanidin monomer and/or oligomers or a composition comprising cocoa procyanidin or procyanidins, alone or with other treatment, may be administered as desired by the skilled medical practitioner, from this disclosure and knowledge in the art, e.g., at the first signs or symptoms of restenosis and/or atherosclerosis, immediately prior to, concomitant with or after angioplasty, or as soon thereafter as desired by the skilled medical practitioner, without any undue experimentation required; and the administration of the inventive compound or compounds or a composition thereof, alone or with other treatment, may be continued as a regimen, e.g., monthly, bimonthly, biannually, annually, or in some other regimen, by the skilled medical practitioner for such time as is necessary, without any undue experimentation required.

Further, the cocoa procyanidins, combinations thereof and compositions comprising the same have been shown to produce a hypotensive effect in vivo and induce NO in vitro. These results have practical application in the treatment of hypertension and in clinical situations involving hypercholesterolemia, where NO levels are markedly reduced.

Formulations of the cocoa procyanidins, combinations thereof and compositions containing them can be prepared with standard techniques well known to those skilled in the pharmaceutical, food science, medical and veterinary arts, in the form of a liquid, suspension, tablet, capsule, injectable solution or suppository, for immediate or slow-release of the active compounds. The carrier may also be a polymeric delayed release system. Synthetic polymers are particularly useful in the formulation of a composition having controlled release. An early example of this was the polymerization of methyl methacrylate into spheres having diameters less than one micron to form so-called nano particles, reported by Kreuter, J., Microcapsules and Nanoparticles in Medicine and Pharmacology, M. Donbrow (Ed). CRC Press, p. 125–148.

A frequent choice of a carrier for pharmaceuticals and more recently for antigens is poly (d,1-lactide-co-glycolide) (PLGA). This is a biodegradable polyester that has a long history of medical use in erodable sutures, bone plates and other temporary prostheses where it has not exhibited any toxicity. A wide variety of pharmaceuticals have been formulated into PLGA microcapsules. A body of data has accumulated on the adaption of PLGA for controlled release, for example, as reviewed by Eldridge, J. H., et al. Current Topics in Microbiology and Immunology, 1989, 146:59–66. The entrapment in PLGA microspheres of 1 to 10 microns in diameter can be effective when administered orally. The PLGA microencapsulation process uses a phase separation of a water-in-oil emulsion. The cocoa procyanidins are prepared as an aqueous solution and the PLGA is dissolved in a suitable organic solvents such as methylene chloride and ethyl acetate. These two immiscible solutions are co-emulsified by high-speed stirring. A non-solvent for the polymer is then added, causing precipitation of the polymer around the aqueous droplets to form embryonic microcapsules. The microcapsules are collected, and stabilized with one of an assortment of agents including polyvinyl alcohol (PVA), alginates and methyl cellulose. The solvent is subsequently removed by either drying in vacuo or solvent extraction.

Additionally, with regard to the preparation of slow-release formulations, the disclosures of U.S. Pat. Nos. 5,024,843, 5,091,190, 5,082,668, 4,612,008 and 4,327,725 are hereby incorporated herein by reference.

Additionally, selective processing coupled with the identification of cocoa genotypes of interest could be used to prepare Standard-of-Identity (SOI) and non-SOI chocolate products as vehicles to deliver the active compounds to a patient in need of treatment for the disease conditions described above, as well as a means for the delivery of conserved levels of the cocoa procyanidins.

A method of producing cocoa butter and/or cocoa solids having conserved levels of cocoa polyphenols from cocoa beans uses a unique combination of processing steps which does not require separate bean roasting or liquor milling equipment, allowing for the option of processing cocoa beans without exposure to severe thermal treatment for extended periods of time and/or the use of solvent extraction of fat. The benefit of this process lies in the enhanced conservation of polyphenols in contrast to that found in traditional cocoa processing, such that the ratio of the initial amount of polyphenol found in the unprocessed bean to that obtainable after processing is less than or equal to 2. Partially defatted cocoa solids having a high cocoa polyphenol (CP) content, including a high cocoa procyanidin content, can be obtained by processing the cocoa beans directly to cocoa solids without a bean or nib roasting step. This method conserves the cocoa polyphenols because it omits the traditional roasting step. This method consists essentially of the steps of: (a) heating the cocoa beans to an internal bean temperature just sufficient to reduce the moisture content to about 3% by weight and to loosen the cocoa shell; (b) winnowing the cocoa nibs from the cocoa shells; (c) screw pressing the cocoa nibs; and (d) recovering the cocoa butter and partially defatted cocoa solids which contain cocoa polyphenols including cocoa procyanidins. Optionally, the cocoa beans are cleaned prior to the heating step, e.g., in an air fluidized bed density separator. The winnowing can also be carried out in the air fluidized bed density separator. Preferably, the cocoa beans are heated to an internal bean temperature of about 100° C. to about 110° C., more preferably less than about 105° C., typically using a infra red heating apparatus for about 3 to 4 minutes. If desired, the cocoa solids can be alkalized and/or milled to a cocoa powder.

The internal bean temperature (IBT) can be measured by filling an insulated container such as a thermos bottle with beans (approximately 80–100 beans). The insulated container is then appropriately sealed in order to maintain the temperature of the sample therein. A thermometer is inserted into the bean-filled insulated container and the temperature of the thermometer is equilibrated with respect to the beans in the thermos. The temperature reading is the IBT temperature of the beans. IBT can also be considered the equilibrium mass temperature of the beans.

Cocoa beans can be divided into four categories based on their color: predominately brown (fully fermented), purple/brown, purple, and slaty (unfermented). Preferably, the cocoa solids are prepared from underfermented cocoa beans which have a higher cocoa polyphenol content than fermented beans. Underfermented beans include slaty cocoa beans, purple cocoa beans, mixtures of slaty and purple cocoa beans, mixtures of purple and brown cocoa beans, or mixture of slaty, purple, and brown cocoa beans. More preferably, the cocoa beans are slaty and/or purple cocoa beans.

As discussed above, the cocoa polyphenol (CP) content, including the cocoa procyanidin content, of roasted cocoa nibs, chocolate liquor, and partially defatted or nonfat cocoa solids is higher when they are prepared from cocoa beans or blends thereof which are underfermented, i.e., beans having a fermentation factor of 275 or less.

The "fermentation factor" is determined using a grading system for characterizing the fermentation of the cocoa beans. Slaty is designated 1, purple is 2, purple/brown is 3, and brown is 4. The percentage of beans falling within each category is multiplied by the weighted number. Thus, the "fermentation factor" for a sample of 100% brown beans would be 100×4 or 400, whereas for a 100% sample of purple beans it would be 100×2 or 200. A sample of 50% slaty beans and 50% purple beans would have a fermentation factor of 150 [(50×1)+(50×2)].

An extract containing cocoa polyphenols including cocoa procyanidins can be prepared by solvent extracting the partially defatted cocoa solids, and purifying the extract to remove the xanthines caffeine and theobromine.

Such compositions can be administered to a subject or patient in need of such administration in dosages and by techniques well known to those skilled in the medical, nutritional or veterinary arts taking into consideration the data herein, and such factors as the age, sex, weight, genetics and condition of the particular subject or patient, the route of administration, relative concentration of particular oligomers, and toxicity (e.g., $LD_{50}$).

Suitable compositions of the invention for human or veterinary use include edible compositions for oral administration, such solid or liquid formulations, for example, capsules, tablets, pills and the like; chewable solid formulations, beverage formulations, or dried beverage formulations for reconstitution; liquid preparations for orifice administration, e.g., by oral, by nasal, by anal, by vaginal administration via suspensions, syrups or elixirs; and ingestable preparations for parenteral, subcutaneous, intradermal, intramuscular or intravenous administration e.g., suspensions or emulsions. The above compositions maybe chocolate flavored if the high cocoa polyphenol solids are used in the composition. However, if the cocoa extract is used in the composition, chocolate or other flavoring agents may be included in the composition, particularly if the composition is an edible composition. The active ingredient in the compositions may complex with proteins and, when administered into the bloodstream, clotting may occur due to the precipitation of blood proteins. The skilled artisan should take this into account. In such compositions the active cocoa procyanidin may be in admixture with a suitable carrier, diluent, or excipient such as sterile water, physiological saline, glucose, DMSO, ethanol, or the like. The cocoa extract or cocoa procyanidin fractions can be provided in lyophilized form for reconstituting for example, in an edible liquid or in isotonic aqueous, saline, glucose or DMSO buffer. In certain saline solutions, some precipitation has been observed. Precipitation may be employed as a means to isolate cocoa procyanidins, e.g. by a "salting out" procedure.

Example 14 describes the utility of a procyanidin-enriched cocoa beverage in the inhibition of platelet activation. A preferred beverage or beverage mix comprises: high cocoa polyphenol solids and/or cocoa extract; and optionally a natural or artificial sweetener, a natural or synthetic flavorant, and a dairy product. The beverage may also be a carbonated beverage. The sweetener may be a sugar syrup/solids, or a sugar substitute. The term "sugar substitute" includes bulking agents, sugar alcohols, (i.e. polyols such as glycerol), high potency sweeteners or combinations thereof. Nutritive carbohydrate sweeteners with varying degrees of sweetness intensity may be any of those typically used in the art and include, but are not limited to, sucrose, dextrose, fructose, lactose, maltose, glucose syrup solids, corn syrup solids, invert sugar, hydrolyzed lactose, honey, maple sugar, brown sugar, molasses and the like. Sugar substitutes may partially or totally replace the nutritive carbohydrate sweetener. High potency sugar substitutes include aspartame, cyclamates, saccharin, acesulfame-K, neohesperidin, dihydrochalcone, sucralose, alitame, stevia sweeteners, glycyrrhizin, thaumatin and the like as well as mixtures thereof. Exemplary sugar alcohols include those typically used in the art such as sorbitol, mannitol, xylitol, maltitol, isomalt, lactitol and the like. Exemplary dairy components are nonfat milk solids, milk fat, sweet cream, buttermilk and skim milk.

Example 15 describes the formulation of cocoa procyanidins tablets, for use in the pharmaceutical, diet supplement and food areas. Example 16 describes the preparation of the cocoa procyanidins as capsules for similar applications. Example 17 describes the preparation of Standard of Identity (SOI) and non-SOI chocolates containing the high cocoa polyphenol extract or cocoa solids obtained from methods described herein.

Kits

The active cocoa extract may be provided in a kit includes a separate container containing a suitable carrier, diluent or excipient, and optionally other active ingredients which will depend upon the health benefit to be achieved, and additional agent(s) which can be provided in separate container(s) or in admixture with the active cocoa procyanidin(s). The kit may also include instructions for mixing or combining the ingredients and/or the administration.

EXAMPLES

Example 1

Cocoa Source and Method of Preparation

Several *Theobroma cacao* genotypes which represent the three recognized horticultural races of cocoa (Enriquez et al, Cocoa Cultivars Register IICA, Turrialba, Cost Rica 1967; Engels, Genetic Resources of Cacao: A Catalogue of the CATIE Collection, Tech. Bull. 7, Turrialba, Costa Rica, 1981) were obtained from the three major cocoa producing origins of the world. A list of those genotypes used in this study are shown in Table 1. Harvested cocoa pods were opened and the beans with pulp were removed for freeze drying. The pulp was manually removed from the freeze dried mass and the beans were subjected to analysis as follows. The unfermented, freeze dried cocoa beans were first manually dehulled, and ground to a fine powdery mass with a TEKMAR Mill. The resultant mass was then defatted overnight by Soxhlet extraction using redistilled hexane as the solvent. Residual solvent was removed from the defatted mass by vacuum at ambient temperature.

TABLE 1

Description of *Theobroma cacao* Source Material

| GENOTYPE | ORIGIN | HORTICULTURAL RACE |
|---|---|---|
| UIT-1 | Malaysia | Trinitario |
| Unknown | West Africa | Forastero |
| ICS-100 | Brazil | Trinitario (Nicaraguan Criollo ancestor) |
| ICS-39 | Brazil | Trinitario (Nicaraguan Criollo ancestor) |
| UF-613 | Brazil | Trinitario |
| EEG-48 | Brazil | Forastero |
| UF-12 | Brazil | Trinitario |
| NA-33 | Brazil | Forastero |

Example 2

Procyanidin Extraction Procedures

A. Method 1

Procyanidins were extracted from the defatted, unfermented, freeze dried cocoa beans of Example 1 using a modification of the method described by Jalal and Collin ('Polyphenols of Mature Plant, Seedling and Tissue Cultures of *Theobroma* Cacao', Phytochemistry, 6, 1377–1380, 1977). Procyanidins were extracted from 50 gram batches of the defatted cocoa mass with 2×400 mL 70% acetone/deionized water followed by 400 mL 70% methanol/deionized water. The extracts were pooled and the solvents removed by evaporation at 45° C. with a rotary evaporator held under partial vacuum. The resultant aqueous phase was diluted to 1 L with deionized water and extracted 2× with 400 mL $CHCl_3$. The solvent phase was discarded. The aqueous phase was then extracted 4× with 500 mL ethyl acetate. Any resultant emulsions were broken by centrifugation on a Sorvall RC 28S centrifuge operated at 2,000× for 30 min. at 10° C. To the combined ethyl acetate extracts, 100–200 mL deionized water was added. The solvent was removed by evaporation at 45° C. with a rotary evaporator held under partial vacuum. The resultant aqueous phase was frozen in liquid $N_2$ followed by freeze drying on a LABCONCO Freeze Dry System. The yields of crude procyanidins that were obtained from the different cocoa genotypes are listed in Table 2.

TABLE 2

Crude Procyanidin Yields

| GENOTYPE | ORIGIN | HORTICULTUREAL RACE |
|---|---|---|
| UIT-1 | Malaysia | 3.81 |
| Unknown | West Africa | 2.55 |
| ICS-100 | Brazil | 3.42 |
| ICS-39 | Brazil | 3.45 |
| UF-613 | Brazil | 2.98 |
| EEG-48 | Brazil | 3.15 |
| UF-12 | Brazil | 1.21 |
| NA-33 | Brazil | 2.23 |

B. Method 2

Alternatively, procyanidins are extracted from defatted, unfermented, freeze dried cocoa beans of Example 1 with 70% aqueous acetone. Ten grams of defatted material was slurried with 100 mL solvent for 5–10 min. The slurry was centrifuged for 15 min. at 4° C. at 3000×g and the supernatant passed through glass wool. The filtrate was subjected to distillation under partial vacuum and the resultant aqueous phase frozen in liquid $N_2$, followed by freeze drying on a LABCONCO Freeze Dry System. The yields of crude procyanidins ranged from 15–20%.

Without wishing to be bound by any particular theory, it is believed that the differences in crude yields reflected variations encountered with different genotypes, geographical origin, horticultural race, and method of preparation.

Example 3

Partial Purification of Cocoa Procyanidins by Gel Permeation Chromatography

A. Method 1

Procyanidins obtained from Example 2 were partially purified by liquid chromatography on Sephadex LH-20 (28×2.5 cm). Separations were aided by a step gradient from deionized water into methanol. The initial gradient composition started with 15% methanol in deionized water which was followed step wise every 30 min. with 25% methanol in deionized water, 35% methanol in deionized water, 70% methanol in deionized water, and finally 100% methanol. The effluent following the elution of the xanthine alkaloids (caffeine and theobromine) was collected as a single fraction. The fraction yielded a xanthine alkaloid free subfraction which was submitted to further subfractionation to yield five subfractions designated MM2A through MM2E. The solvent was removed from each subfraction by evaporation at 45° C. with a rotary evaporator held under partial vacuum. The resultant aqueous phase was frozen in liquid $N_2$ and freeze dried overnight on a LABCONCO Freeze Dry System. A representative gel permeation chromatogram showing the fractionation is shown in FIG. 3. Approximately, 100 mg of material was subfractionated in this manner.

Chromatographic Conditions: Column; 28×2.5 cm Sephadex LH-20, Mobile Phase: Methanol/Water Step Gradient, 15:85, 25:75, 35:65, 70:30, 100:0 Stepped at ½ Hour Intervals, Flow Rate; 1.5 mL/min, Detector; UV at $\lambda_1$=254 nm and $\lambda_2$=365 nm, Chart Speed: 0.5 mm/min, Column Load; 120 mg.

B. Method 2

Procyanidins obtained as in Example 2 were partially purified by liquid chromatography on Sephadex LH 20 (72.5×2.5 cm), using 100% methanol as the eluting solvent, at a flow rate of 3.5 mL/min. Fractions of the eluent were collected after the first 1.5 hours, and the fractions were concentrated by a rotary evaporator, redissolved in water and freeze dried. These fractions were referred to as pentamer enriched fractions. Approximately 2.00 g of the extract obtained from Example 2 was subfractionated in this manner.

Example 4

Analytical HPLC Analysis of Procyanidin Extracts

Method 1. Reverse Phase Separation

Figure 4:
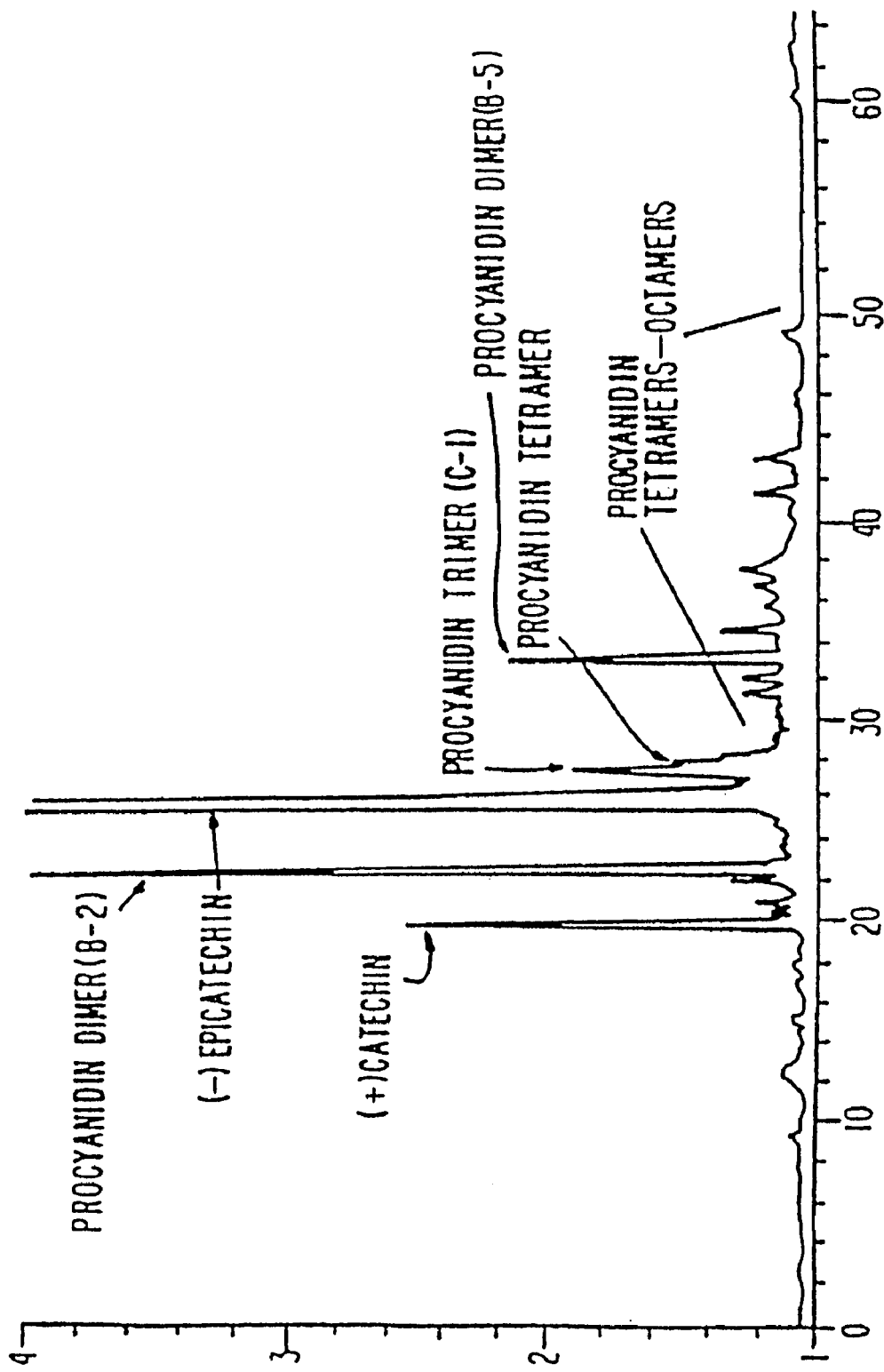
FIG. 4 shows a representative reverse-phase HPLC chromatogram showing the separation (elution profile) of cocoa procyanidins extracted from unfermented cocoa.

Procyanidin extracts obtained from Examples 2 & 3 were filtered through a 0.45µ filter and analyzed by a Hewlett Packard 1090 ternary HPLC system equipped with a Diode Array detector and a HP model 1046A Programmable Fluorescence Detector. Separations were effected at 45° C. on a Hewlett-Packard 5μ Hypersil ODS column (200×2.1 mm). The flavanols and procyanidins were eluted with a linear gradient of 60% B into A followed by a column wash with B at a flow rate of 0.3 mL/min. The mobile phase composition was B=0.5% acetic acid in methanol and A=0.5% acetic acid in nanopure water. Acetic acid levels in A and B mobile phases can be increased to 2%. Components were detected by fluorescence, where $\lambda_{ex}$=276 nm and $\lambda_{ex}$=316 nm and by UV at 280 nm. Concentrations of (+)-catechin and (−)-epicatechin were determined relative to reference standard solutions. Procyanidin levels were estimated by using the response factor for (−)-epicatechin. A representative HPLC chromatogram showing the separation of the various components is shown in FIG. 4 for one cocoa genotype. Similar HPLC profiles were obtained from the other cocoa genotypes.

HPLC Conditions:

| Column: | 200 × 2.1 mm Hewlett Packard Hypersil ODS (5 μ) |
|---|---|
| Guard column: | 20 × 2.1 mm Hewlett Packard Hypersil ODS (5 μ) |
| Detectors: | Diode Array @ 280 nm |
| Fluorescence | λex = 276 nm; |
| | λem = 316 nm. |
| Flow rate: | 0.3 mL/min. |
| Column Temperature: | 45° C. |

| Gradient: Time (min) | 0.5% Acetic Acid in nanopure water | 0.5% Acetic acid in methanol |
|---|---|---|
| 0 | 100 | 0 |
| 50 | 40 | 60 |
| 60 | 0 | 100 |

Method 2. Normal Phase Separation

Figure 5:
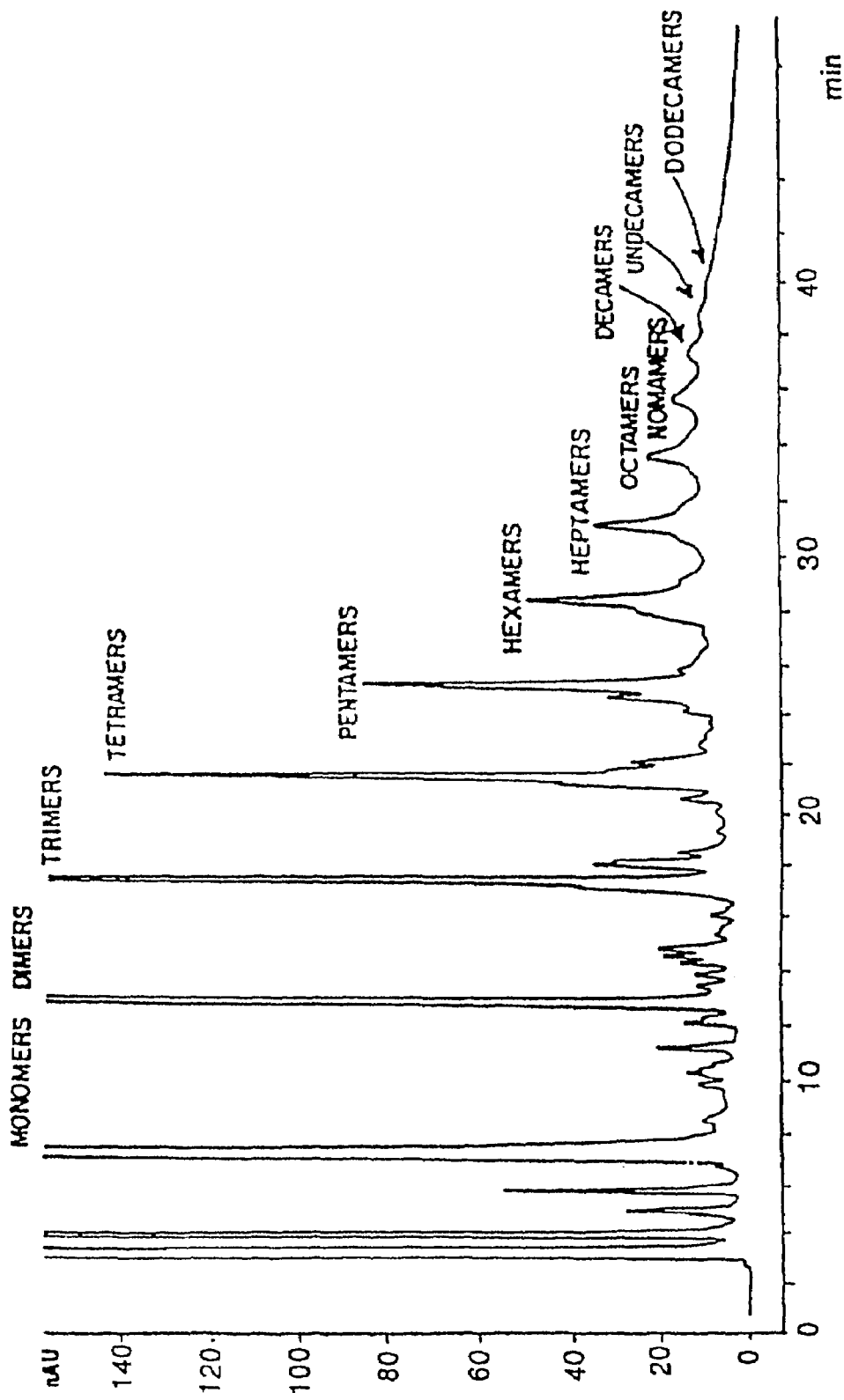
FIG. 5 shows a representative normal phase HPLC separation of cocoa procyanidins extracted from unfermented cocoa.

Procyanidin extracts obtained from previous examples were filtered through a 0.45μ filter and analyzed by a Hewlett Packard 1090 Series II HPLC system equipped with a HP model 1046A Programmable Fluorescence detector and Diode Array detector. Separations were effected at 37° C. on a 5μ Phenomenex Lichrosphere® Silica 100 column (250×3.2 mm) connected to a Supelco Supelguard LC-Si 5μ guard column (20×4.6 mm). Procyanidins were eluted by linear gradient under the following conditions: (Time, % A, % B); (0, 82, 14), (30, 67.6, 28.4), (60, 46, 50), (65, 10, 86), (70, 10, 86) followed by an 8 min. re-equilibration. Mobile phase composition was A=dichloromethane, B=methanol, and C=acetic acid:water at a volume ratio of 1:1. A flow rate of 0.5 mL/min. was used. Components were detected by fluorescence, where $\lambda^{ex}$=276 nm and $\lambda^{em}$=316 nm or by UV at 280 nm. A representative HPLC chromatogram showing the separation of the various procyanidins is shown in FIG. 5 for one genotype. Similar HPLC profiles were obtained from other cocoa genotypes.

HPLC Conditions: 250×3.2 mm Phenomenex Lichrosphere® Silica 100 column (5μ) 20×4.6 mm Supelco Supelguard LC-Si (5μ) guard column

| Detectors: | Photodiode Array @ 280 nm |
|---|---|
| | Fluorescence $\lambda^{ex}$ = 276 nm; |
| | $\lambda^{em}$ = 316 nm. |

| Flow rate: | 0.5 mL/min. |
|---|---|
| Column Temperature: | 37° C. |

| Gradient: Time (min.) | $CH_2$—$Cl_2$ | Methanol | Acetic Acid/Water (1:1) |
|---|---|---|---|
| 0 | 82 | 14 | 4 |
| 30 | 67.6 | 28.4 | 4 |
| 60 | 46 | 50 | 4 |
| 65 | 10 | 86 | 4 |
| 70 | 10 | 86 | 4 |

Example 5

Purification of Oligomeric Fractions from Pentamer Enriched Fractions

Preparative Normal Phase Separation

The pentamer enriched fractions obtained as in Example 4 were further purified by preparative normal phase chromatography by modifying the method of Rigaud et al., (J. Chrom. 654: 255–260, 1993).

Separations were affected at ambient temperature on a 5μ Supelcosil LC-Si 100 Å column (50×2 cm), with an appropriate guard column. Procyanidins were eluted by a linear gradient under the following conditions: (time, % A, % B, flow rate); (0, 92.5, 7.5, 10); (10, 92.5, 7.5, 40); (30, 91.5, 18.5, 40); (145, 88, 22, 40); (150, 24, 86, 40); (155, 24, 86, 50); (180, 0, 100, 50). Prior to use, the mobile phase components were mixed by the following protocol:

Solvent A preparation (82% $CH_2Cl_2$, 14% methanol, 2% acetic acid, 2% water):
1. Measure 80 mL of water and dispense into a 4 L bottle.
2. Measure 80 mL of acetic acid and dispense into the same 4 L bottle.
3. Measure 560 mL of methanol and dispense into the same 4 L bottle.
4. Measure 3280 mL of methylene chloride and dispense into the 4 L bottle.
5. Cap the bottle and mix well.
6. Purge the mixture with high purity Helium for 5–10 minutes to degas.

Repeat steps 1–6 two times to yield 8 volumes of solvent A.

Solvent B preparation (96% methanol, 2% acetic acid, 2% water):
1. Measure 80 mL of water and dispense into a 4 L bottle.
2. Measure 80 mL of acetic acid and dispense into the same 4 L bottle.
3. Measure 3840 mL of methanol and dispense 3840 mL of methanol and dispense into the same 4 L bottle.
4. Cap the bottle and mix well.
5. Purge the mixture with high purity Helium for 5–10 minutes to degas.

Repeat steps 1–5 to yield 4 volumes of solvent B. Mobile phase composition was A=methylene chloride with 2% acetic acid and 2% water; B=methanol with 2% acetic acid and 2% water. The column load was 0.7 g in 7 mL components were detected by UV at 254 nm. A typical preparative normal phase HPLC separation of cocoa procyanidins is shown in FIG. 5.

HPLC Conditions: Column: 50×2 cm 5μ Supelcosil LC-Si run @ ambient temperature.
Mobile Phase: A=Methylene Chloride with 2% Acetic Acid and 2% Water.
B=Methanol with 2% Acetic Acid and 2% Water.
Gradient/Flow Profile:

| TIME (MIN) | % A | % B | FLOW RATE (mL/min) |
|---|---|---|---|
| 0 | 92.5 | 7.5 | 10 |
| 10 | 92.5 | 7.5 | 40 |
| 30 | 91.5 | 8.5 | 40 |
| 145 | 88.0 | 22.0 | 40 |
| 150 | 24.0 | 86.0 | 40 |
| 155 | 24.0 | 86.0 | 50 |
| 180 | 0.0 | 100.0 | 50 |

Example 6

MALDI-TOF/MS Analysis of

High Molecular Weight Procyanidin Oligomers

An analytical examination was made on GPC eluants associated with high molecular weight procyanidin oligomers as prepared in Example 3, Method A. The objective was to determine whether procyanidin oligomers with n>18 were present. If present, these oligomers represent additional cocoa procyanidins. Adjustments to existing methods of isolation, separation and purification embodied in the invention can be made to obtain these oligomers for subsequent in vitro and in vivo evaluation for anti-cancer, anti-tumor or antineoplastic activity, antioxidant activity, inhibit DNA topoisomerase II enzyme, inhibit oxidative damage to DNA, and have antimicrobial, NO or NO-synthase, apoptosis, platelet aggregation, and blood or in vivo glucose-modulating activities, as well as efficacy as non-steroidal anti-inflammatory agents.

Figure 6:
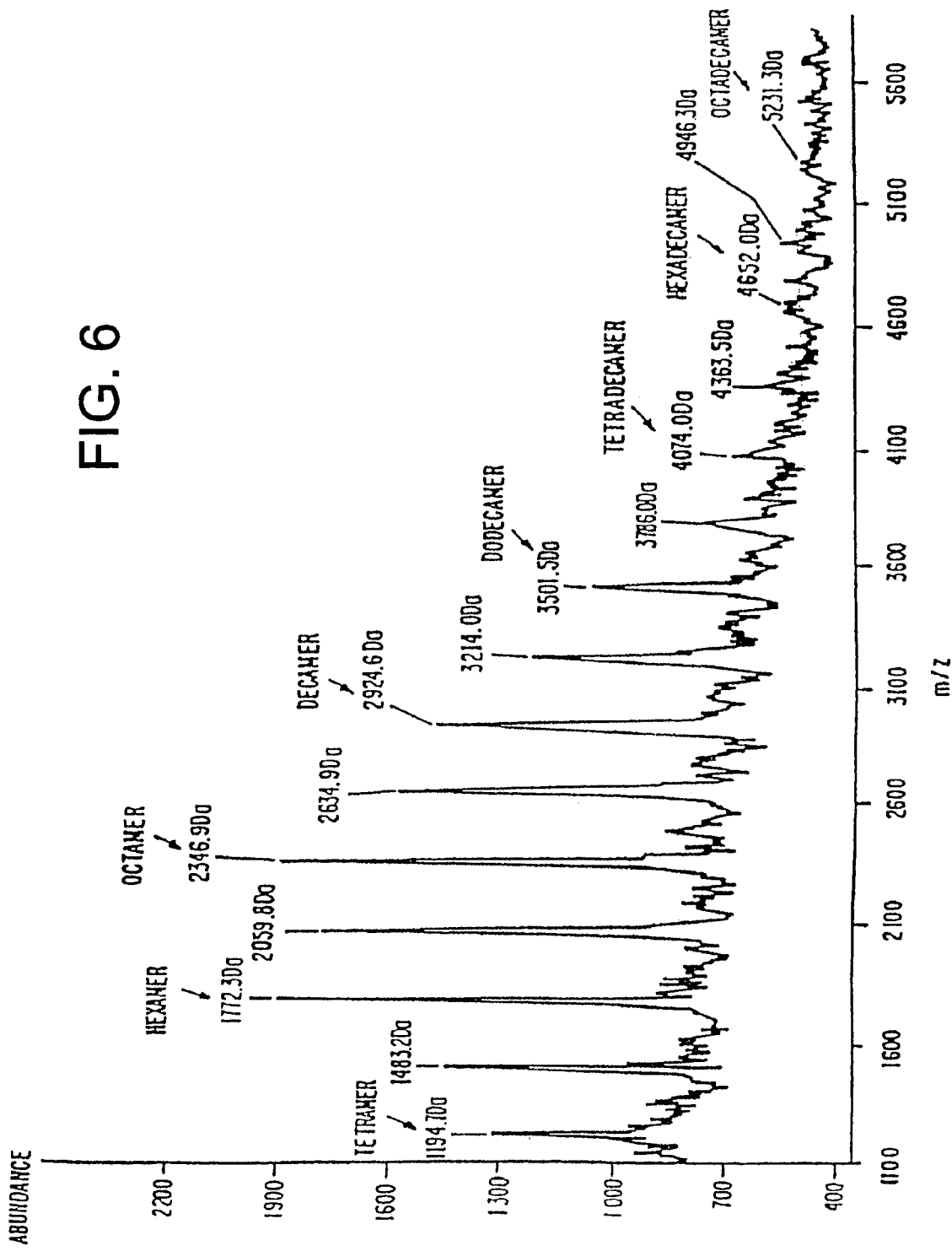
FIG. 6 shows a MALDI-TOF mass spectrum of cocoa procyanidin oligomers (tetramers to octadecamers).

FIG. 6 represents a MALDI-TOF mass spectrum of the GPC eluant sample described above. The $[M+Na]^+$ and/or $[M+K]^+$ and/or $[M+2Na]^+$ ions characterizing procyanidin oligom representative of tetramers through octadecamers are clearly evident.

It was learned that an acid and heat treatment will cause the hydrolysis of procyanidin oligomers. Therefore, the invention comprehends the controlled hydrolysis of high molecular weight procyanidin oligomers (e.g. where n is 13 to 18) as a method to prepare lower molecular weight procyanidin oligomers (e.g. where n is 2 to 12).

TABLE 3

Composition of Fractions Obtained:
goes with Example 3

| Fraction (Time) | Monomer (% Area) | Drimer (% Area) | Trimer (% Area) | Tetramer (% Area) | Pentamer (% Area) | Hexamer (% Area) | Heptamer (% Area) | Octamer (% Area) | Nonamer (% Area) | Decamer (% Area) | Undecamer (% Area) | Others (% Area) |
|---|---|---|---|---|---|---|---|---|---|---|---|---|
| 1:15 | 3 | 8 | 16 | 3 | ND | ND | ND | ND | ND | ND | ND | ND |
| 1.44 | 67 | 19 | 10 | 3 | 1 | tr | tr | tr | tr | tr | tr | tr |
| 2:13 | 30 | 29 | 24 | 11 | 4 | 1 | tr | tr | tr | tr | tr | tr |
| 2.42 | 2 | 16 | 31 | 28 | 15 | 6 | 2 | tr | tr | tr | tr | tr |
| 3:11 | 1 | 12 | 17 | 25 | 22 | 13 | 7 | 2 | 1 | tr | tr | tr |
| 3:40 | tr | 18 | 13 | 18 | 20 | 15 | 10 | 5 | 2 | tr | tr | tr |
| 4:09 | tr | 6 | 8 | 17 | 21 | 19 | 14 | 8 | 4 | 2 | tr | tr |

ND = not detected
tr = trace amount

TABLE 4

Theobroma and Herrania Species Procyanidin Levels
ppm (μg/g) in defatted powder
Oligomer

| SAMPLE | Monomer | Dimer | Trimer | Tetramer | Pentamer | Hexamer | Heptamer | Octamer | Nonamer | Decamer | Undecamer | Total |
|---|---|---|---|---|---|---|---|---|---|---|---|---|
| T. grandiflorum x T. obovaum 1[1] | 3822 | 3442 | 5384 | 4074 | 3146 | 2080 | 850 | 421 | 348 | 198 | tr+ | 23,765 |
| T. grandiflorum x T. obovaum 2[1] | 3003 | 4098 | 5411 | 3983 | 3931 | 1914 | 1090 | 577 | 356 | 198 | tr | 23,561 |
| T. grandiflorum x T. obovaum 3A[1] | 4990 | 4980 | 7556 | 5341 | 4008 | 2576 | 1075 | 598 | 301 | 144 | tr | 31,569 |
| T. grandiflorum x T. obovaum 3B[1] | 3880 | 4498 | 6488 | 4930 | 3706 | 2560 | 1208 | 593 | 323 | 174 | tr | 28,360 |
| T. grandiflorum x T. obovaum 4[1] | 2647 | 3591 | 5328 | 4240 | 3304 | 2380 | 1506 | 815 | 506 | 249 | tr | 24,566 |
| T. grandiflorum x T. obovaum 6[1] | 2754 | 3855 | 5299 | 3872 | 2994 | 1990 | 1158 | 629 | 356 | 196 | 88 | 23,194 |
| T. grandiflorum x T. oboratum SIN[1] | 3212 | 4134 | 7608 | 4736 | 3590 | 2274 | 936 | 446 | 278 | 126 | ND* | 23,750 |
| T. obovatum 1[1] | 3662 | 5683 | 9512 | 5358 | 3858 | 2454 | 1207 | 640 | 302 | 144 | ND | 32,820 |

TABLE 4-continued

Theobroma and Herrania Species Procyanidin Levels
ppm (μg/g) in defatted powder

| SAMPLE | Monomer | Dimer | Trimer | Tetramer | Pentamer | Hexamer | Oligomer Heptamer | Octamer | Nonamer | Decamer | Undecamer | Total |
|---|---|---|---|---|---|---|---|---|---|---|---|---|
| T. grandiflorum TEFFE[2] | 2608 | 2178 | 3090 | 2704 | 2241 | 1586 | 900 | 484 | 301 | 148 | tr | 16,240 |
| T. grandiflorum TEFFE x T. grandiflorum[2] | 4773 | 4096 | 5289 | 4748 | 3804 | 2444 | 998 | 737 | 335 | 156 | tr | 27,380 |
| T. grandiflorum x T. subincanum[1] | 4752 | 3336 | 4916 | 3900 | 3064 | 2039 | 782 | 435 | 380 | 228 | ND | 23,832 |
| T. obovatum x T. subincanum[1] | 3379 | 3802 | 5836 | 3940 | 2868 | 1807 | 814 | 427 | 271 | 136 | tr | 23,280 |
| T. speciosum x T. sylvestris[1] | 902 | 346 | 1350 | 217 | 152 | 120 | 60 | tr | tr | ND | ND | 3,147 |
| T. microcarpum[2] | 5694 | 3250 | 2766 | 1490 | 822 | 356 | 141 | tr | ND | ND | ND | 14,519 |
| T. cacao, SIAL 659, t0 | 21,929 | 10,072 | 10,106 | 7788 | 5311 | 3242 | 1311 | 626 | 422 | 146 | tr | 60,753 |
| T. cacao, SIAL 659, t24 | 21,088 | 9762 | 9119 | 7094 | 4774 | 2906 | 1364 | 608 | 361 | 176 | tr | 57,252 |
| T. cacao, SIAL 659, t48 | 20,887 | 9892 | 9474 | 7337 | 4906 | 2929 | 1334 | 692 | 412 | 302 | tr | 58,165 |
| T. cacao, SIAL 659, t96 | 9552 | 5780 | 5062 | 3360 | 2140 | 1160 | 464 | 254 | 138 | tr | ND | 27,910 |
| T. cacao, SIAL 659, t120 | 8581 | 4665 | 4070 | 2527 | 1628 | 888 | 326 | 166 | 123 | tr | ND | 22,974 |
| Pod Rec. 10/96, Herrania mariae | 869 | 1295 | 545 | 347 | 175 | 97 | tr | *ND | ND | | | 33329 |
| Sample Rec. prior to 10/96, Herrania mariae | 130 | 354 | 151 | 131 | 116 | 51 | tr | ND | ND | | | 933 |

*ND = none detected
[1]sample designated CPATU  tr = trace (<50 μg/g)
[2]sample designated ERJON

Example 7

Effect of Procyanidins on NO

Method A.

The purpose of this study was to establish the relationship between procyanidins and NO, which is known to induce cerebral vascular dilation. The effects of monomers and higher oligomers, in concentrations ranging from 100 μg/mL to 0.1 μg/mL, on the production of nitrates (the catabolites of NO), from HUVEC (Human umbilical vein endothelial cells) is evaluated. HUVEC (from Clonetics) is investigated in the presence or absence of each procyanidin for 24 to 48 hours. At the end of the experiments, the supernatants are collected and the nitrate content determined by calorimetric assay. In separate experiments, HUVEC is incubated with acetylcholine, which is known to induce NO production, in the presence or absence of procyanidins for 24 to 48 hours. At the end of the experiments, the supernatants are collected and nitrate content is determined by calorimetric assay. The role of NO is ascertained by the addition of nitroarginine or (1)-N-methyl arginine, which are specific blockers of NO synthase.

Method B. Vasorelaxation of Phenylephrine-Induced Contracted Rat Artery

Figure 7:
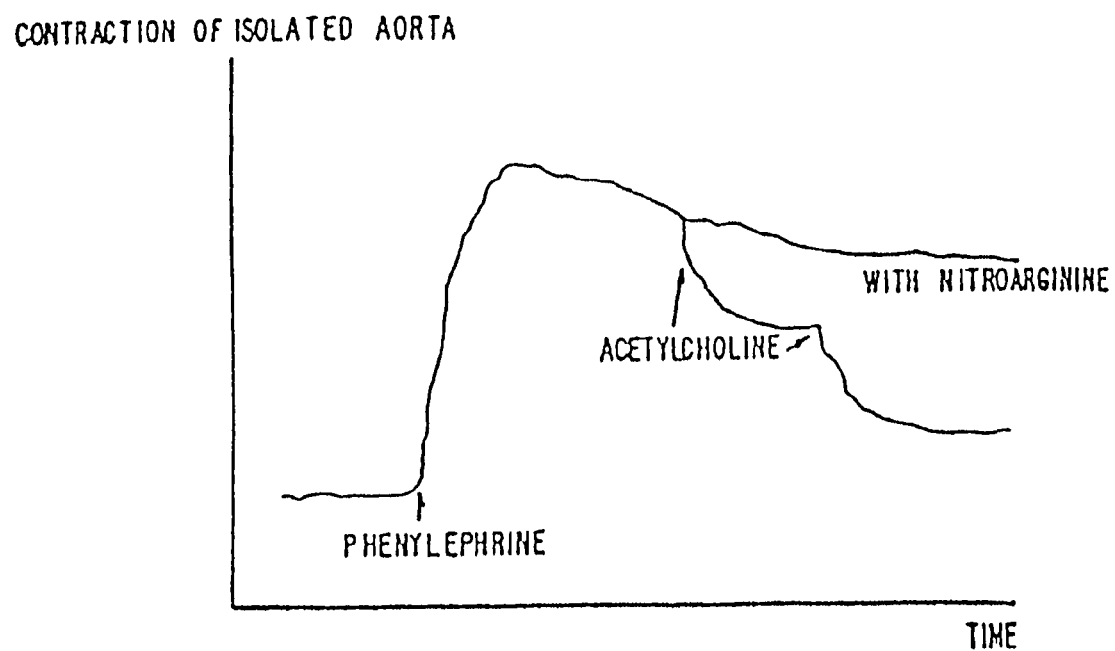
FIG. 7 shows the acetylcholine-induced relaxation of NO-related phenylephrine-precontracted rat aorta.

The effects of each of the procyanidins (100 μg/mL to 0.1 μg/mL) on the rat artery is the target for study of vasorelaxation of phenylephrine-induced contracted rat artery. Isolated rat artery is incubated in the presence or absence of procyanidins and alteration of the muscular tone is assessed by visual inspection. Both contraction or relaxation of the ray artery is determined. Then, using other organs, precontraction of the isolated rat artery is induced upon addition of epinephrine. Once the contraction is stabilized, procyanidins are added and contraction or relaxation of the rat artery is determined. The role of NO is ascertained by the addition of nitroarginine or (1)-N-methyl arginine. The acetylcholine-induced relaxation of NO-related phenylephrine-precontracted rat aorta is shown in FIG. 7.

Method C. Induction of Hypotension in the Rat

This method is directed to the effect of each procyanidin on blood pressure. Rats are instrumented in order to monitor systolic and diastolic blood pressure. Each of the procyanidins are injected intravenously (dosage range=100–0.1 μg/kg), and alteration of blood pressure is assessed. In addition, the effect of each procyanidin on the alteration of blood pressure evoked by epinephrine is determined. The role of NO is ascertained by the addition of nitroarginine or (1)-N-methyl arginine.

These studies illustrate that the cocoa procyanidins are useful in modulating vasodilation, and are further useful with respect to modulating blood pressure or addressing coronary conditions, and migraine headache conditions.

Example 8

NO Dependent Hypotension In The Guinea Pig

The effect of five cocoa procyanidin fractions on guinea pig blood pressure were investigated. Briefly, guinea pigs (approximately 400 g body weight; male and female) were anesthetized upon injection of 40 mg/kg sodium pentobarbital. The carotid artery was cannulated for monitoring of the arterial blood pressure. Each of the five cocoa procyanidin fractions was injected intravenously (dose range 0.1 mg/kg–100 mg/kg) through the jugular vein. Alterations of blood pressure were recorded on a polygraph. In these experiments, the role of NO was ascertained by the administration of L-N-methylarginine (1 mg/kg) ten minutes prior to the administration of cocoa procyanidin fractions.

Cocoa procyanidin fractions were prepared and analyzed according to the procedures described in U.S. Pat. No. 5,554,645, hereby incorporated herein by reference.

Fraction A: Represents a preparative HPLC fraction comprised of monomers-tetramers. HPLC analysis revealed the following composition:

| | |
|---|---|
| Monomers | 47.2% |
| Dimers | 23.7 |
| Trimers | 18.7 |
| Tetramers | 10.3 |

Fraction B: Represents a preparative HPLC fraction comprised of pentamers-decamers. HPLC analysis revealed the following composition:

| | |
|---|---|
| Pentamers | 64.3% |
| Hexamers | 21.4 |
| Heptamers | 7.4 |
| Octamers | 1.9 |
| Nonamers | 0.9 |
| Decamers | 0.2 |

Fraction C: Represents an enriched cocoa procyanidin fraction used in the preparation of Fractions A and B (above). HPLC analysis revealed the following composition:

| | |
|---|---|
| Monomers | 34.3% |
| Dimers | 17.6 |
| Trimers | 16.2 |
| Tetramers | 12.6 |
| Pentamers | 8.5 |
| Hexamers | 5.2 |
| Heptamers | 3.1 |
| Octamers | 1.4 |
| Nonamers | 0.7 |
| Decamers | 0.3 |

Fraction D: Represents a procyanidin extract prepared from a milk chocolate. HPLC analysis revealed a composition similar to that listed in the Table 4 for Brand 8. Additionally, caffeine 10% and theobromine 6.3% were present.

Fraction E: Represents a procyanidin extract prepared from a dark chocolate prepared with alkalized liquor. HPLC analysis revealed a composition similar to that listed in the Table 4 for Brand 12. Additionally, caffeine 16.0% and theobromine 5.8% were present.

In three separate experiments, the effects of administering 10 mg/kg cocoa procyanidin fractions on arterial blood pressure of anesthetized guinea pigs was investigated. Upon intravenous injection, procyanidin fractions A and E evoked a decrease in blood pressure of about 20%. This decrease was only marginally different from that obtained from a solvent (DMSO) control (15±5%, n=5). In contrast, procyanidin fractions B, C and D (10 mg/kg) induced marked decreases in blood pressure, up to 50–60% for C. In these experiments the order of hypotensive effect was as follows: C>B>D>>A=E.

Figure 8A:
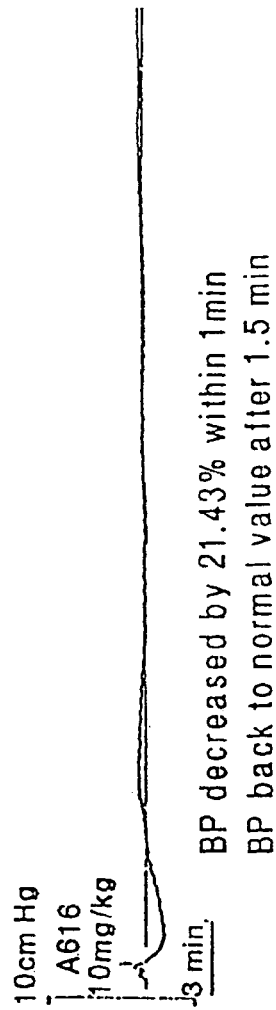
FIGS. 8A and B show the effects of cocoa procyanidin fraction A and C, respectively, on blood pressure; blood pressure levels decreased by 21.43% within 1 minute after administration of fraction A, and returned to normal after 15 minutes, while blood pressure decreased by 50.5% within 1 minute after administration of fraction C, and returned to normal after 5 minutes.
Figure 8B:
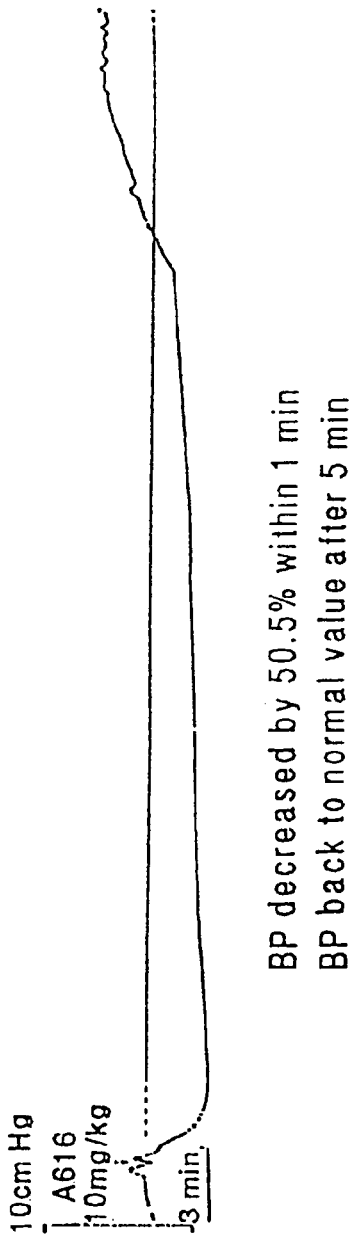
Figure 9:
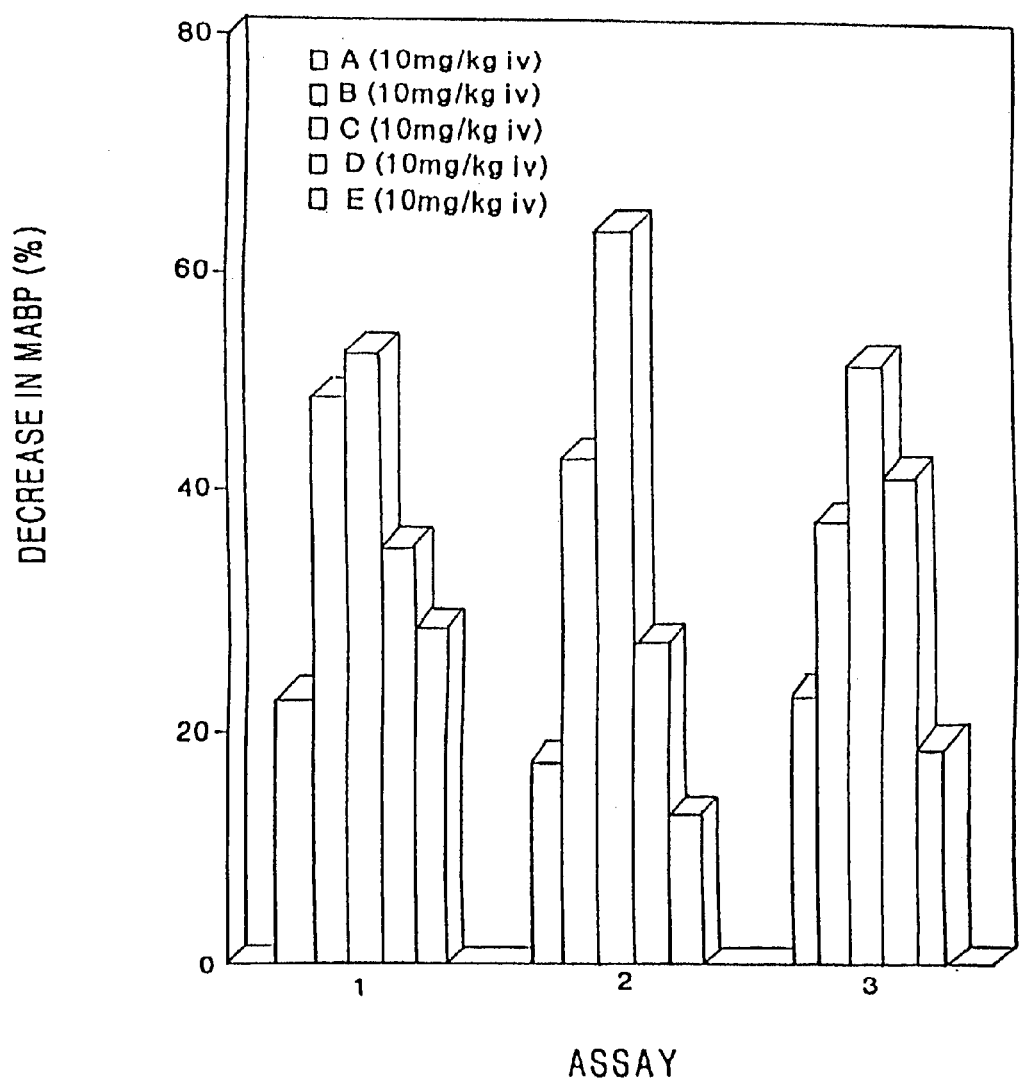
FIG. 9 shows the effect of cocoa procyanidin fractions on arterial blood pressure in anesthetized guinea pigs.

Typical recordings of blood pressure elicited after injection of procyanidin fractions appear in FIG. 8A for fraction A and FIG. 8B for fraction C. FIG. 9 illustrates the comparative effects on blood pressure by these fractions.

Figure 10:
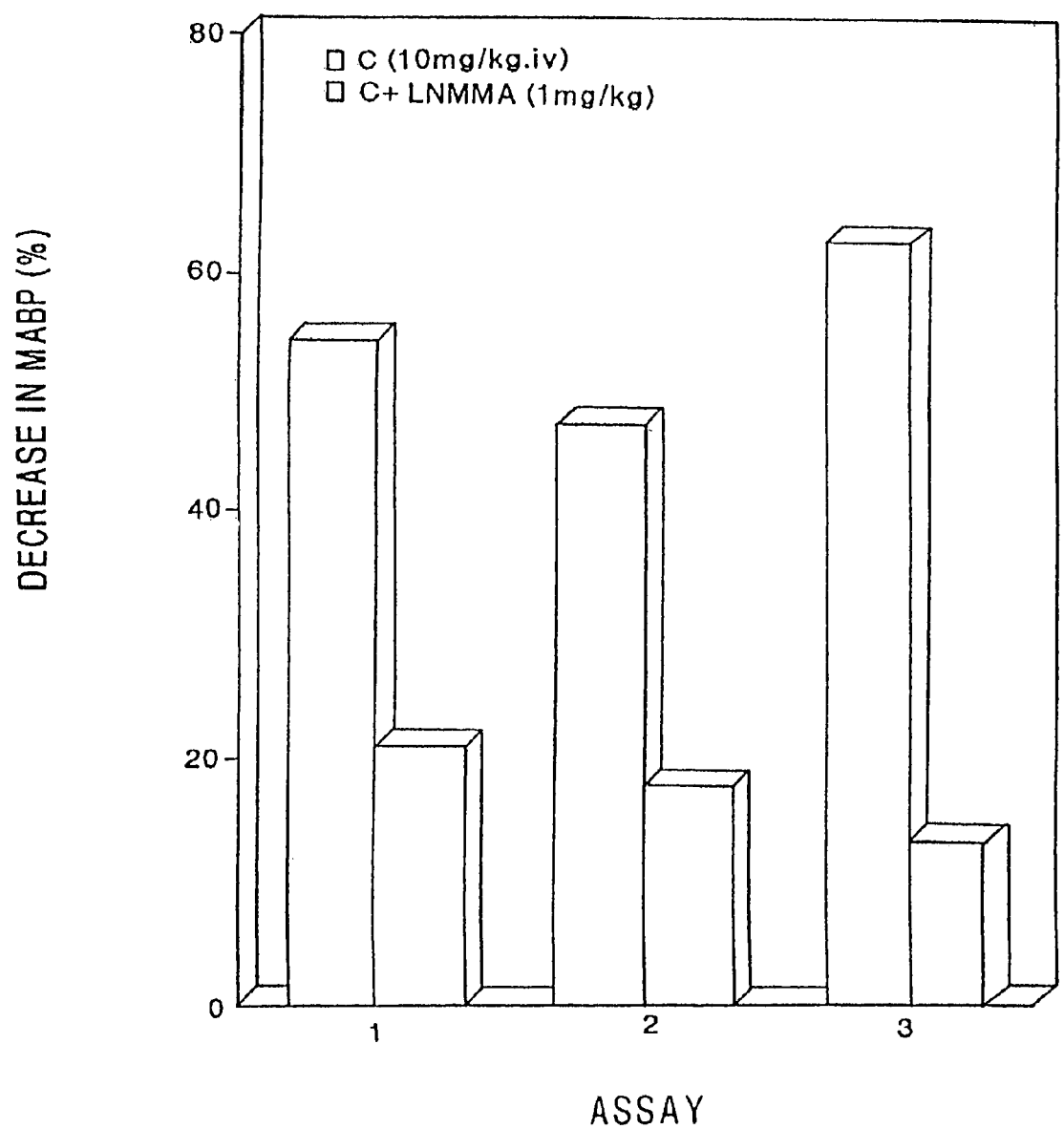
FIG. 10 shows the effect of L-NMMA on the alterations of arterial blood pressure in anesthetized guinea pigs induced by cocoa procyanidin fraction C.

The possible contribution of NO in the hypotension in the guinea pig induced by administration of fraction C was analyzed using L-N-methyl arginine (LNMMA). This pharmacological agent inhibits the formation of NO by inhibiting NO synthase. L-NMMA was administered at the dose of 1 mg/kg, ten minutes prior to injection of the cocoa procyanidin fractions. As shown in FIG. 10, treatment of the animals with L-NMMA completely blocked the hypotension evoked by the procyanidin fraction C. Indeed, following treatment with this inhibitor, the alterations of blood pressure produced by fraction C were similar to those noted with solvent alone.

Example 9

Effect of Cocoa Procyanidin Fractions on NO Production in Human Umbilical Vein Endothelial Cells Human umbilical vein endothelial cells (HUVEC) were obtained from Clonetics and cultures were carried out according to the manufacturer's specifications. HUVEC cells were seeded at 5,000 cells/cm$^2$ in 12-well plates (Falcon). After the third passage under the same conditions, they were allowed to reach confluence. The supernatant was renewed with fresh medium containing defined concentrations of bradykinin (25, 50 and 100 nM) or cocoa procyanidin fractions A–E (100 µg/mL) as described in Example 3. The culture was continued for 24 hr. and the cell free supernatants were collected and stored frozen prior to assessment of NO content as described below. In selected experiments, the NO synthase (NOS) antagonist, Nonitro-L-arginine methyl ester (L-NAME, 10 µM) was added to assess the involvement of NOS in the observed NO production.

HUVEC NO production was estimated by measuring nitrite concentration in the culture supernatant by the Griess reaction. Griess reagent was 1% sulfanilamide, 0.1% N-(1-naphthyl)-ethylenediamine dihydrochloride. Briefly, 50 µL aliquots were removed from the various supernatants in quadruplicate and incubated with 150 µL of the Griess reagent. The absorbency at 540 nm was determined in a multiscan (Labsystems Multiskans MCC/340) apparatus. Sodium nitrite was used at defined concentrations to establish standard curves. The absorbency of the medium without cells (blank) was subtracted from the value obtained with the cell containing supernatants.

Figure 11:
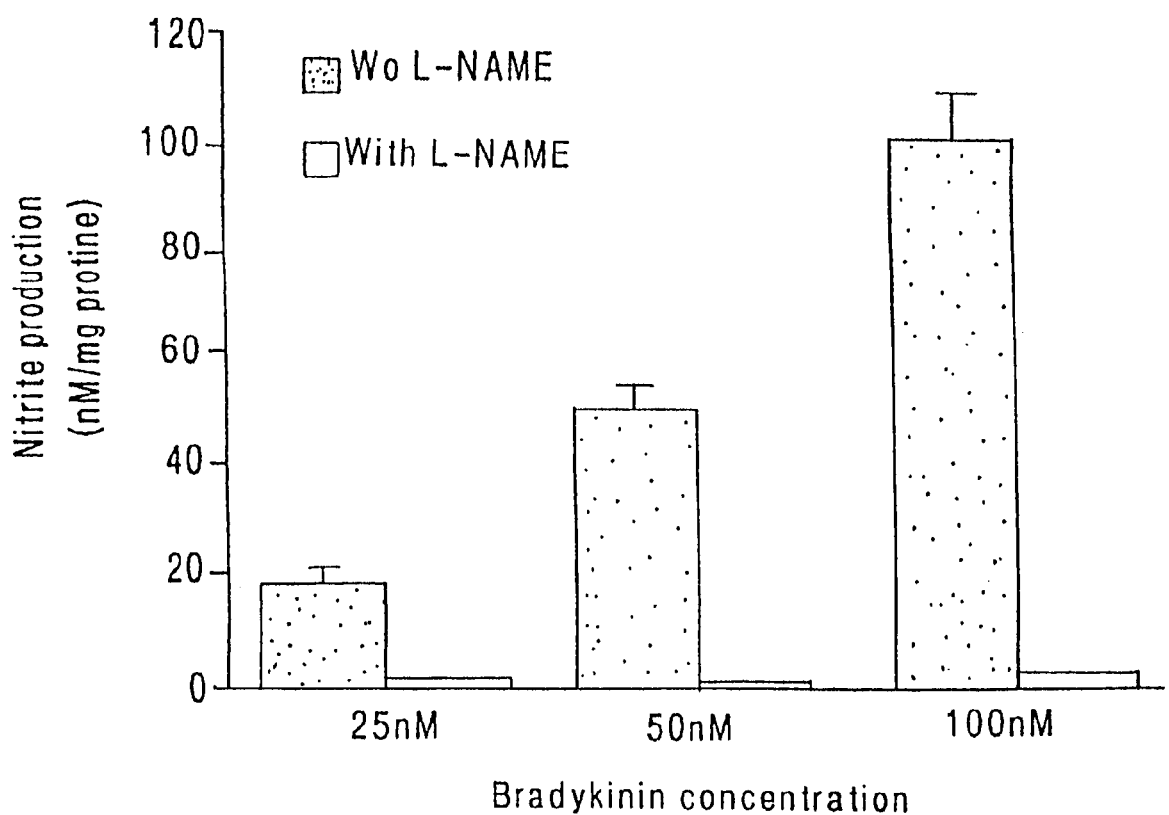
FIG. 11 shows the effect of bradykinin on NO production by HUVEC.

FIG. 11 illustrates the effect of bradykinin on NO production by HUVEC where a dose dependent release of NO was observed. The inhibitor L-NAME completely inhibited the bradykinin induced NO release.

FIG. 12 illustrates the effect of the cocoa procyanidin fractions on NO production by HUVEC cells. Fractions B, C and D induced a moderate but significant amount of NO production by HUVEC. By far, Fraction C was the most efficient fraction to induce NO formation as assessed by the production of nitrites, while Fraction E was nearly ineffective. The effect of Fraction C on NO production was dramatically reduced in the presence of L-NAME. Interestingly, Fractions B, C and D contained higher amounts of procyanidin oligomers than Fractions A and E. A distinguishing difference between Fractions D and E was that E was prepared from a dark chocolate which used alkalized cocoa liquor as part of the chocolate recipe. Alkalization leads to a base catalyzed polymerization of procyanidins which rapidly depletes the levels of these compounds. An analytical comparison of procyanidin levels found in these types of chocolate appear in the Table 4, where Brand 12 is a dark chocolate prepared with alkalized cocoa liquor and Brand 11 is a typical milk chocolate. Thus, extracts obtained from milk chocolates contain high proportions of procyanidin oligomers which are capable of inducing NO. The addition of the NO inhibitor L-NMMA to the Fraction C sample clearly led to the inhibition of NO. The results obtained from the procyanidin fractions were consistent to those observed with the bradykinin induced NO experiment (see FIG. 11).

As in the case of the HUVEC results, cocoa procyanidin fraction C elicited a major hypotensive effect in guinea pigs, whereas fractions A and E were the least effective. Again, the presence of high molecular weight procyanidin oligomers were implicated in the modulation of NO production.

Example 10

Effect of Cocoa Procyanidin Fractions on Macrophage NO Production

Fresh, human heparinized blood (70 mL) was added with an equal volume of phosphate buffer saline (PBS) at room temperature. A Ficoll-Hypaque solution was layered underneath the blood-PBS mixture using a 3 mL Ficoll-Hypaque to 10 mL blood-PBS dilution ratio. The tubes were centrifuged for 30 minutes at 2,000 rpm at 18–20° C. The upper layer containing plasma and platelets was discarded. The mononuclear cell layer was transferred to another centrifuge tube and the cells were washed 2×in Hanks Balanced Saline Solution. The mononuclear cells were resuspended in complete RPMI 1640 supplemented with 10% fetal calf serum, counted, and the viability determined by the Trypan Blue exclusion method. The cell pellet was resuspended in complete RPMI 1640 supplemented with 20% fetal calf serum to a final concentration of $1\times10^6$ cells/mL. Aliquots of the cell suspension were plated into a 96 well culture plate and rinsed 3× with RPMI 1640 supplemented with 10% fetal calf serum and the nonadherent cells (lymphocytes) were discarded.

These cells were incubated for 48 hours in the presence or absence of five procyanidin fractions described in Example 3. At the end of the incubation period, the culture media were collected, centrifuged and cell free supernatants were stored frozen for nitrate assay determinations.

Macrophage NO production was determined by measuring nitrite concentrations by the Greiss reaction. Greiss reagent was 1% sulfanilamide, 0.1% N-(1-naphthyl)-ethylenediamine dihydrochloride. Briefly, 50 µL aliquots were removed from the supernatants in quadruplicate and incubated with 150 µL of the Greiss reagent. The absorbency at 540 nm was determined in a multiscan (Labsystems Multiskans MCC/340) apparatus. Sodium nitrite was used at defined concentrations to establish standard curves. The absorbency of the medium without cells (blank) was subtracted from the value obtained with the cell containing supernatants.

In a separate experiment, macrophages were primed for 12 hours in the presence of 5 U/mL gamma-interferon and then stimulated with 10 µg/mL LPS for the next 36 hours in the presence or absence of 100 µg/mL of the five procyanidin fractions.

FIG. 13 indicates that only procyanidin fraction C, at 100 µg/mL, could induce NO production by monocytes/macrophages. Basal NO production by these cells was undetectable and no nitrite could be detected in any of the cocoa procyanidin fractions used at 100 µg/mL. FIG. 14 indicates that procyanidin fractions A and D enhanced LPS-induced NO production by γ-interferon primed monocytes/macrophages. Procyanidin fraction C was marginally effective, since LPS-stimulated monocytes/macrophages cultured in the absence of procyanidin fractions produced only 4 µmole/$10^5$ cells/48 hours. γ-Interferon alone was ineffective in inducing NO.

Collectively, these results demonstrate that mixtures of the cocoa procyanidins used at specific concentrations are capable of inducing monocyte/macrophage NO production both independent and dependent of stimulation by LPS or cytokines.

Example 11

The Effect of Cocoa Procyanidins on Lipoxygenase Activity

The specific hypothesis which was tested in this part of the work was that polyphenolic cocoa extracts inhibit the activity of lipoxygenase in a dose-dependent and component specific manner.

Lipoxygenase Type I-B from soybean, linoleic acid (approx. 99%), Tween 20 (Polyoxyethylene-sorbitan monolaurate), and control phenols: Nordihydroguaiaretic acid (NDGA), (+)-catechin and (−)-epicatechin were obtained from Sigma Chemical. The cocoa polypenolics functions which were tested included defined phenol fractions (monomer to hexamer) and extracts (crude acetone and pentamer enriched).

Linoleic acid was solubilized using the emulsifier Tween 20 according to the method of Grossman & Zakut (Methods Biochem. Anal. 25:303–329, 1979). Briefly, linoleic acid was dissolved in absolute ethanol (70 mg/7 mL) and Tween 20 (250 µL) was added. The ethanol was evaporated from the solution in the dark under vacuum. The residue was resuspended in 50 mL PBS and the pH adjusted to 8.0 to result in a clear solution containing linoleic acid (5 mM) and Tween 20 (0.5% vol.).

Lipoxygenase was dissolved in PBS pH 8.6 at 5000 U/mL. Cocoa phenols were dissolved in pure water and diluted from the following stock solutions. 1 to 6mer were dissolved at 1 mM, extracts at 1 mg/mL (1 g crude acetone extract/L~3.0 mM monomer, 1 g 5mer enriched extract/L~3.4 mM).

Reaction mixtures contained dissolved linoleic acid (100 µM) in PBS pH 7.4 plus/minus test phenols in water. The reaction was initiated by adding lipoxygenase for a final concentration of 100 U/mL. Conjugated diene measurement of hydroperoxide formation of linoleic acid was measured by recording kinetic scans over 5 or 10 minutes on a Beckman DU-600 UV spectrophotometer (at 37° C., absorbance 234 nm). Inhibition was calculated for each sample set of 6 reaction cuvettes (1 control with water, 5 experimental with phenol in water):

% Inhibition=($\Delta$abs. control−$\Delta$abs. experimental)/$\Delta$abs. control)×100

The high UV absorbance of the cocoa components did not allow the measurement of $IC_{50}$ at actual concentrations. For this reason an $IC_{50}$ value was calculated by extrapolating the logarithmic regression curve (% inhibition over log phenol concentration) to the concentration at which 50% inhibition of lipoxygenase activity was achieved by the test substance. Extrapolated $IC_{50}$ values give a rough approximation of the lipoxygenase inhibitory activity of cocoa polyphenol extracts.

Results

NDGA is an established inhibitor of soybean and several mammalian lipoxygenases (Kemal et al, Biochemistry 26:7064–7072, 1987). It is commercially used as an antioxidant in fats and oils. NDGA serves as a positive control since the $IC_{50}$ value of $2\times10^{-6}$ M was not reached by other test phenols. (+)-catechin and (−) epicatechin are assumed to be structurally similar to the cocoa polyphenol monomer.

Phenols were compared on a molar basis. Lipoxygenase inhibition by (+)-catechin ($3\times10^{-3}$M) was two magnitudes stronger than by (−)-epicatechin ($3\times10^{-1}$ M) and very similar to inhibition by +cocoa monomer ($5\times10^{-3}$M), dimer ($2\times10^{-3}$M) and trimer ($2\times10^{-3}$M). Lipoxygenase inhibition by the higher oligomers correlated less well with the log of the molar concentration. At final concentrations of 0.3 to 25 µM, the tetramer, pentamer and hexamer inhibited 5–30% lipoxygenase activity. However, phenol concentration and inhibition did not correlate significantly. The crude acetone extract exhibited a concentration dependent lipoxygenase inhibition ($IC_{50}$=5 µM, compared on a monomer basis) approximately 3 magnitudes weaker than monomer to trimer fractions. The pentamer enriched extract ($IC_{50}$=59M) could not be said to inhibit lipoxygenase activity at a meaningful level.

The soybean lipoxygenase inhibitory activity of cocoa phenol extracts resemble that of (+)-catechin. There is little difference among the activities of the monomer to trimer if compared on a molar basis, suggesting a steric inhibition of the enzyme. The inhibition may be specific for the low molecular weight components (monomer to trimer) since the tetramer to hexamer compounds show considerably less lipoxygenase inhibitory activity and the pentamer enriched extract is less inhibiting than the crude extract, which contains more of the monomer to trimer oligomeric fractions. Given the above results, we suggest that cocoa polyphenols may inhibit soybean lipoxygenase either by chelating the prosthetic iron ion, or by scavenging free radicals via phenolic hydroxyl groups in the oxidation reaction, which includes free radical intermediates. Larger oligomers (the tetramers to hexamers) may be sterically hindered and thus may not be capable of reading the catalytic site of the enzyme.

Example 12

The Effect of Cocoa Procyanidins on Cyclo-oxygenase 1 & 2

The effect of procyanidins on cyclo-oxygenase 1 & 2 (COX-1/COX-2) activities was assessed by incubating the enzymes (derived from ram seminal vesicle and sheep placenta, respectively), with arachidonic acid (5 µM) for 10 minutes at room temperature, in the presence of varying concentrations of procyanidin solutions containing monomers to decamers and containing a procyanidin mixture. Turnover was assessed by using PGE2 EIA kits from Interchim (France). Indomethacin was used as a reference compound. The results are presented in the following Table, wherein the $IC_{50}$ values are expressed in units of µM (except for Sample 11, which represents a procyanidin mixture) and where the samples S1 to S10 represent procyanidin oligomers (monomer through decamer), and $IC_{50}$ is expressed in units of mg/mL.

| SAMPLE # | $IC_{50}$COX-1* | $IC_{50}$COX-2* | RATION $IC_{50}$ COX-2/COX-1 |
|---|---|---|---|
| 1 | 0.074 | 0.197 | 2.66 |
| 2 | 0.115 | 0.444 | 3.86 |
| 3 | 0.258 | 0.763 | 2.96 |
| 4 | 0.154 | 3.73 | 24.22 |
| 5 | 0.787 | 3.16 | 4.02 |
| 6 | 1.14 | 1.99 | 1.75 |
| 7 | 1.89 | 4.06 | 2.15 |
| 8 | 2.25 | 7.2 | 3.20 |
| 9 | 2.58 | 2.08 | 0.81 |
| 10 | 3.65 | 3.16 | 0.87 |
| 11 | 0.0487 | 0.0741 | 1.52 |
| Indomethacin | 0.599 | 13.5 | 22.54 |

*expressed as µM with exception of Sample 11, which is mg/mL.

Figure 15A:
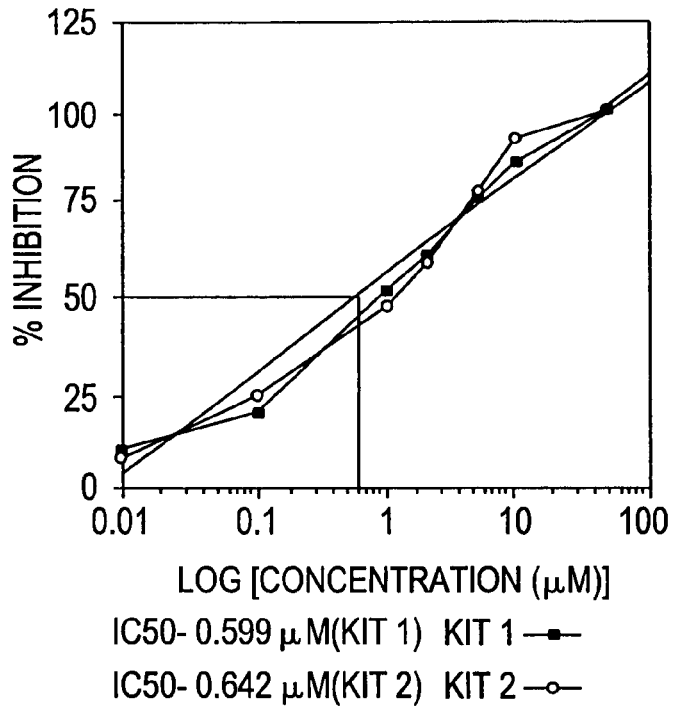
FIGS. 15A & B show the effects of indomethacin on COX-1 and COX-2 activities.
Figure 15B:
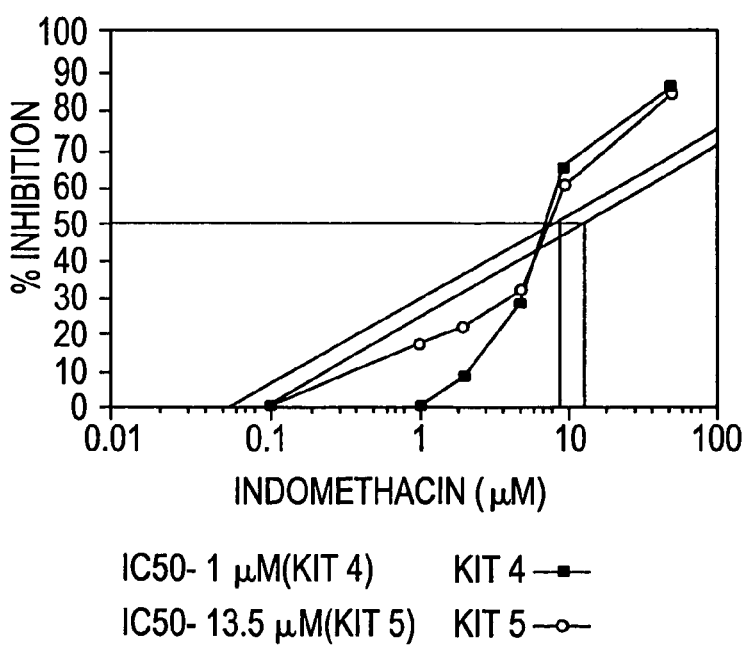
Figure 16A:
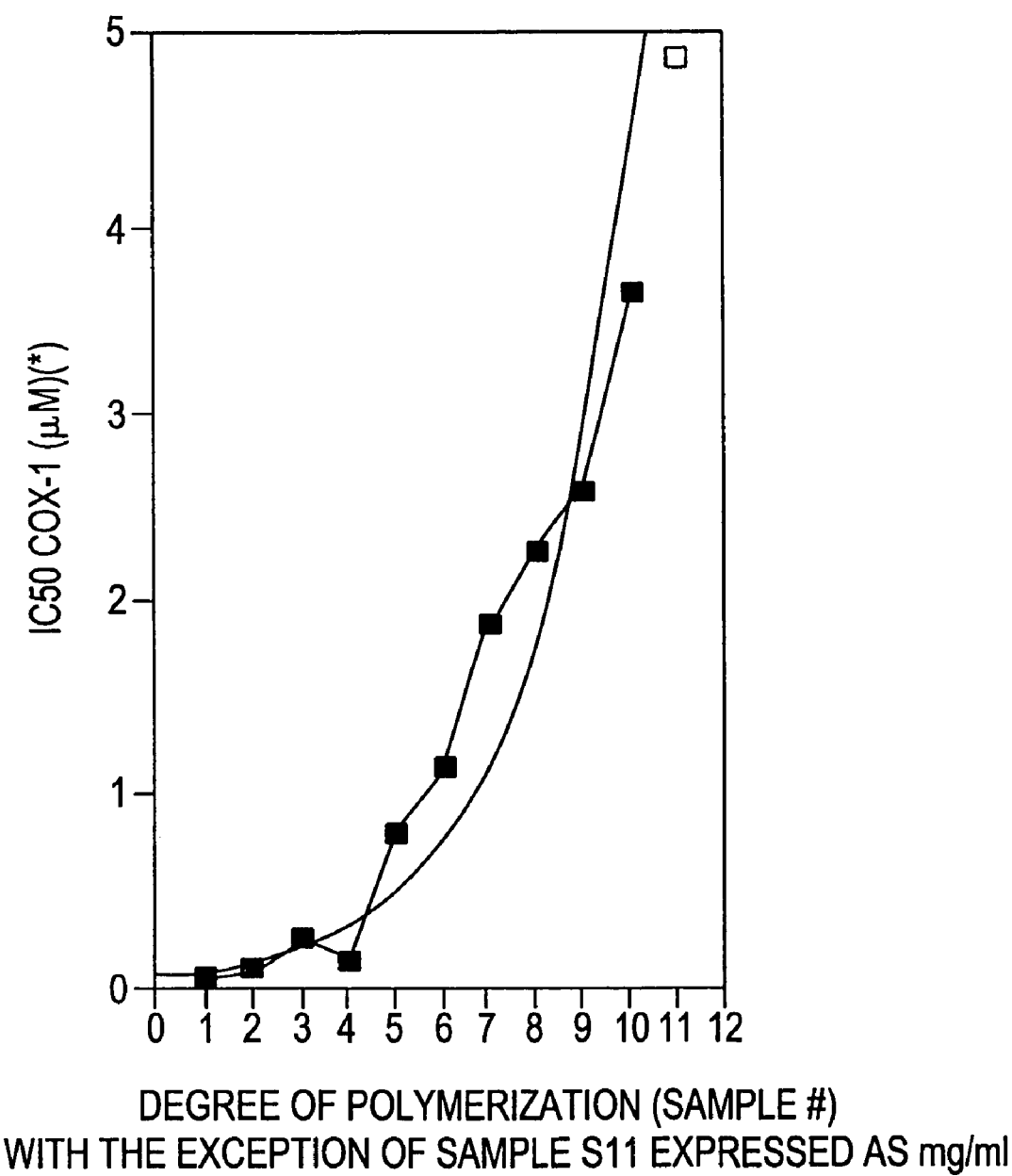
FIGS. 16A & B show the correlation between the degree of polymerization and $IC_{50}$ vs. COX1/COX2 (µM)
Figure 16B:
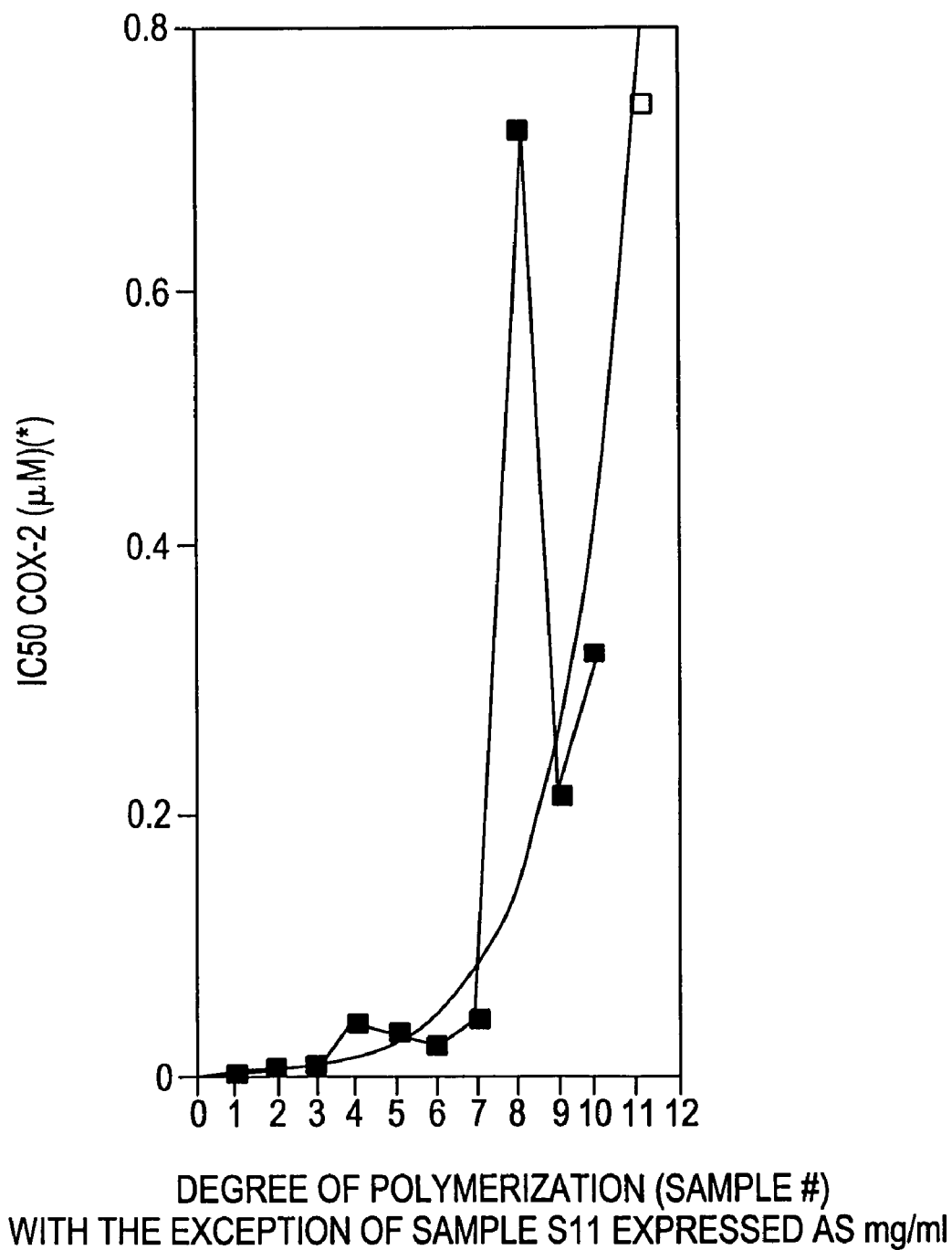
Figure 17:
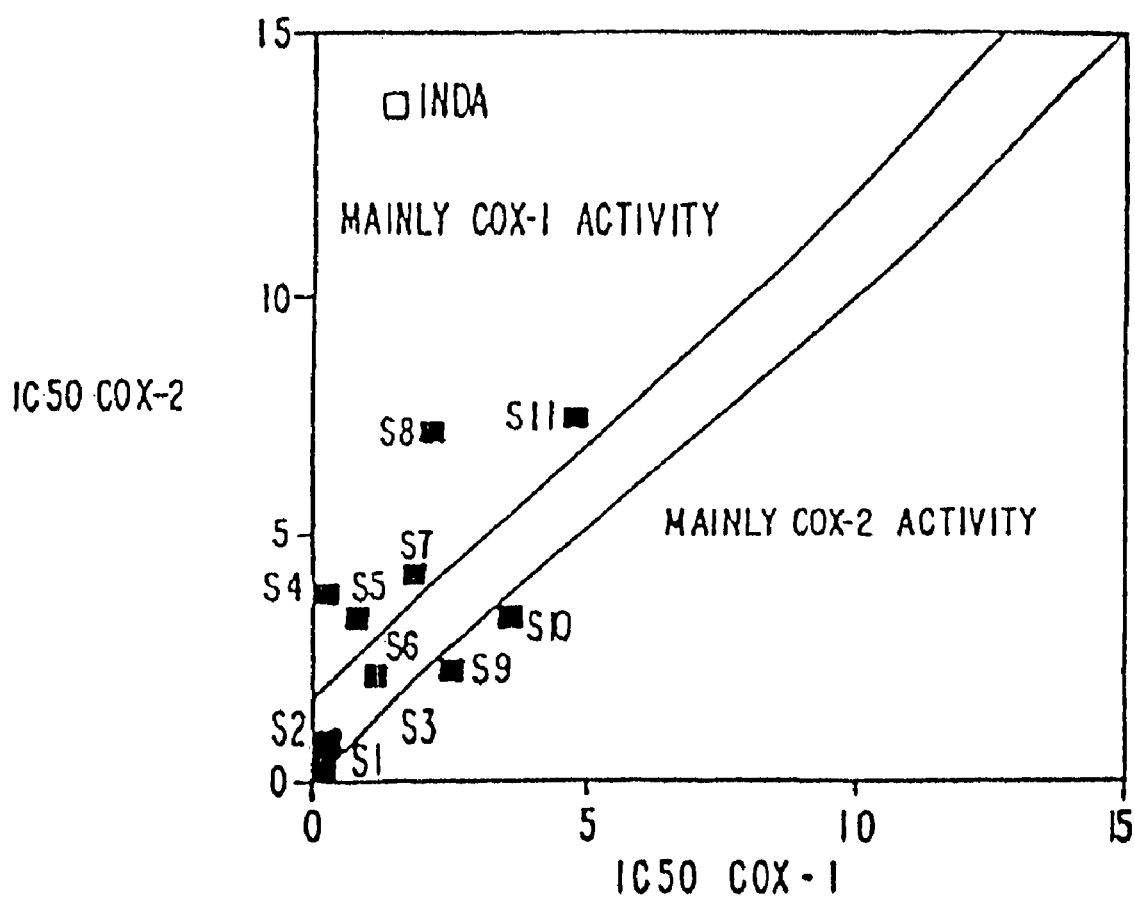
FIG. 17 shows the correlation between the effects of compounds on COX-1 and COX-2 activities expressed as µM.
Figure 18A:
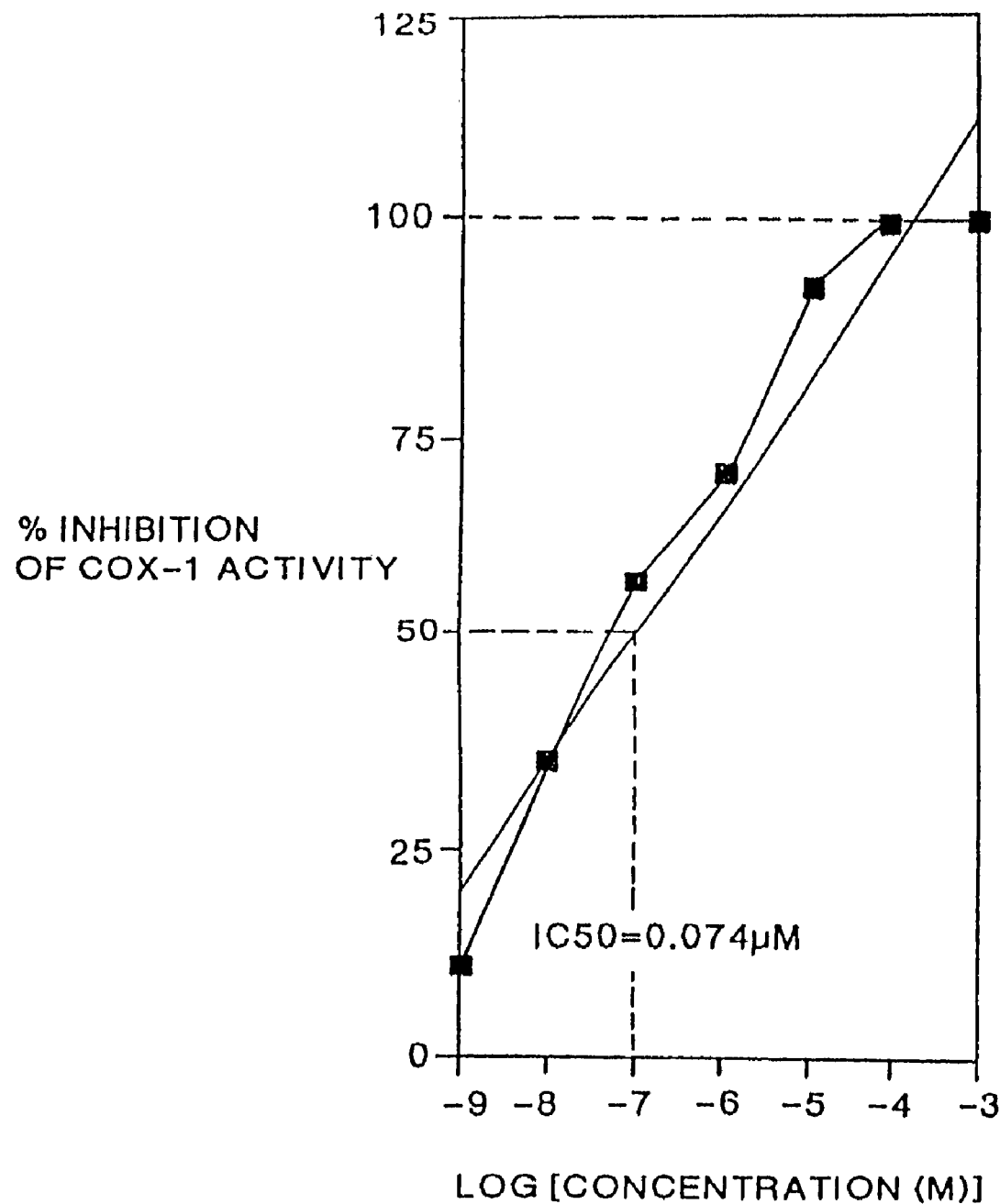
FIG. 18A–V show the $IC_{50}$ values (µM) of samples containing procyanidins with COX-1/COX-2.
Figure 18B:
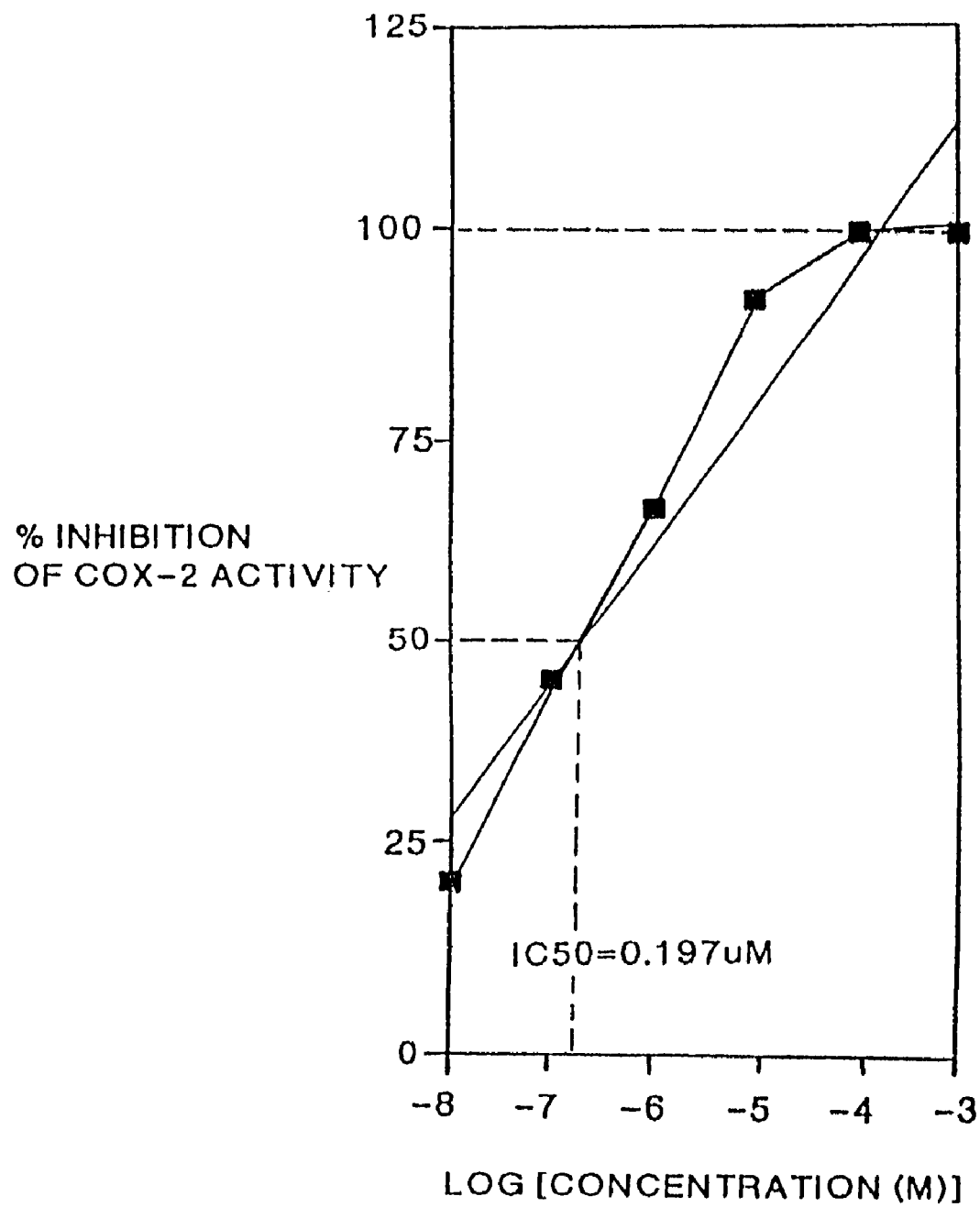
Figure 18C:
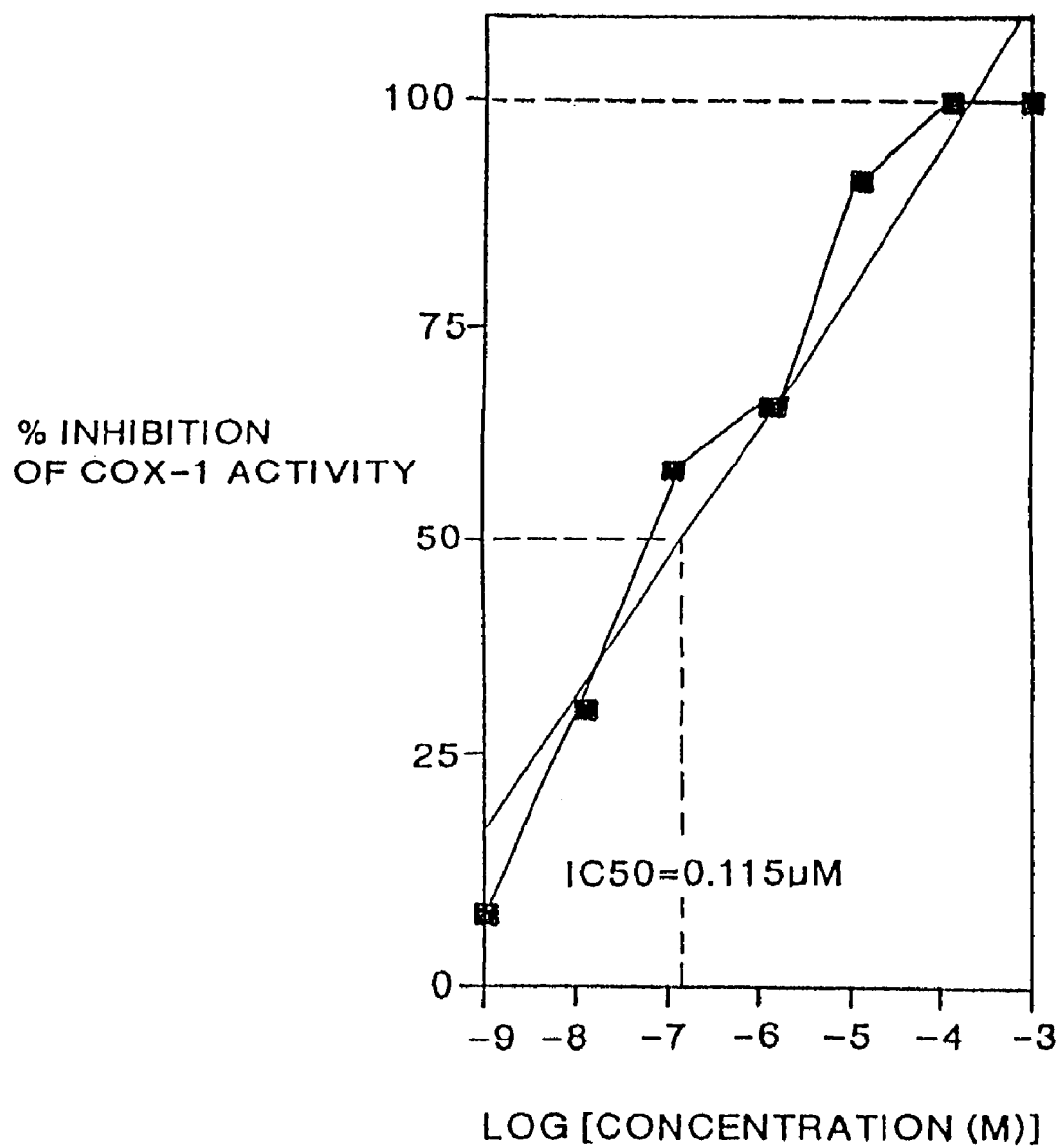
Figure 18D:
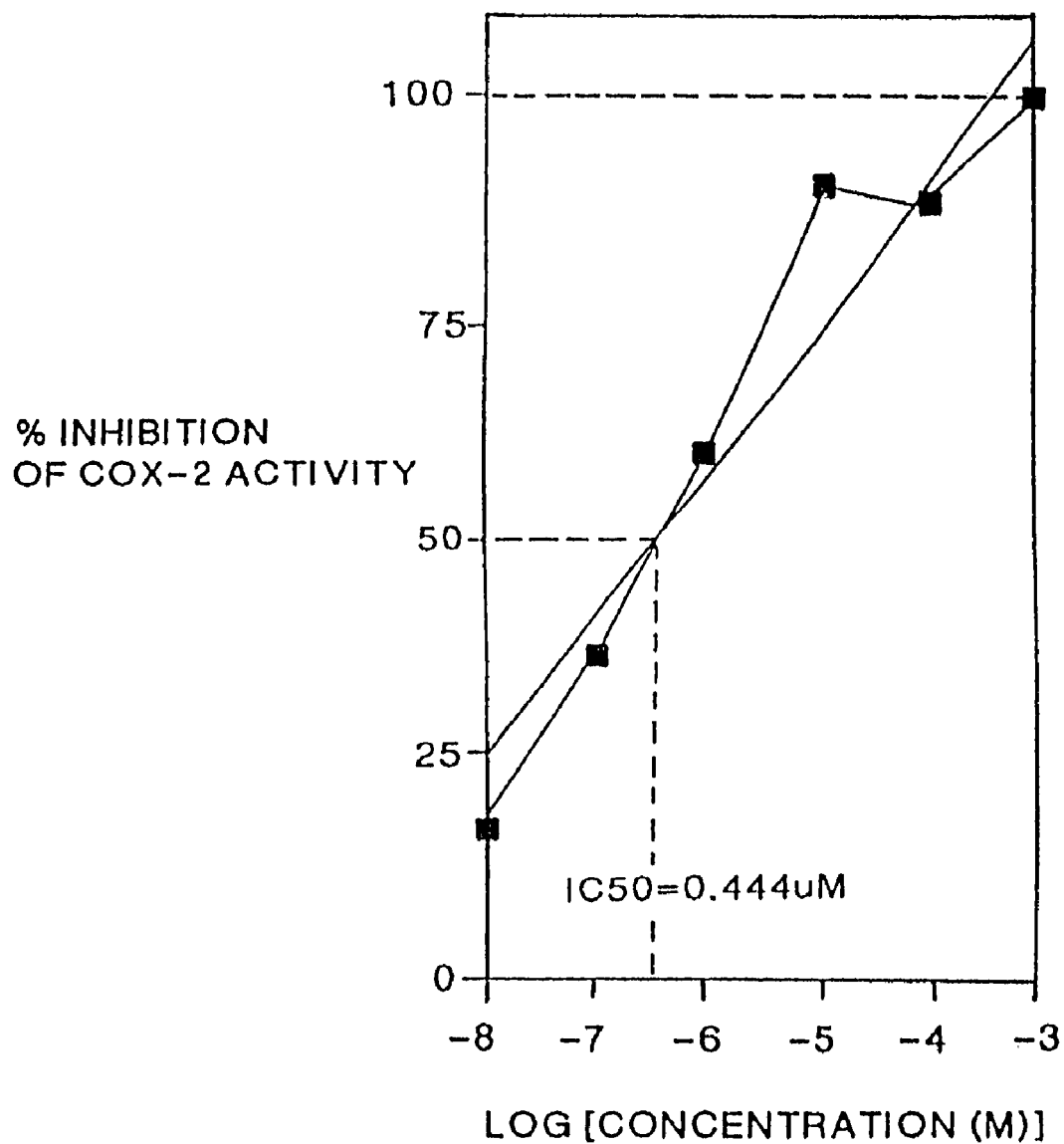
Figure 18E:
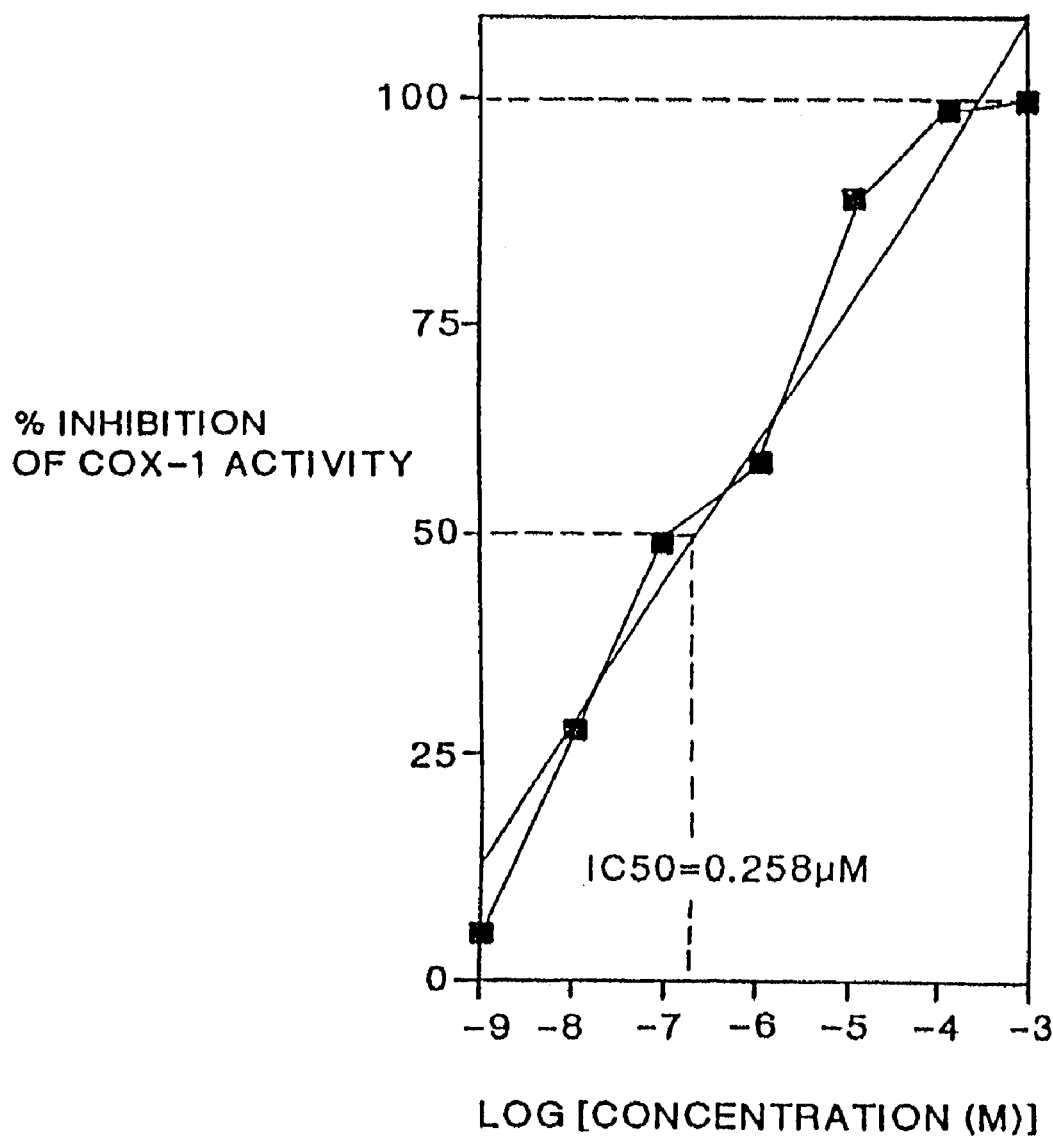
Figure 18F:
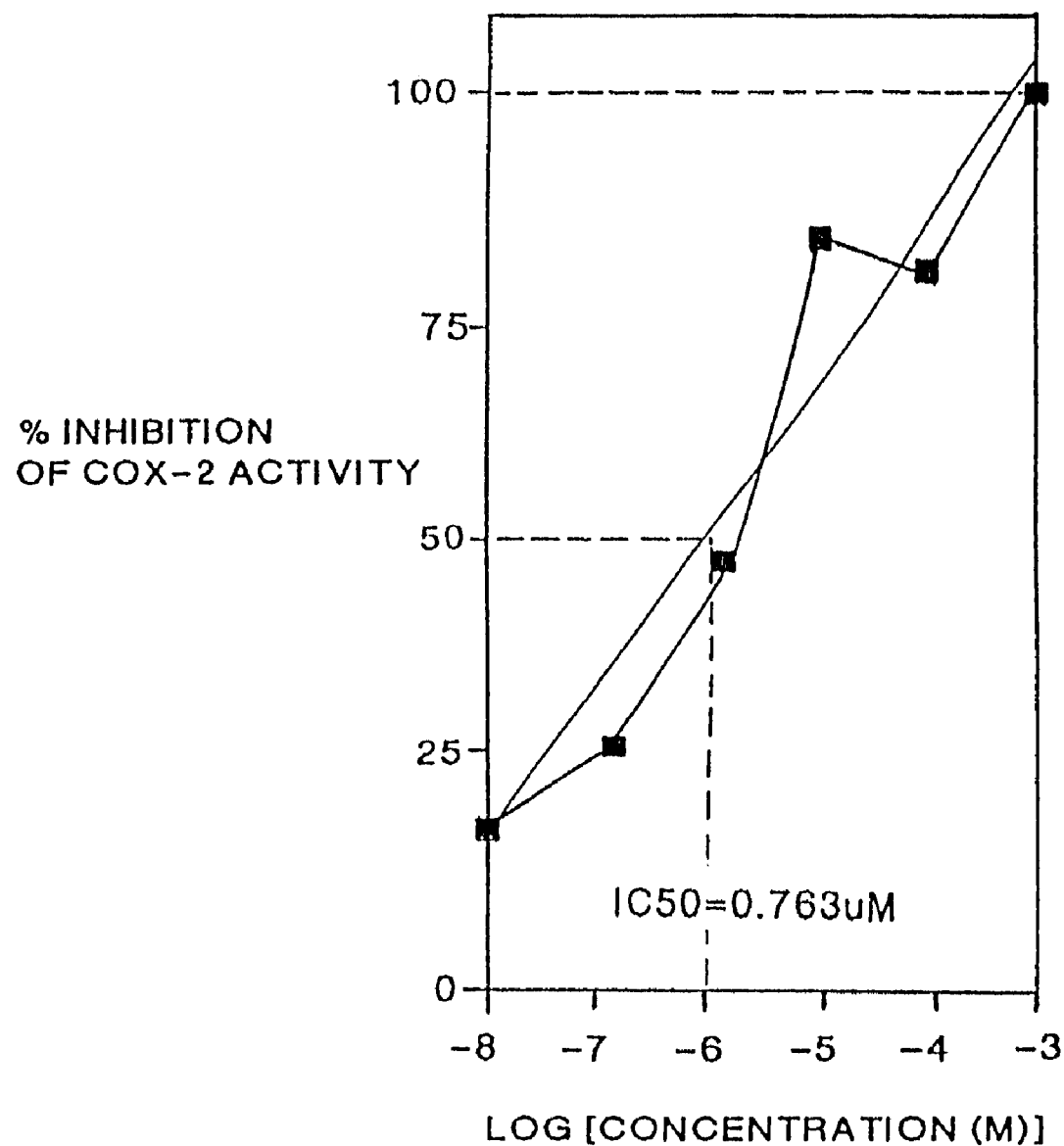
Figure 18G:
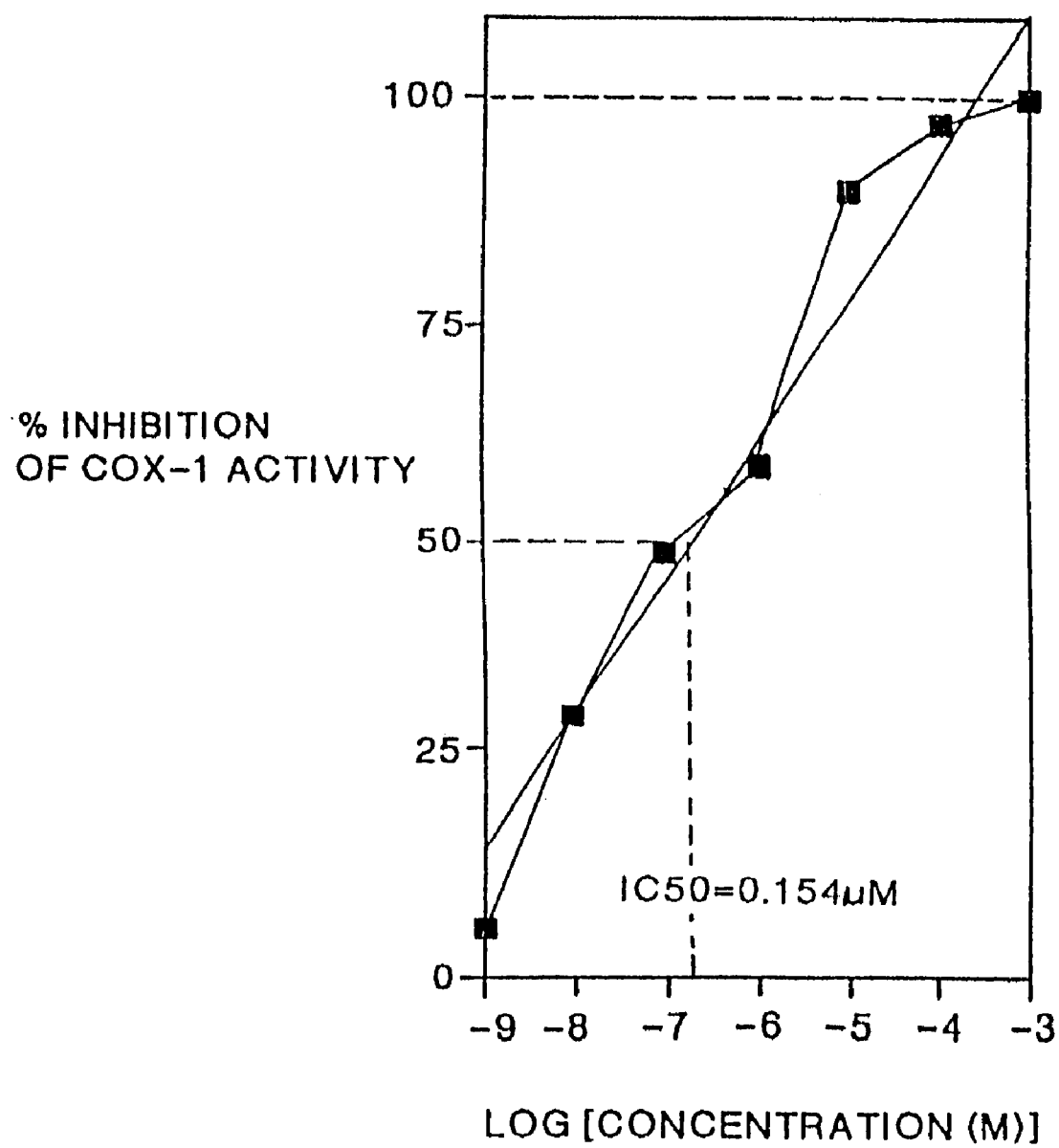
Figure 18H:
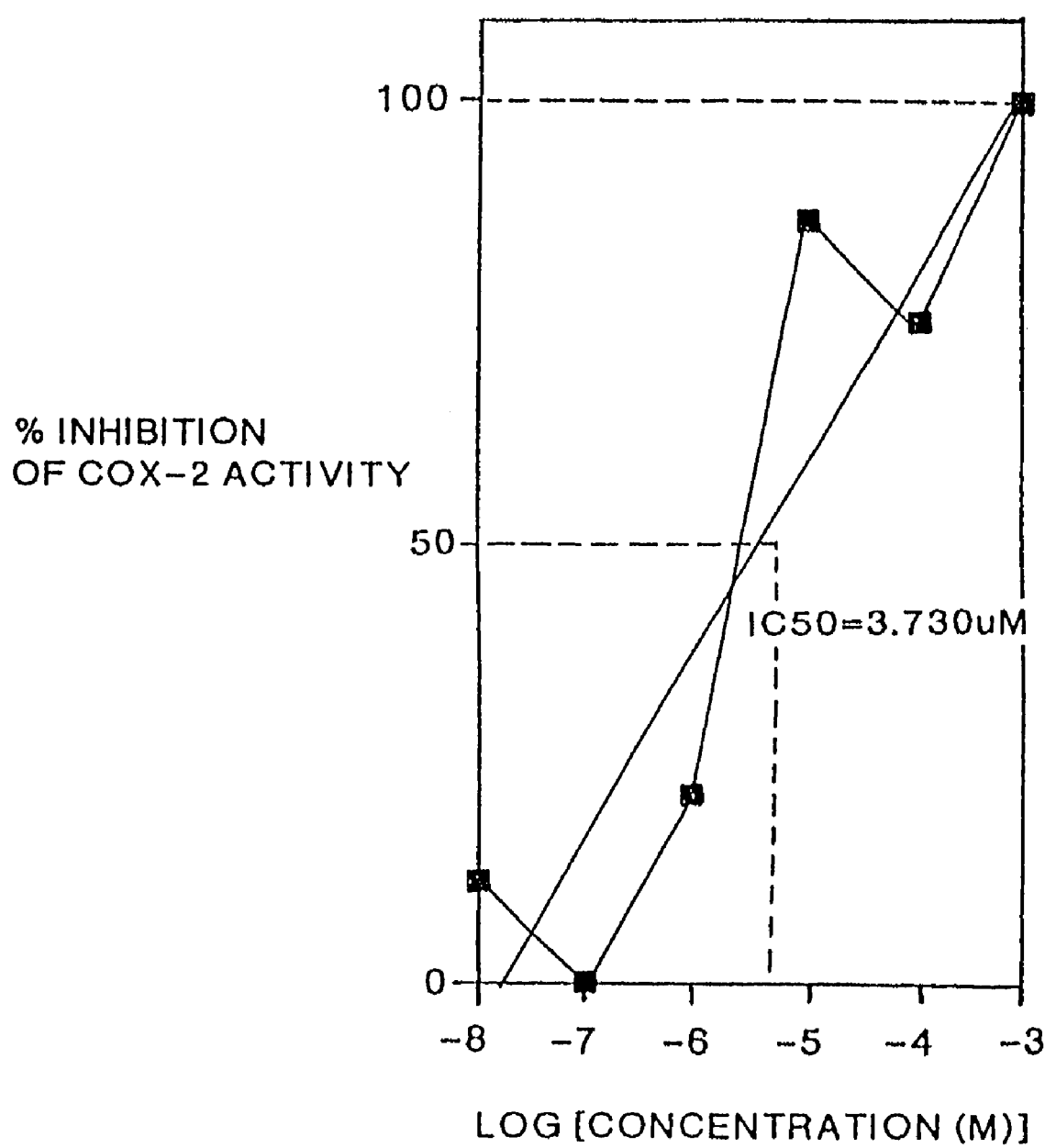
Figure 18I:
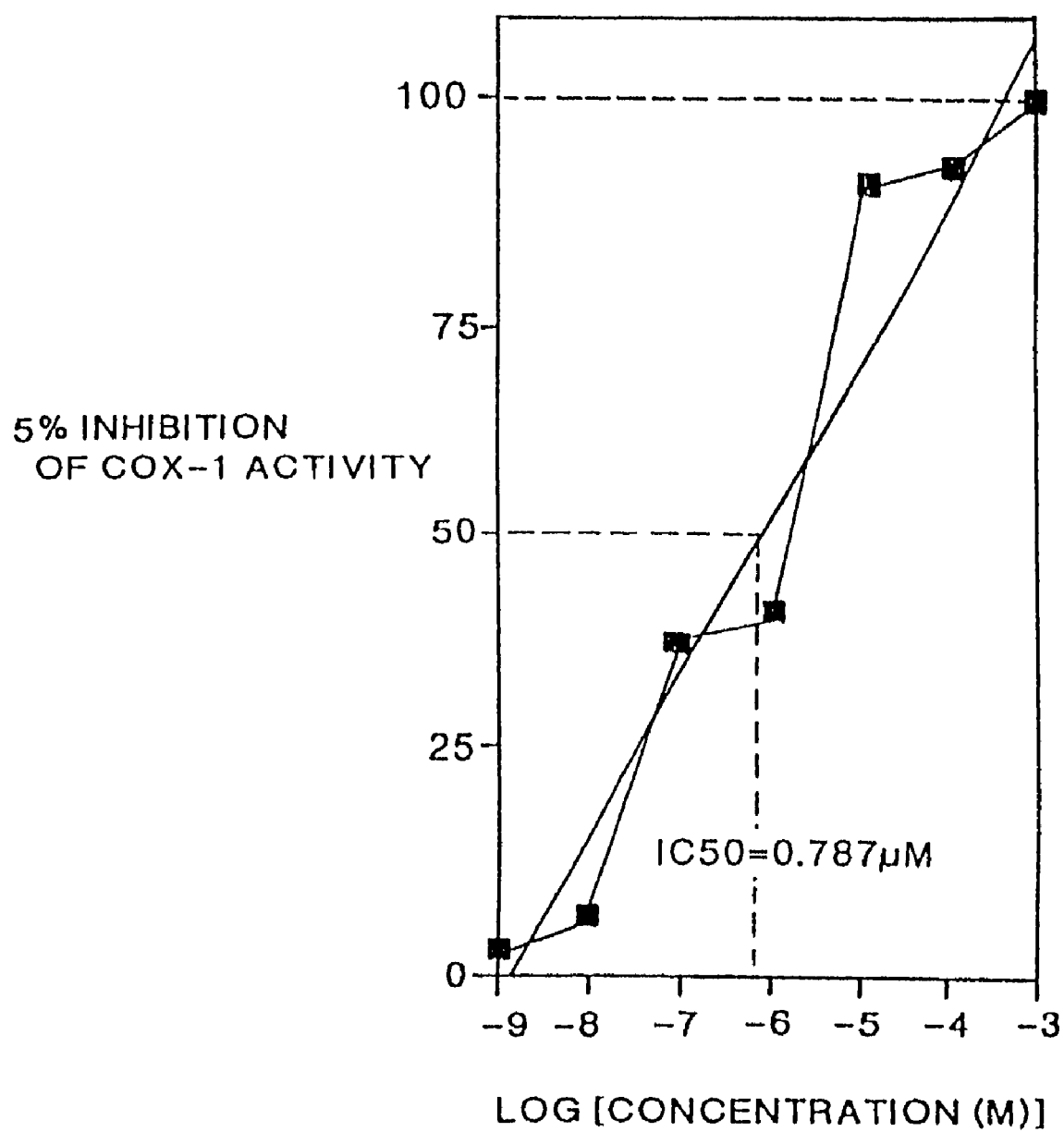
Figure 18J:
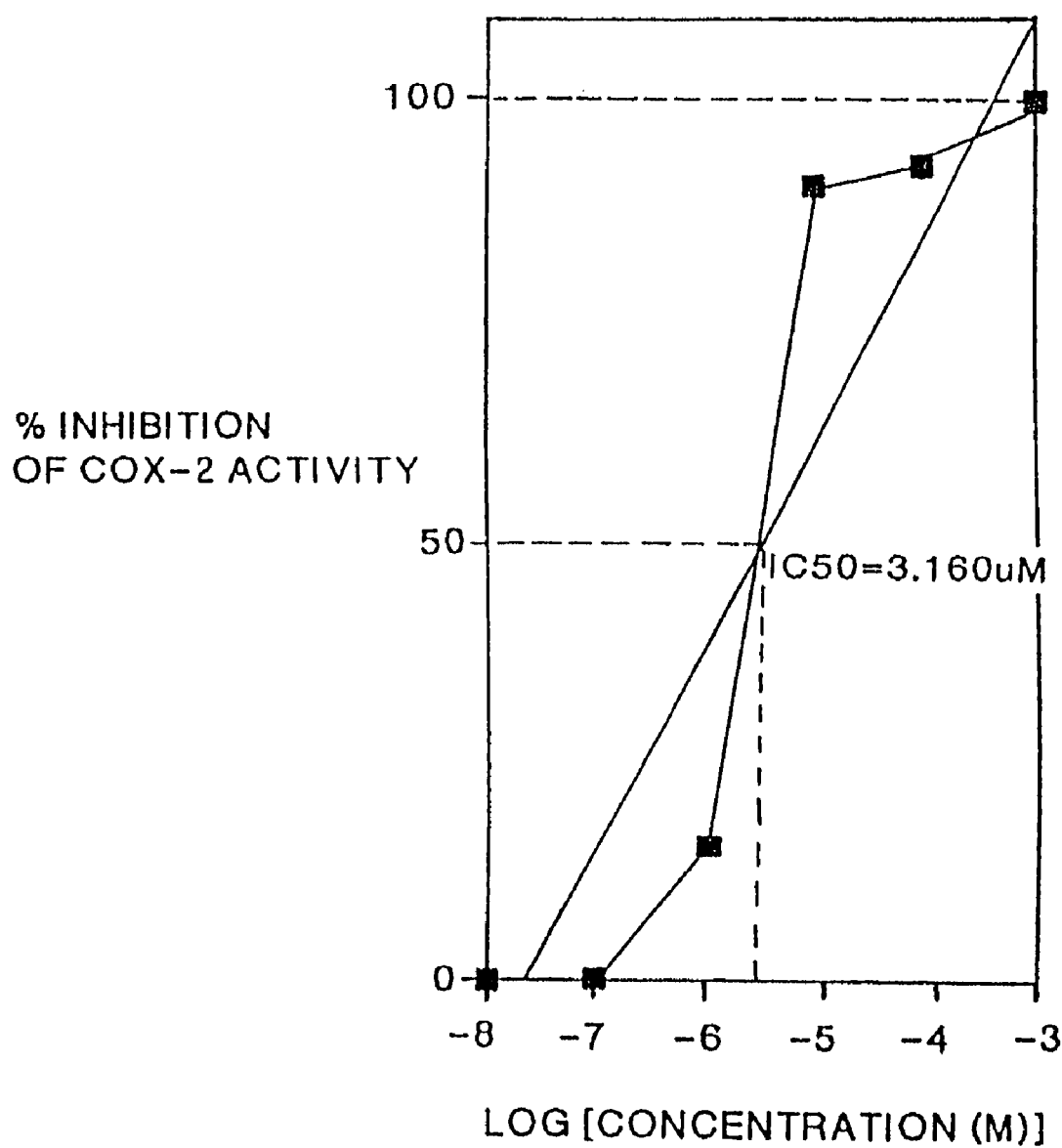
Figure 18K:
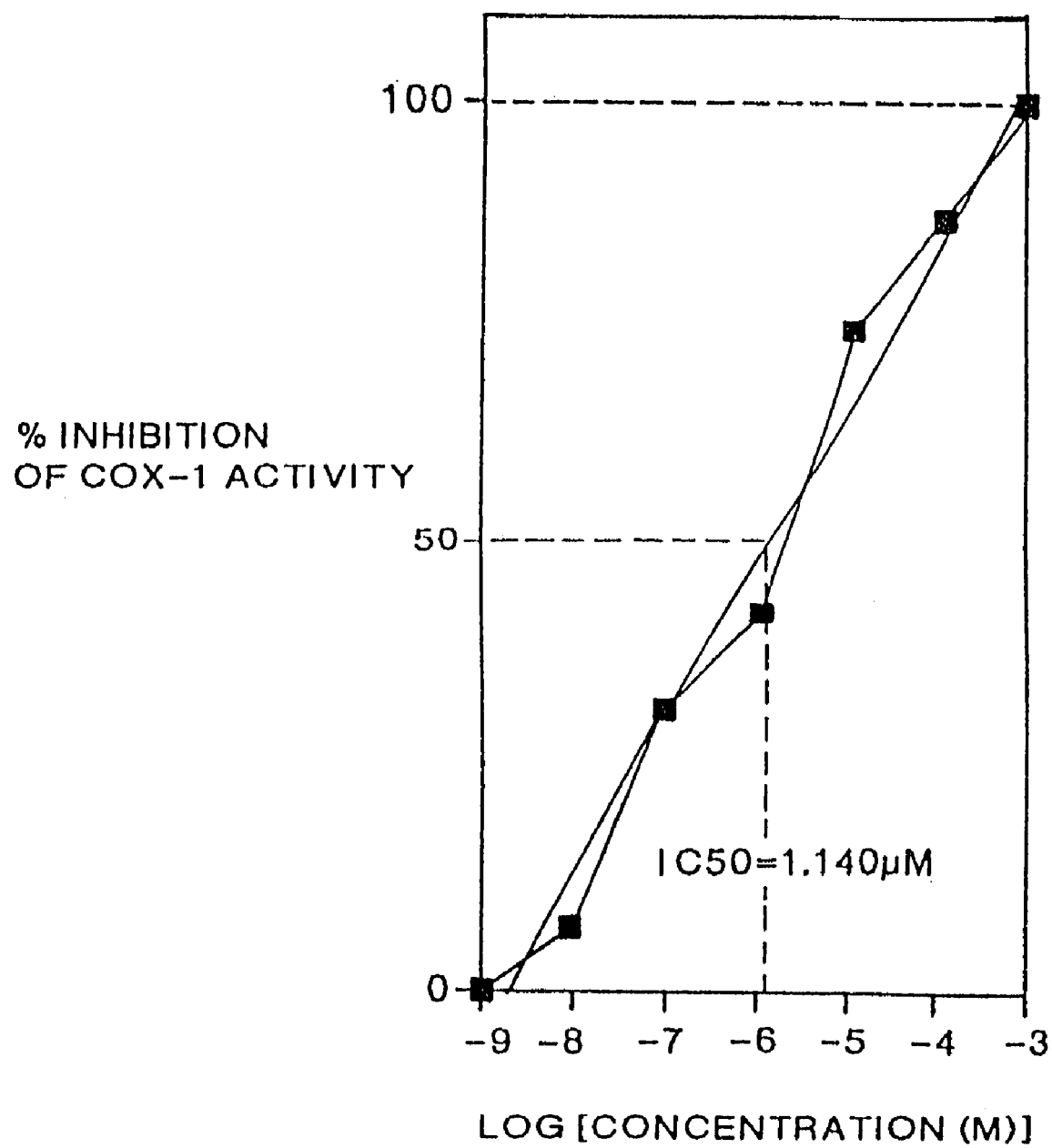
Figure 18L:
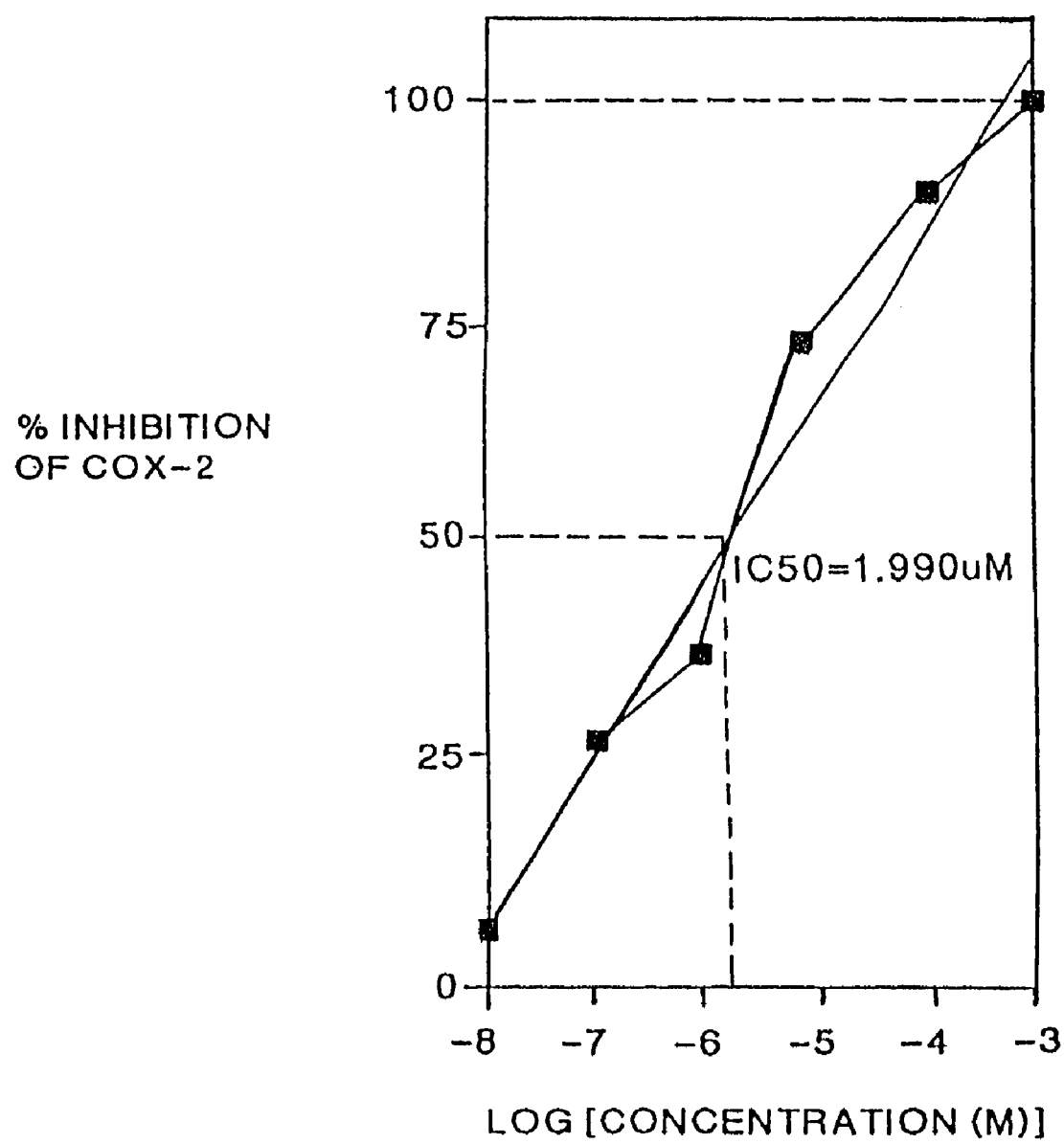
Figure 18M:
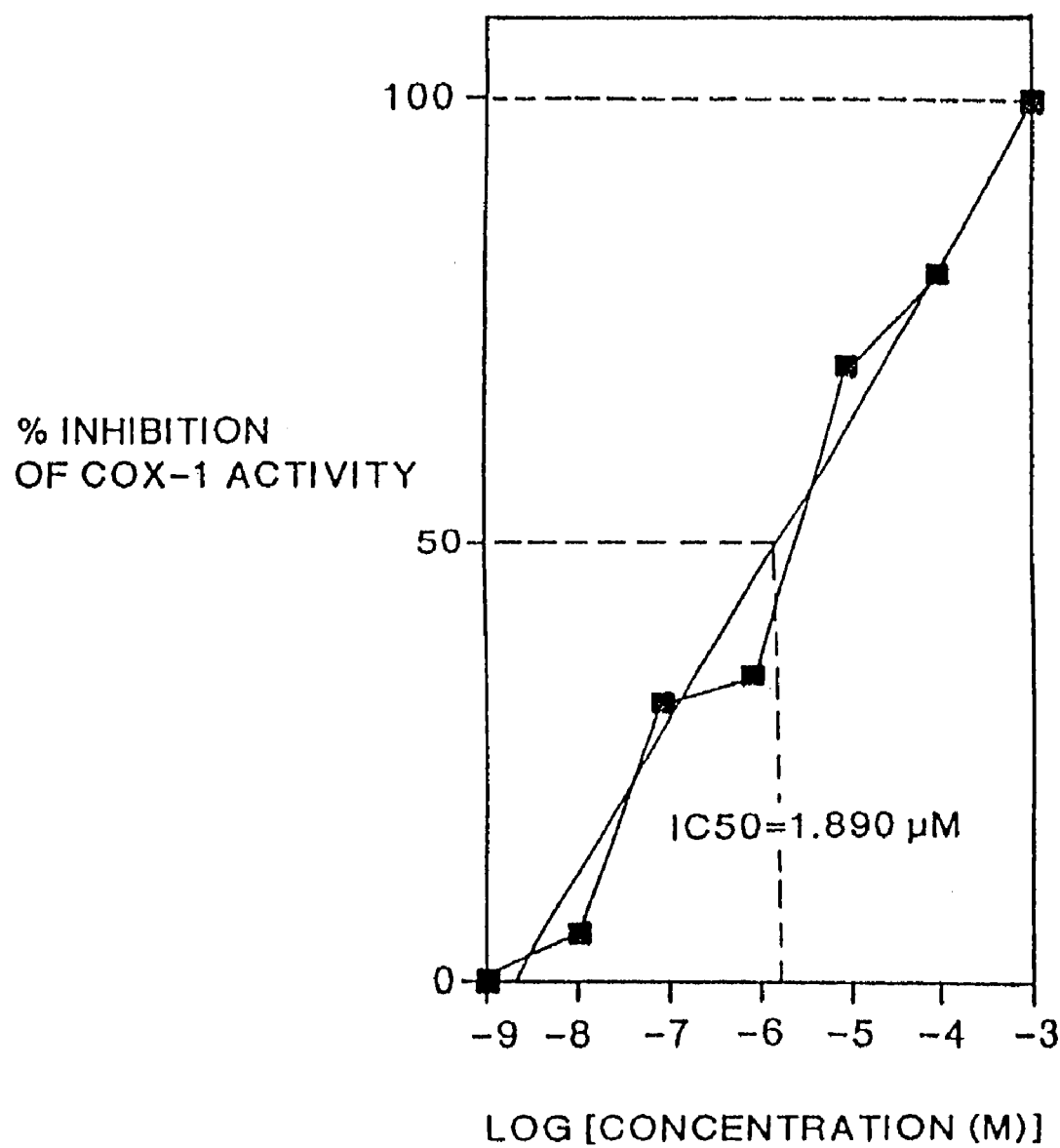
Figure 18N:
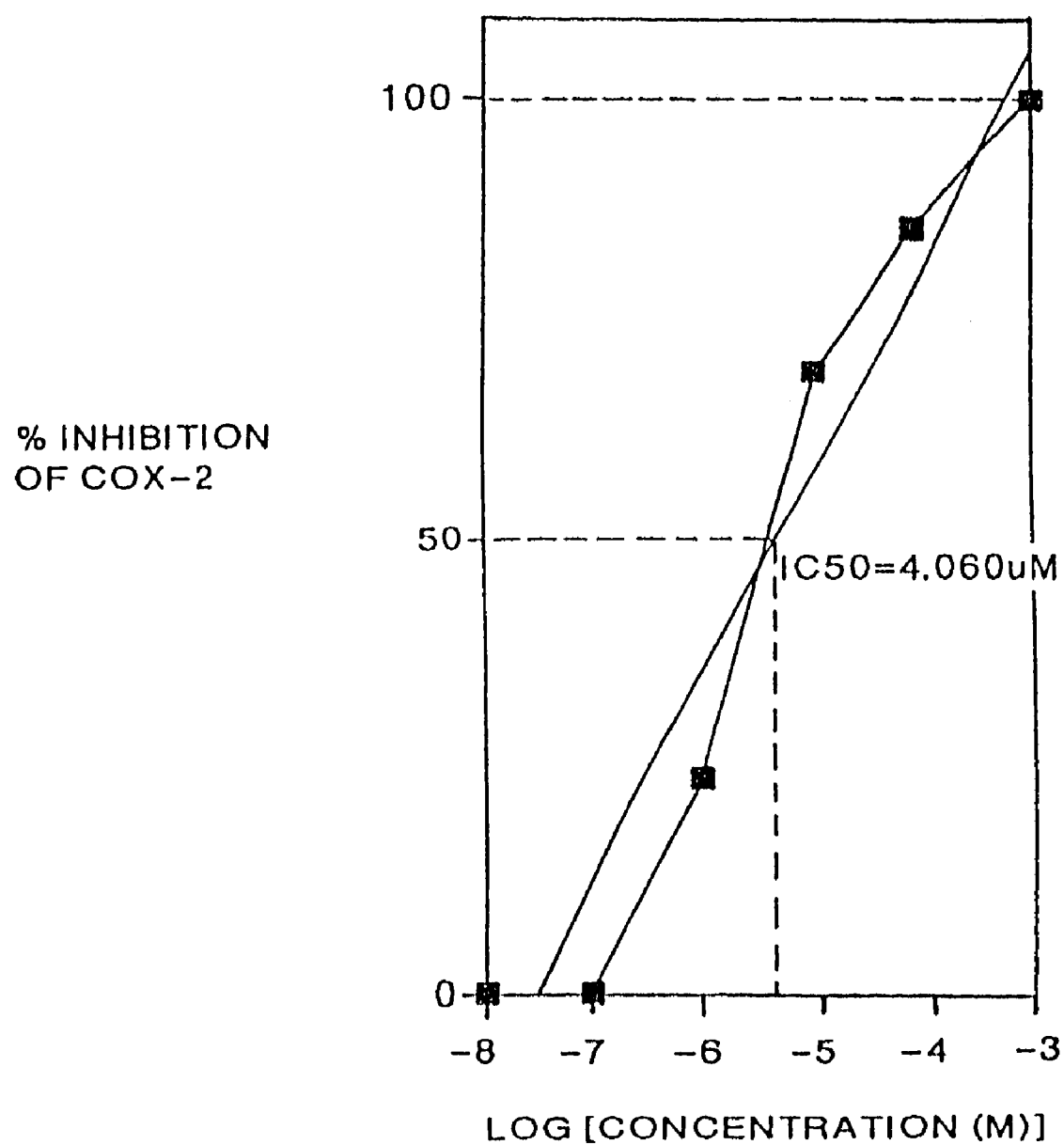
Figure 18O:
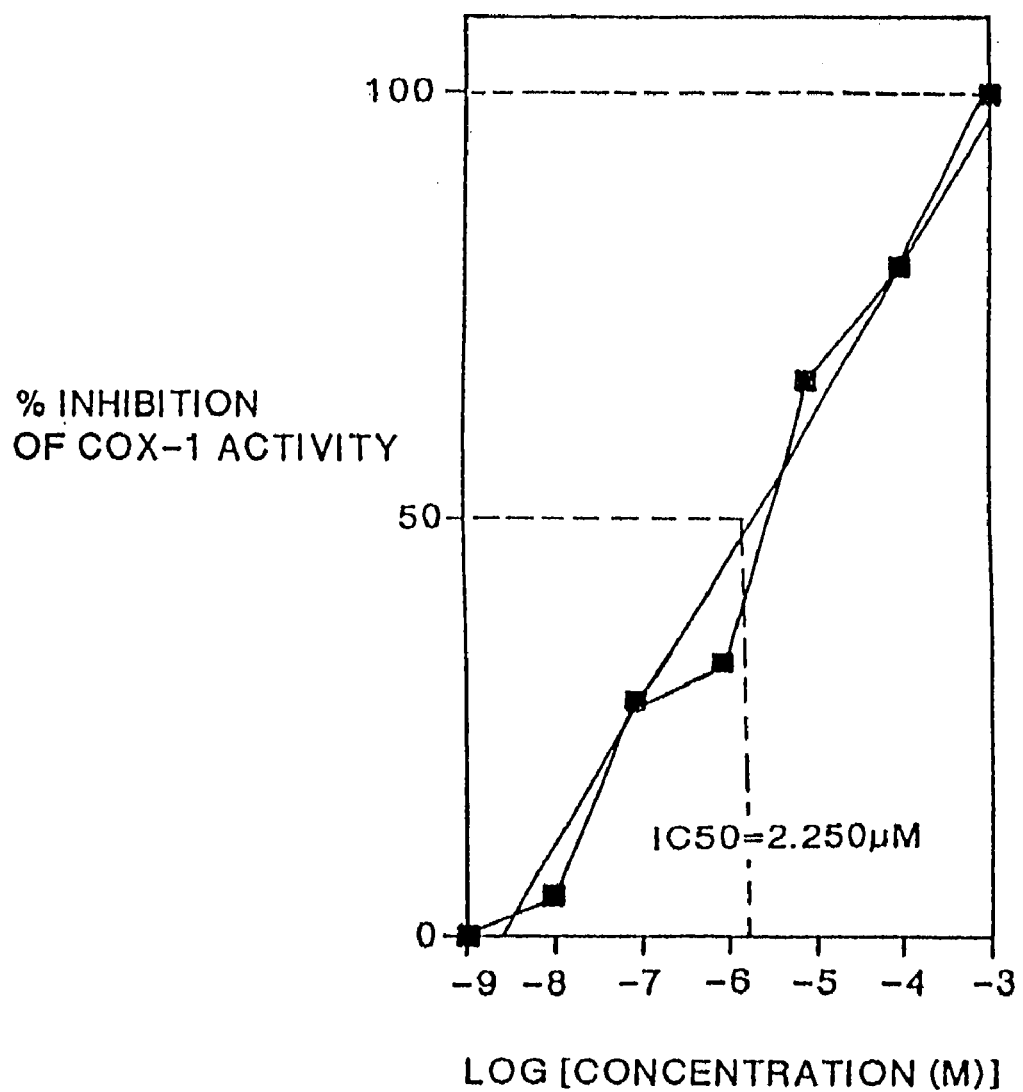
Figure 18P:
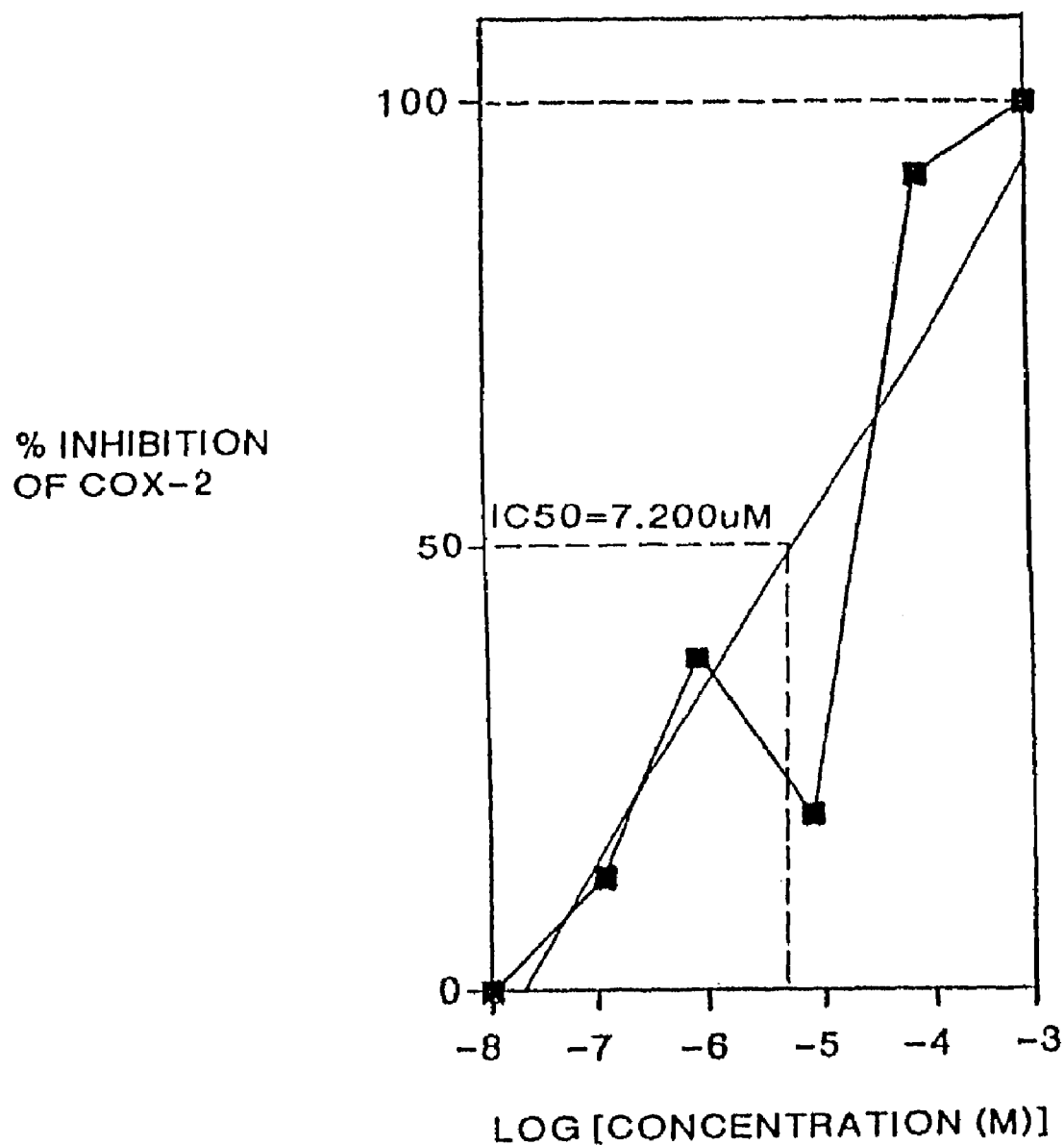
Figure 18Q:
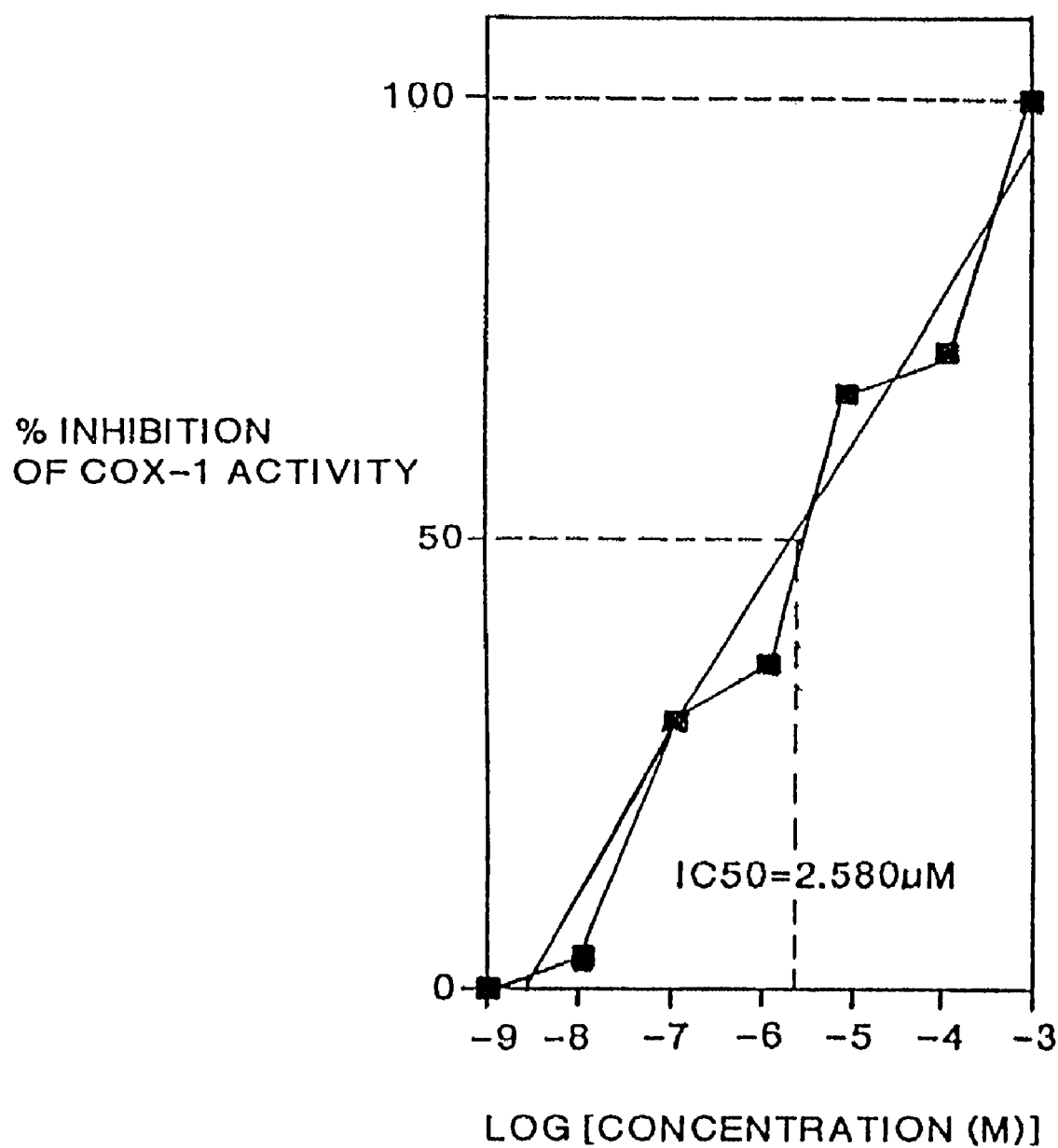
Figure 18R:
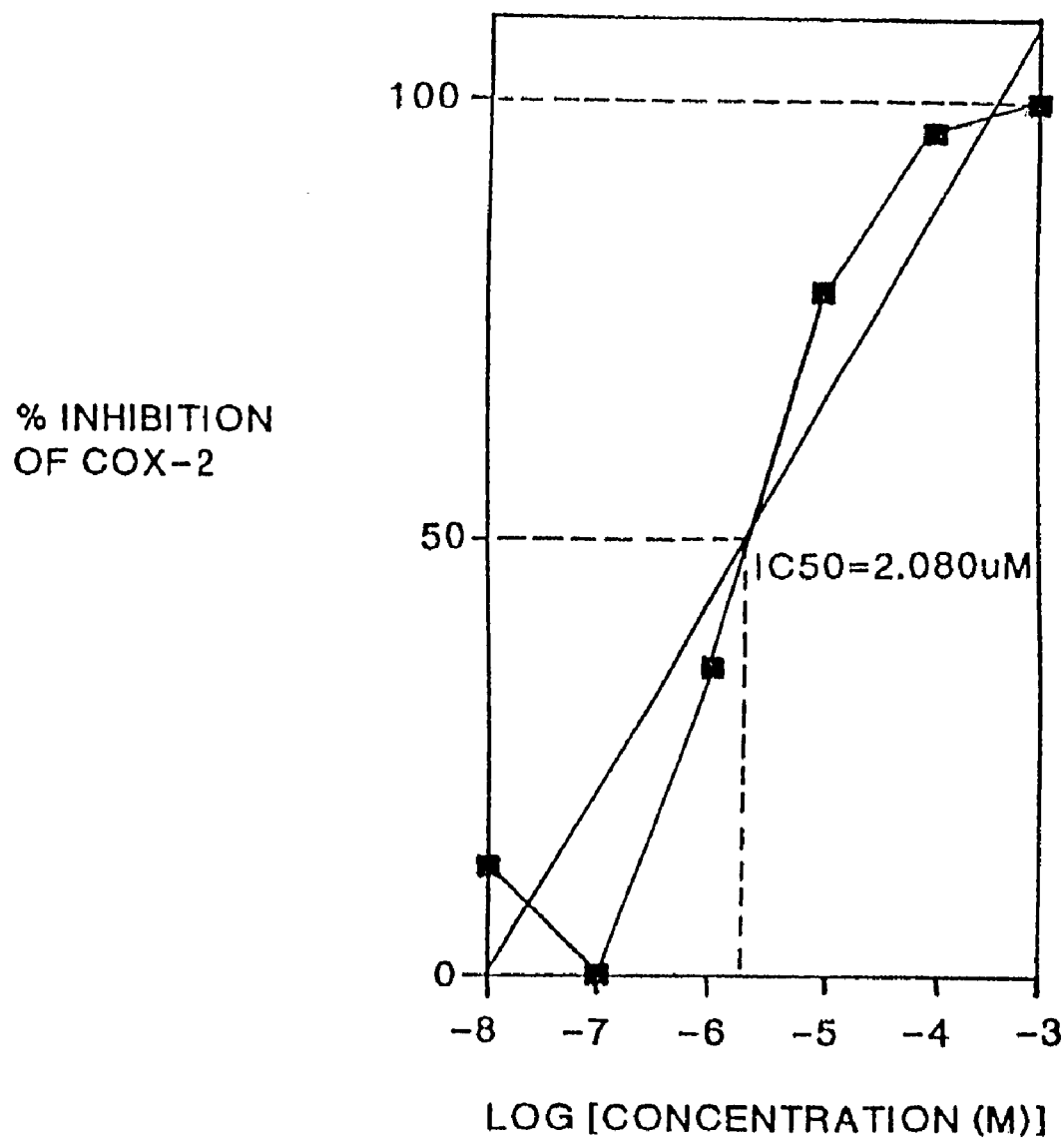
Figure 18S:
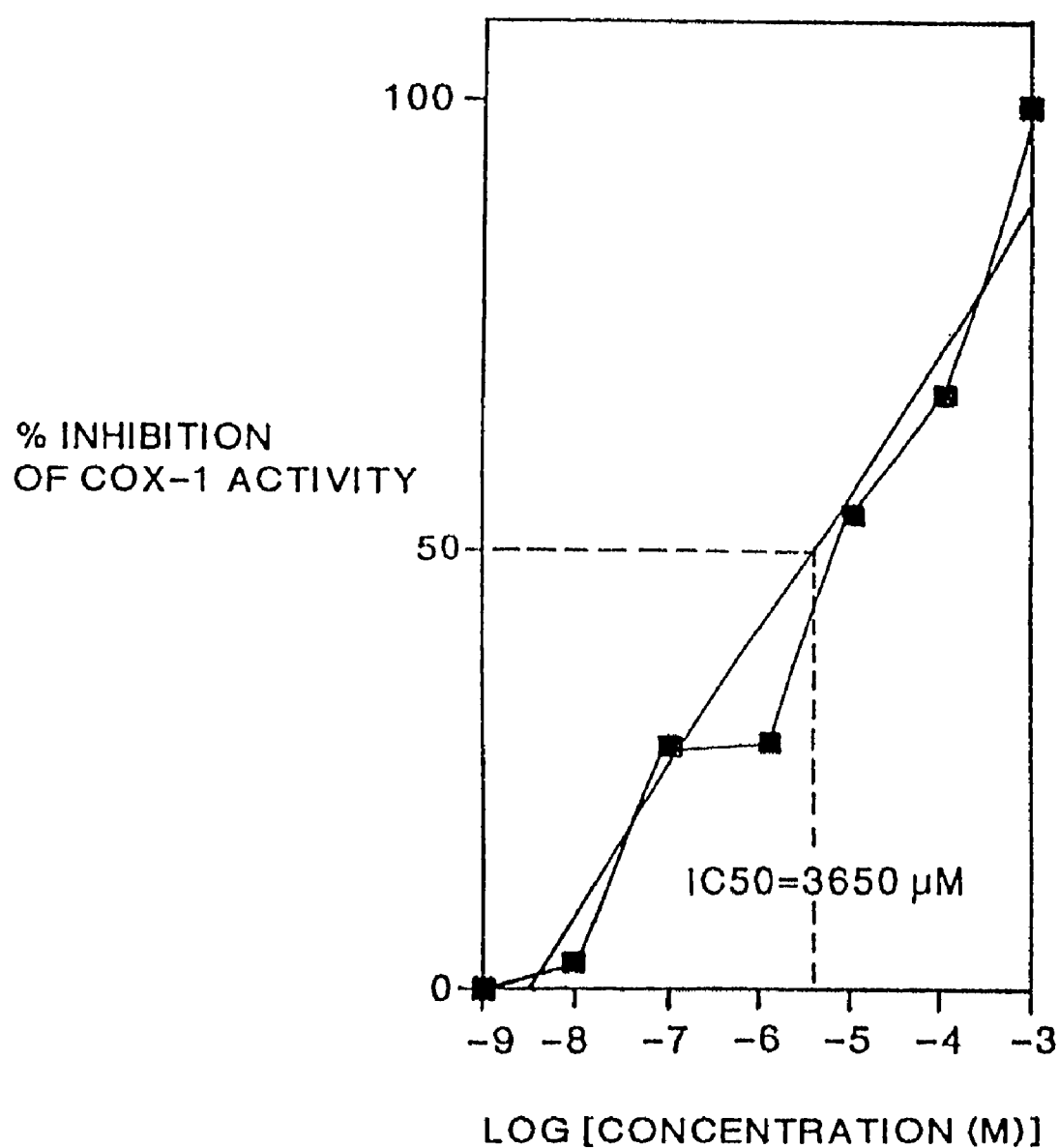
Figure 18T:
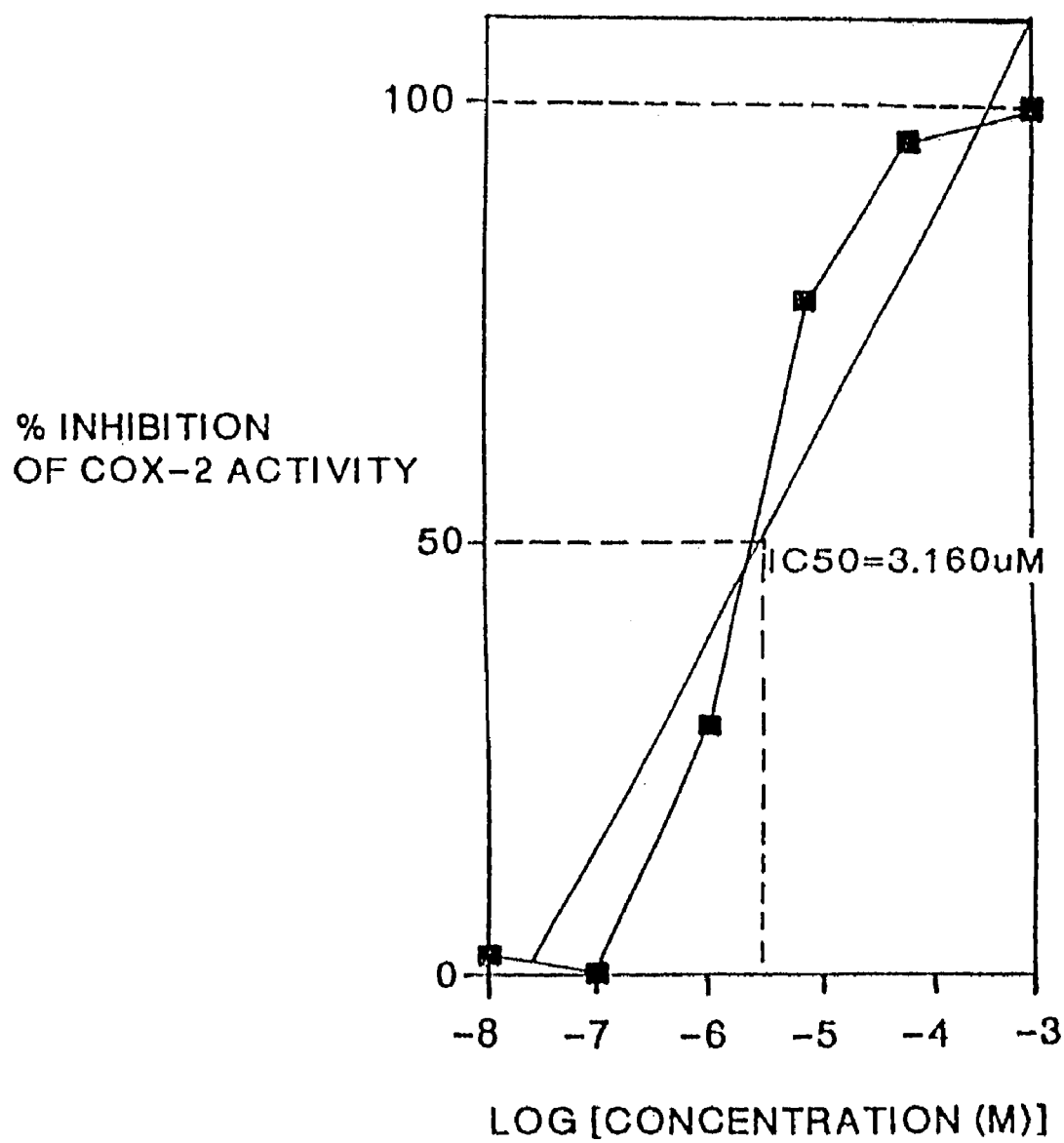
Figure 18U:
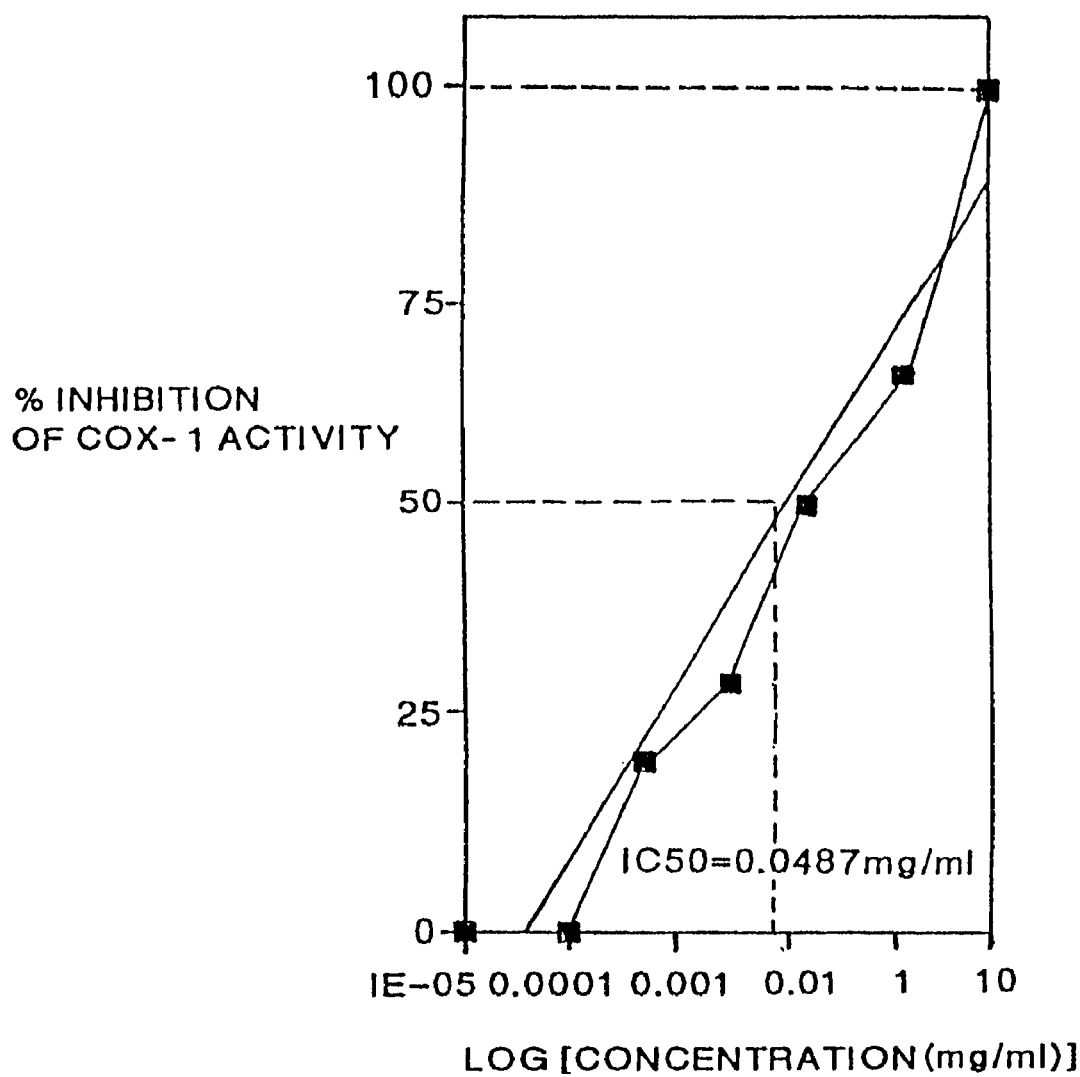
Figure 18V:
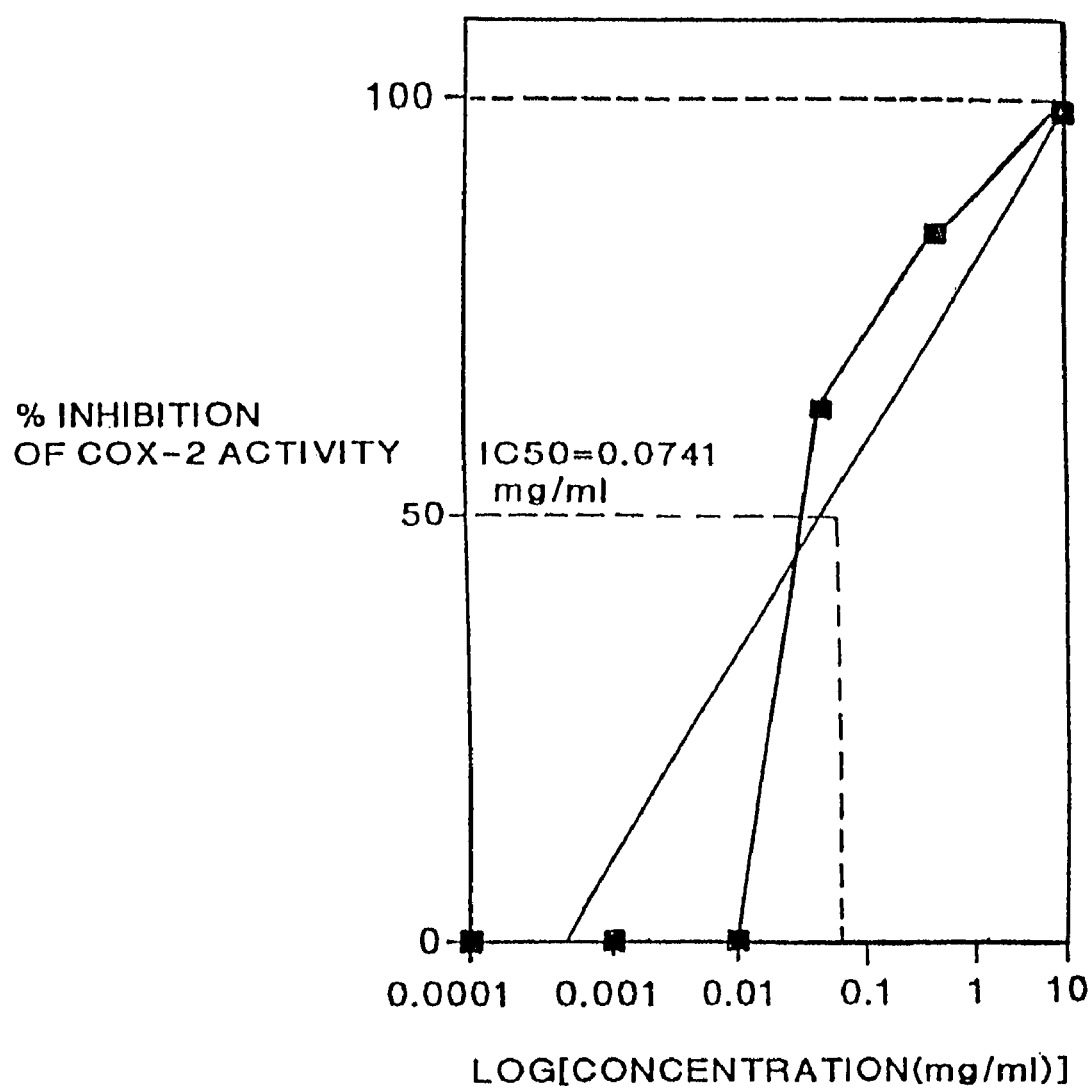
Figure 19A:
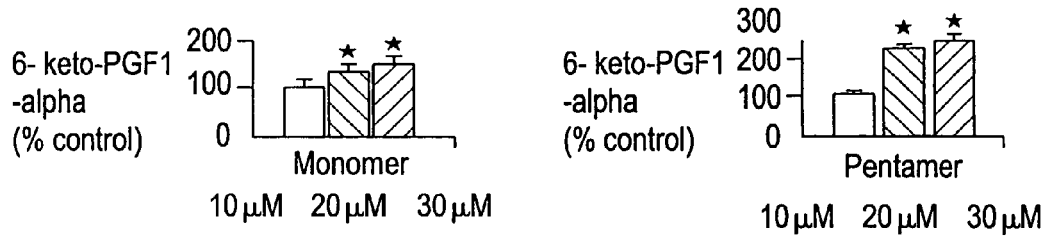
FIGS. 19A–D show the effect of phytochemicals on basal endothelial cell synthesis of the prostanoids and endothelins in BAECS.* means significantly different from control at a level of p<0.05.
Figure 19B:
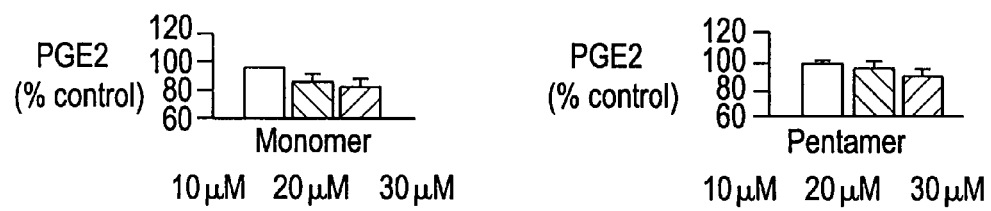
Figure 19C:
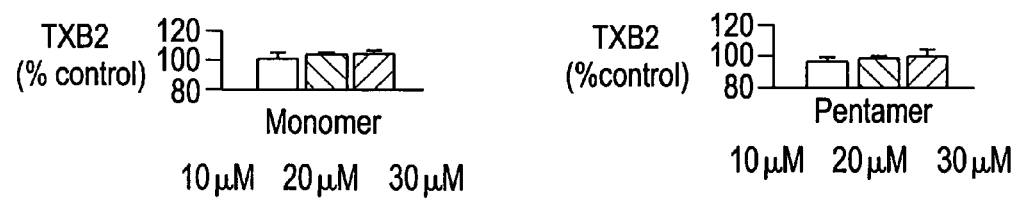
Figure 19D:
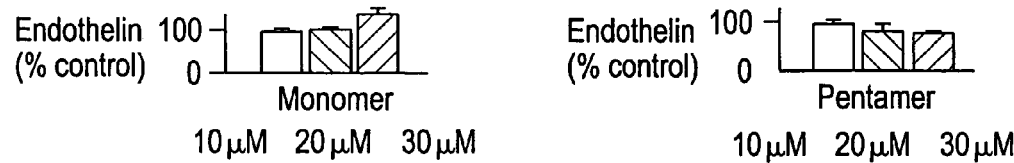

FIGS. 15A and B shows the effects of Indomethacin on COX-1 and COX-2 activities. FIGS. 16A and B shows the correlation between the degree of polymerization of the procyanidin and $IC_{50}$ with COX-1 and COX-2; FIG. 17 shows the correlation between $IC_{50}$ values on COX-1 and COX-2. FIGS. 18A through Y show the $IC_{50}$ values of each Sample 1–11) with COX-1 and COX-2.

The results indicate that the cocoa procyanidins have analgesic, anticoagulant, and anti-inflammatory utitlities. Since COX-2 has been linked to colon cancers, inhibition of COX-2 activity by the cocoa procyanidins provides a plausible mechanism by which the cocoa procyanidins have antineoplastic activity against colon cancer.

COX-1 and COX-2 are also implicated in the synthesis of prostaglandins. The above show that the cocoa procyanidins can modulate renal functions, immune responses, fever, pain, mitogenesis, apoptosis, prostaglandin synthesis, ulceration (e.g., gastric), and reproduction. It should be noted that modulation of renal function can affect blood pressure, again implicating the cocoa procyanidins in modulating blood pressure, vasodilation, and coronary conditions (e.g., modulation of angiotensin, bradykinin).

Reference is made to Seibert et al., PNAS USA 91:12013–12017 (December, 1994), Mitchell et al., PNAS USA 90:11693–11697 (December 1994), Dewitt et al., Cell 83:345–348 (Nov. 3, 1995), Langenbach et al., Cell 83:483–92 (Nov. 3, 1995), Sujii et al., Cell 83:493–501 (Nov. 3, 1995) and Morham et al., Cell 83:473–82 (Nov. 3, 1995).

Thus, in addition to having analgesic properties, there may also be a synergistic effect by the cocoa procyanidins when administered with other analgesics. Likewise, in addition to having antineoplastic properties, there may also be a synergistic effect by the cocoa procyanidins when administered with other antineoplastic agents.

Example 13

The Effects of Cocoa Procyanidin Extracts and Cocoa Procyanidin Oligomeric Fractions on Basal Endothelial Cell Release of Prostanoids and Total Endothelin (ET)

The effect of purified procyanidin monomers and pentamers from cocoa polyphenol extract on the release of the prostanoids prostacyclin, prostaglandin (PGE2) and thromboxane, and total endothelin on bovine and human endothelial cells in culture was studied.

Altered endothelial cell (EC) release of important signaling molecules, such as endothelins and prostanoids, could explain some vasoprotective phytochemical effects including beneficial alterations in vessel permeability and disposition toward platelet aggregation/thrombus formation.

Indomethacin was purchased from Cayman (Ann Arbor, Mich. USA). Monomeric and pentameric procyanidin fractions were purified from procyanidin-enriched cocoa powder according to the examples described in this application, and were analysed by the method of Hammerstone et al., "Identification of Procyanidins in Cocoa, *Theobroina cacao*, and Chocolate Using High-Performance Liquid Chromatography/Mass Spectrometry", J. Agric. Food Chem., 47:2: 490–496, 1999. Conformation of molecular weight purity was obtained by mass spectrometry.

Bovine aortic endothelial cells (BAEC) were provided by M. E. O'Donnell of University of California, Davis. Human aortic endothelial cells (HAEC) were purchased from Clonetics (San Diego, Calif.). The cells were cultured in Eagle's minimum essential medium (EMEM) as described previously by Schramm et al. "Endothelial Cell Basal $PGI_2$ Is Stimulated By Wine In Vitro: One Mechanism That May Mediate The Vasoprotective Effects Of Wine", J. Nutr. Biochem. 8:647–651, 1997; "Differential Effects Of Small And Large Molecular Weight Wine Phytochemicals On Endothelial Cell Eicosanoid Release", J. Agric. and Food. Chem. 46(5): 1900–1905, 1998; and "Energy Dependent System In Mammalian Endothelial Cells For Rapid Flavonoid Up-Take", J. Nutr. Biochem. In Press, 1999.

ECs (passage<11) were seeded onto 24-well plates with EMEM containing 2 mmol glutamine/L, 10% fetal bovine serum, 100 units penicillin/L, 0.1 mg streptomycin/L, and 0.25 µg amphotericin/L. Confluent cells were treated in 250 ml of phenol red-free EMEM containing treatment compounds where applicable. Medium incubated with EC's was analyzed after application of procyanidin fractions (10, 20, and 30 pmol/L) and incubation with ECs for 0 and 20 min. The medium was stored at −70° C. until analyzed by immunoassay as described below. EC integrity was monitored by Trypan Blue exclusion as described in Bioadjieras et al., "Exclusion Of Trypan Blue From Microcarriers By Endothelial Cells: An In Vitro Barrier Function Test", Methods in Lab. Invest. 50:239–246, 1984.

Immunoassay procedures were conducted as described by Westcott et al, "Analysis Of 6-Keto PGF1 Alpha, 5-HETE, And LTC4 In Rat Lung: Comparison Of GM/MS, RIA and EIA", Prostaglandins 32:857–873, 1986; Yakota et al, "Enzyme Immunoassay Of Prostanoids In Blood And Urine", Adv. Prostgl. Thrombox. Leukot. Res. 15:33–34, 1985; Schramm et al, 1997; 1998;1999. Medium total ET (ET-1+ET-2+ET-3) was measured with Cayman immunoassay #583151. The prostacyclin ($PGI_2$) metabolite 6-keto prostaglandin F1-alpha was measured with Cayman enzyme immunoassay #515211, the thromboxane ($TXA_2$) metabolite $TXB_2$ was measured with Cayman enzyme immunoassay 519031, and $PGE_2$ was determined with Cayman immunoassay #514016.

An endothelial cell (EC) monolayer culture system was used to compare the effects of the purified cocoa procyanidin monomers and pentamers in a system that closely mimics the EC monolayer of a blood vessel. The established assay conditions mimic those used previously to show that a wine fraction with mass <3000 da. induced different effects on EC prostanoid synthesis than did a wine fraction having a mass of >3000 (Schramm et al, "Differential Effects Of Small And Large Molecular Weight Wine Phytochemicals On Endothelial Cell Eicosanoid Release", J. Agric. and Food. Chem. 46(5): 1900–1905, (1998). The effects on basal cell function were examined. Neither cell viability nor cell morphology was effected by cocoa procyanidin treatments. Each milliliter of control medium incubated with BAECs for 20 min contained 73.5=+/−0.044 ng TXB2 and 294+/−6.3 pg PGE2.

As shown in FIG. 19, the addition of the monomeric or pentameric cocoa procyanidins to medium incubated with BAECs for 20 min altered medium prostanoid and ET concentrations when compared to the control medium alone. Media containing either monomeric ($A^1$) or pentameric ($A^2$) procyanidins contained more 6-keto-$PGF^1$-alpha than the control medium. Medium $PGE^2$ was reduced by the monomeric fraction (B1) in a dose-dependent manner and by the pentameric fraction ($B^2$) at 30 (µM. No significant effect of either cocoa procyanidin fraction was noted on medium TXB (C1–2). Although the monomeric and pentameric cocoa procyanidin fractions had similar effects on medium 6-keto-$PGF^1$-alpha and $PGE^2$, they had opposite effects on medium ET, with the monomeric fraction ($D^1$) increasing the concentration of ET in the culture medium at 30 µM and the pentameric fraction ($D^2$) decreasing medium ET concentration in a dose dependent manner.

Figure 20B:
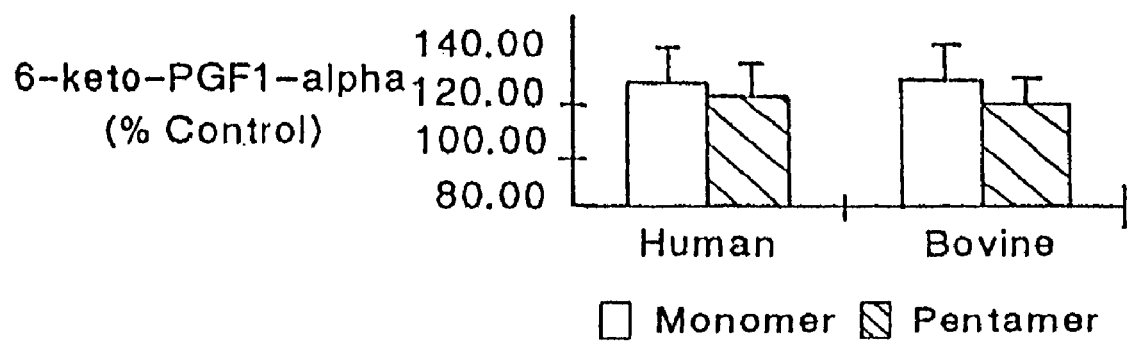
FIGS. 20A & B show the effects of cell species on procyanidin induced alterations in EC release of prostacyclin and endothelin.
Figure 20A:
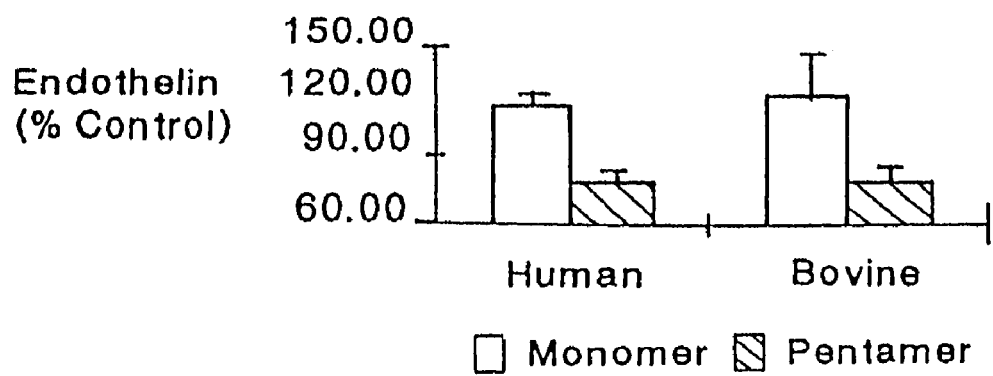

Data in FIGS. 20A and 20B demonstrate the similar manner in which monomeric and pentameric cocoa procyanidins affected aortic ECs from cows (BAEC) and humans (HAEC).

The above data demonstrate that the procyanidins present in cocoa can induce eicosanoid and endothelin effects which promote a state of vessel relaxation and decreased platelet aggregation/thrombus formation, i.e., induction of prostacyclin and inhibition of endothelin and prostaglandin. The cocoa procyanidin extracts, either as dietary components or in acceptable pharmacological form, should be useful in vasoprotective prophylaxis and treatment for vascular disease.

Example 14

The Effects of the Consumption of a Procyanidin-Enriched Cocoa Beverage on Platelet Activity The effects of consumption of a cocoa beverage on modulation of platelet activation and primary haemostasis were studied.

Thirty healthy, non-smoking adults with no history of heart disease or haemostatic disorders participated in the study. Venous blood was obtained from 10 subjects (4 males and 6 females, 24–49 years of age) who consumed a cocoa beverage, 10 subjects (4 males and 5 females, 26–50 years of age) who consumed a caffeine beverage as a control, and 10 subjects (4 males, 6 females, 24–50 years of age) who consumed water as a control. All women were premenopausal and were not taking estrogens. Participants were instructed to abstain from nonsteroidal, anti-inflammatory medication for at least 4 days, from alcoholic beverages for at least 2 days, and from caffeine- or theobromine-containing foods for at least 24 hours before the test and during the test day.

Blood was obtained from each test and control subject between 8 and 10 AM in two 5-ml evacuated tubes containing 0.5 ml of 3.2% buffered sodium citrate solution (Becton Dickinson, Franklin Lakes, N.J.). Specimens obtained as the result of a traumatic venipuncture and/or those with obvious clots were not analyzed. Test subjects then drank 300 ml of a beverage containing 18.75 g of procyanidin enriched cocoa powder and 12.5 g of sucrose mixed with distilled water (see Adamson, G. E., Lazarus, S. A., Mitchell, A. E., Prior R. L., Cao, G., Jacobs, P. H., Kremers B. G., Hammerstone, J. F., Rucker R., Ritter K. A., Schmitz H. H., *HPLC Method for the Quantification of Procyanidins in Cocoa and Chocolate Samples and Correlation to Total Antioxidant Capacity, J Ag. Food Chem.;* 1999; 47 (10) 4184–4188). The cocoa powder provided approximately 960 mg of total procyanidins, 17 mg caffeine and 285 mg theobromine (see Clapperton, J., Hammerstone, J. F., Romanczyk, L. J., Yow, S., Lim, D., Lockwood, R., *Polyphenols and Cocoa Flavour, Proceedings, 16th International Conference of Groupe Polyphenols,* Lisbon, Portugal, Groupe Polyphenols: Norbonne, France, 1992; Tome II, pp. 112–115.). Control subjects drank either a beverage containing 17 mg caffeine and 12.5 g sucrose or plain water. Additional blood samples were obtained 2 and 6 hours after consumption of the beverages. One female subject was not present for the 6-hour blood draw after cocoa consumption.

Procyanidins were quantified as follows: a composite standard was made using commercially available (−)-epicatechin for the monomer. Dimers through decamers were obtained in a purified state by the methods described in Hammerstone, J. F. et al., "Identification of Procyanidins in Cocoa (*Theobroma cacao*) and Chocolate Using High-Performance Liquid Chromatography/Mass Spectrometry", *J. Ag. Food Chem.;* 1999; 47 (10) 490–496, Lazarus, S. A. et al., High-performance Liquid Chromatography/Mass Spectrometry Analysis of Proanthocyanidins in Foods and Beverages, *J. Ag. Food Chem.;* 1999; 47 (9); 3693–3701 and Adamson, G. E. et al., "HPLC Method for the Quantification of Procyanidins in Cocoa and Chocolate Samples and Correlation to Total Antioxidant Capacity", *J. Ag. Food Chem.;* 1999; 47 (10) 4184–4188. Standard Stock solutions using these compounds were analyzed using the normal-phase HPLC method described previously with fluorescence detection at excitation and emission wavelengths of 276 nm and 316 nm, respectively. Peaks were grouped and their areas summed to include contributions from all isomers within any one class of oligomers and calibration curves generated using a quadratic fit. Monomers and smaller oligomers had almost linear plots which is consistent with prior usage of linear regression to generate monomer-based and dimer-based calibration curves.

These calibration curves were then used to calculate procyanidin levels in samples prepared as follows: First, the cocoa or chocolate sample (about 8 grams) was defatted using three hexane extractions (45 mL each). Next, one gram of defatted material was extracted with 5 mL of the acetone/water/acetic acid mixture (70:29.5:0.5 v/v). The quantity of procyanidins in the defatted material was then determined by comparing the HPLC data from the samples with the calibration curves obtained as described above (which used the purified oligomers). The percentage of fat for the samples (using a one gram sample size for chocolate or one-half gram sample size for liquors) was determined using a standardized method by the Association of Official Analytical Chemists (AOAC Official Method 920.177). The quantity of total procyanidin levels in the original sample (with fat) was then calculated. Calibration was performed prior to each sample run to protect against column-to-column variations.

Within 10 minutes of draw, whole blood was incubated in polystyrene tubes for 5 minutes at room temperature with 10 µl HEPES buffer (pH 7.4, unstimulated control), 20 or 100 µM ADP or 20 µM epinephrine (BioData, Horsham, Pa.) in the presence or absence of the peptide Arg-Gly-Asp-Ser (Sigma, St. Louis, Mo.). After 5 minutes, samples were suspended in 1 ml HEPES buffer and 100 µl of sample were transferred to tubes containing saturating concentrations (20 µL) each of the following fluorescent-labeled monoclonal antibodies: PAC1-fluorescein isothiocyanate (FITC), anti-CD62P-phycoerythrin (PE) and anti-CD42a-PerCP. PAC1 recognizes the activated conformation of the fibrinogen-binding receptor GPIIb-IIIa and anti-CD62P recognizes P-selectin, present on the surface of activated platelets. Anti-CD42a recognizes GPIb-IX, which is on the surface of both activated and resting platelets. Mouse IgG, FITC and mouse IgG, PE were used as isotype controls. The Arg-Gly-Asp-Ser-peptide was used to block binding of the PAC1 antibody to platelets and thus set the negative control marker on the flow cytometer. Antibodies and isotype controls were purchased from Becton Dickinson Immunocytometry Systems, Inc., San Jose, Calif.

Whole blood samples in the presence and absence of the agonists ADP and epinephrine were incubated with monoclonal antibodies or isotype control for 20 minutes in the dark at room temperature. Samples were then fixed in filtered 1% paraformaldehyde (pH 7.2) and stored in the dark at 2–8° C. All samples were analyzed within 48 hours on a FACScan flow cytometer using LYSYS II software. The flow cytometer performance was verified using 1, 2 and 10 Tm calibration beads (Becton Dickinson Immunocytometry Systems, Inc., San Jose, Calif. and Flow Cytometry Systems, Research Triangle Park, N.C.). Twenty-thousand events were collected in list mode with all light-scatter and fluorescence parameters in logarithmic mode. Platelets were gated on the basis of lightscatter and CD42a expression. Activated platelets were defined as the percentage of CD42a positive events coexpressing the activated conformation of GPIIb-IIIa or P-selectin. Platelet microparticles were defined as the percentage of CD42a positive events less than 2 µm in size.

One blood sample drawn at each of the three study time points was analyzed within four hours using a platelet function analyzer (PFA-100™, Dade Behring International, Miami, Fla.) according to the manufacturer's directions. The PFA-100™ is designed to measure collagen-ADP-and collagen-epinephrine-stimulated platelet function under shear conditions simulating those that exist in a small blood vessel (Mammen et al, "PFA-100 System: A New Method For Assessment Of Platelet Disfunction". Sem. Thromb. Hemostas. 24:195–202, 1998; Fressinaud et al, "Screening for Von Willebrand Disease with a New Analyzer using High Shear Stress: a Study of 60 Cases", Blood 91:1325–31, 1998). Function was measured as a closure time in seconds, which is defined as the time required for blood to occlude an aperture in the test cartridge membrane.

Data from each treatment or control group were analyzed for differences using Friedman's repeated measures ANOVA on ranks (SigmaStat for Windows, SPSS, Richmond, Calif.). Student-Newman-Keuls multiple comparison method was used to identify differences between baseline and 2 and 6 hours post-consumption results. P values less than 0.05 were considered statistically significant.

Cocoa consumption suppressed unstimulated (P=0.035, FIG. 21A) and ex vivo epinephrine-induced (P=0.008, FIG. 21B) activated GPIIb-IIIa expression at 2 and 6 hours after ingestion. The median percentages of platelets expressing activated GPIIb-IIIa without stimulation were 0.9, 0.5 and 0.3% and in response to epinephrine were 9.6, 6.8 and 3.3% at times zero, 2 and 6 hours, respectively, post consumption. In contrast, there was an increase in epinephrine-stimulated activated GPIIb-IIIa expression in the control group that drank the caffeine beverage (P=0.048, median=5.3, 6.5 and 7.5% at times zero, 2 and 6 hours post consumption). There was no change in the control group that drank water.

The cocoa decreased 20 μM ADP-induced activated GPIIb-IIIa expression on platelets 2 and 6 hours after consumption (P<0.001, FIG. 21C, median=58.5, 44.2 and 38.8% at times zero, 2 and 6 hours post consumption, respectively). The trend suggested decreased activated GPIIb-IIIa expression on platelets after cocoa consumption when activation was induced by 100 pm ADP (P=0.067, median=76.5, 68.7 and 57.6% at times zero, 2 and 6 hours post consumption, respectively). There was no change in ADP-induced activated GPIIb-IIIa expression in groups consuming the caffeine beverage and water controls.

A non-significant trend toward decreased P-selectin expression was observed after cocoa consumption (P=0.053, FIG. 22A). Cocoa consumption decreased 20 μM ADP-induced P-selectin expression 2 and 6 hours after consumption (P=0.007, FIG. 22C) and 100 μM ADP-induced P-selectin were 56.1, 54.7 and 41.7% at time zero, 2 and 6 hours post consumption, respectively.

There was no evidence of platelet stimulation or inhibition in the control groups that consumed the caffeine-containing beverage or water.

The number of platelet microparticles detected by flow cytometry after consumption of the cocoa beverage was decreased from baseline at 2 hours and was further decreased at 6 hours (see Table 6). In contrast, the number of platelet microparticles was increased at 2 and 6 hours after consumption of water and at 6 hours after consumption of the caffeine-containing beverage. Platelet microparticles are haemostatically active, phospholipid rich microvesicles that are formed during physiologic platelet activation.

Six hours following consumption of the cocoa beverage, collagen-epinephrine-induced closure time was prolonged (see Table 7). This indicates delayed platelet-related primary haemostasis with cocoa consumption. A trend toward prolonged closure time was observed after collagen-ADP-induction (p=0.097); closure time was not changed in the caffeine control group.

The results showed that consumption of the chocolate beverage modified platelet function in humans. First, platelet activation measured by platelet activation marker expression in response to weak agonists in vitro was decreased following cocoa consumption. Second, platelet microparticle formation was decreased following cocoa consumption. And third, the cocoa consumption caused an aspirin-like effect on platelet function as measured by platelet-related primary haemostasis. The fact that the caffeine beverage control caused an increase in epinephrine-induced activated GPIIb-IIIa expression and microparticle formation would imply that the cocoa procyanidins present in the cocoa beverage are responsible for the inhibition of platelet activation and function.

TABLE 6

MICROPARTICLE FORMATION AFTER CONSUMPTION OF A COCOA BEVERAGE.¯

| TIME | WATER | CAFFEINE BEVERAGE | COCOA BEVERAGE |
|---|---|---|---|
| BEFORE CONSUMPTION | 0.7 (0.3–1.2) | 1.0 (0.6–1.8) | 1.9 (1.0–5.0) |
| 2 H POST CONSUMPTION | 1.2 (0.7–1.6)* | 1.1 (0.6–2.0) | 1.0 (0.7–1.4)* |
| 6 H POST CONSUMPTION | 1.3 (0.8–2.1)* | 1.5 (1.2–2.3)* | 0.6 (0.4–1.1)* |

¯Percentage microparticles of total CD42 positive events. Values denote median (range), n = 10 per group.
*Significantly different from "Before Consumption" (P < 0.05).
Friedman's Repeated Measure ANOVA on ranks, followed by Student-Newman-Keuls multiple comparison method.

TABLE 7

PLATELET FUNCTION ANALYSIS.=

| | COLLAGEN-EPINEPHRINE | | COLLAGEN-ADP | |
|---|---|---|---|---|
| TIME | COCOA BEVERAGE | CAFFEINE BEVERAGE | COCOA BEVERAGE | CAFFEINE BEVERAGE |
| BEFORE CONSUMPTION | 125 (61–80) | 104 (61–180) | 83 (60–133) | 77 (52–95) |
| 2 H POST CONSUMPTION | 135 (82–194) | 113 (81–141) | 96 (65–132) | 78 (58–99) |
| 6 H POST CONSUMPTION | 164 (101–262)* | 114 (79–143) | 94 (66–116) | 82 (67–114) |

=Primary platelet-related hemostasis closure time in seconds. Values denote median (range), n = 10 per group.
*Significantly different from "Before Consumption" (P < 0.05).
Friedman's Repeated Measure ANOVA on ranks, followed by Student-Newman-Keuls multiple comparison method.

Example 15

Tablet Formulations

A tablet formulation was prepared using high cocoa procyanidin cocoa solids obtained by methods described above, hereby incorporated herein by reference. Briefly, this edible material is prepared by a process which enhances the natural occurrence of the cocoa procyanidins in contrast to their levels found in traditionally processed cocoa, such that the ratio of the initial amount of the cocoa procyanidins found in the unprocessed bean to that obtained after processing is less than or equal to 2. For simplicity, this cocoa solids material is designated herein as CP-cocoa solids. The inventive compound or compounds, e.g., in isolated and/or purified form may be used in tablets as described in this Example, instead of or in combination with CP-cocoa solids.

A tablet formula comprises the following (percentages expressed as weight percent):

| | |
|---|---|
| CP-cocoa solids | 24.0% |
| 4-Fold Natural vanilla extract (Bush Boake Allen) | 1.5% |
| Magnesium stearate (dry lubricant) (AerChem, Inc.) | 0.5% |
| Dipac tabletting sugar (Amstar Sugar Corp.) | 37.0% |
| Xylitol (American Xyrofin, Inc.) | 37.0% |
| | 100.0% |

The CP-cocoa solids and vanilla extract are blended together in a food processor for 2 minutes. The sugars and magnesium stearate are gently mixed together, followed by blending in the CP-cocoa solids/vanilla mix. This material is run through a Manesty Tablet Press (B3B) at maximum pressure and compaction to produce round tablets (15 mm×5 mm) weighing 1.5–1.8 gram. Another tablet of the above mentioned formula was prepared with a commercially available low fat natural cocoa powder (11% fat) instead of the CP-cocoa solids (11% fat). Both tablet formulas produced products having acceptable flavor characteristics and texture attributes.

An analysis of the two tablet formulas was performed using the procedures described in Example 4. In this case, the analysis focused on the concentration of the pentamer and the total level of monomers and cocoa procyanidins where n is 2 to 12 which are reported below.

| Tablet sample | pentamer (Tg/g) | total (Tg/g) | pentamer (Tg/ 1.8 g serving) | total (Tg/ 1.8 g serving) |
|---|---|---|---|---|
| tablet with CP-cocoa solids | 239 | 8,277 | 430 | 14,989 |
| tablet with commercial low fat cocoa powder | ND | 868 | ND | 1563 |

ND = not detected

The data clearly showed a higher level of pentamer and total level of cocoa procyanidins in the CP-cocoa solids tablet than in the other tablet formula. Thus, tablet formulas prepared with CP-cocoa solids are an ideal delivery vehicle for the oral administration of cocoa procyanidins, for pharmaceutical, supplement and food applications.

The skilled artisan in this area can readily prepare other tablet formulas covering a wide range of flavors, colors, excipients, vitamins, minerals, OTC medicaments, sugar fillers, UV protectants (e.g., titanium dioxide, colorants, etc.), binders, hydrogels, and the like except for polyvinyl pyrrolidone which would irreversibly bind the cocoa procyanidins or combination of compounds. The amount of sugar fillers may be adjusted to manipulate the dosages of the cocoa procyanidins or combination of compounds.

Many apparent variations of the above are self-evident and possible without departing from the spirit and scope of the example.

Example 16

Capsule Formulations

A variation of Example 15 for the oral delivery of the cocoa procyanidins is made with push-fit capsules made of gelatin, as well as soft sealed capsules made of gelatin and a plasticizer such as glycerol. The push-fit capsules contain the compound of the invention or combination of compounds or CP-cocoa solids as described in Example 15 in the form of a powder which can be optionally mixed with fillers such as lactose or sucrose to manipulate the dosages of the cocoa procyanidins. In soft capsules, the compound of the invention or combination of compounds or CP-cocoa solids are suspended in a suitable liquid such as fatty oils or cocoa butter or combinations therein. Since an inventive compound or compounds may be light-sensitive, e.g., sensitive to UV, a capsule can contain UV protectants such as titanium dioxide or suitable colors to protect against UV. The capsules can also contain fillers such as those mentioned in the previous Example.

Many apparent variations of the above are self-evident and possible to one skilled in the art without departing from the spirit and scope of the example.

Example 17

Standard of Identity (SOI) and Non-Standard of Identity (non-SOI) Dark and Milk Chocolate Formulations Formulations of the cocoa procyanidins or combination of compounds derived by methods embodied in the invention can be prepared into SOI and non-SOI dark and milk chocolates as a delivery vehicle for human and veterinary applications. Reference is made to copending U.S. application Ser. No. 08/709,406, filed Sep. 6, 1996, hereby incorporated herein by reference. U.S. Ser. No. 08/709,406 relates to a method of producing cocoa butter and/or cocoa solids having conserved levels of the cocoa procyanidins from cocoa beans using a unique combination of processing steps. Briefly, the edible cocoa solids obtained by this process conserves the natural occurrence of the cocoa procyanidins in contrast to their levels found in traditionally processed cocoa, such that the ratio of the initial amount of the cocoa procyanidins found in the unprocessed bean to that obtained after processing is less than or equal to 2. For simplicity, this cocoa solids material is designated herein as CP-cocoa solids. The CP-cocoa solids are used as a powder or liquor to prepare SOI and non-SOI chocolates, beverages, snacks, baked goods, and as an ingredient for culinary applications.

The term "SOI chocolate" as used herein shall mean any chocolate used in food in the United States that is subject to a Standard of Identity established by the U.S. Food and Drug Administration under the Federal Food, Drug and Cosmetic Act. The U.S. definitions and standards for various types of chocolate are well established. The term "non-SOI chocolate" as used herein shall mean any nonstandardized chocolates which have compositions which fall outside the specified ranges of the standardized chocolates.

Examples of nonstandardized chocolates result when the cocoa butter or milk fat are replaced partially or completely; or when the nutrative carbohydrate sweetener is replaced partially or completely; or flavors imitating milk, butter, cocoa powder, or chocolate are added or other additions or deletions in the formula are made outside the U.S. FDA Standards of Identity for chocolate or combinations thereof.

As a confection, chocolate can take the form of solid pieces of chocolate, such as bars or novelty shapes, and can also be incorporated as a component of other, more complex confections where chocolate is optionally combined with any Flavor & Extract Manufacturers Association (FEMA) material, natural juices, spices, herbs and extracts categorized as natural-flavoring substances; nature-identical substances; and artificial flavoring substances as defined by FEMA GRAS lists, FEMA and FDA lists, Council of Europe (CoE) lists, International Organization of the Flavor Industry (IOFI) adopted by the FAO/WHO Food Standard Programme, Codex Alimentarius, and Food Chemicals Codex and generally coats other foods such as caramel, nougat, fruit pieces, nuts, wafers or the like. These foods are characterized as microbiologically shelf-stable at 65–85□F under normal atmospheric conditions. Other complex confections result from surrounding with chocolate soft inclusions such as cordial cherries or peanut butter. Other complex confections result from coating ice cream or other frozen or refrigerated desserts with chocolate. Generally, chocolate used to coat or surround foods must be more fluid than chocolates used for plain chocolate solid bars or novelty shapes.

Additionally, chocolate can also be a low fat chocolate comprising a fat and nonfat solids, having nutrative carbohydrate sweetener(s), and an edible emulsifier. As to low fat chocolate, reference is made to U.S. Pat. Nos. 4,810,516, 4,701,337, 5,464,649, 5,474,795, and WO 96/19923.

Dark chocolates derive their dark color from the amount of chocolate liquor, or alkalized liquor or cocoa solids or alkalized cocoa solids used in any given formulation. However, the use of alkalized cocoa solids or liquor would not be used in the dark chocolate formulations in the invention.

Examples of formulations of SOI and non-SOI dark and milk chocolates are listed in Tables 8 and 9. In these formulations, the amount of the cocoa procyanidins present in CP-cocoa solids was compared to the cocoa procyanidins present in commercially available cocoa solids.

The following describes the processing steps used in preparing these chocolate formulations.

Process for Non-SOI Dark Chocolate

1. Keep all mixers and refiners covered throughout process to avoid light.
2. Batch all the ingredients excluding 40% of the free fat (cocoa butter and anhy. milk fat) maintaining temperature between 30–35° C.
3. Refine to 20 microns.
4. Dry conche for 1 hour at 35° C.
5. Add full lecithin and 10% cocoa butter at the beginning of the wet conche cycle; wet conche for 1 hour.
6. Add all remaining fat, standardize if necessary and mix for 1 hour at 35° C.
7. Temper, mould and package chocolate.

Process for SOI Dark Chocolate

1. Batch all ingredients excluding milk fat at a temperature of 60° C.
2. Refine to 20 microns.
3. Dry conche for 3.5 hours at 60° C.
4. Add lecithin and milk fat and wet conche for 1 hour at 60° C.
5. Standardize if necessary and mix for 1 hour at 35° C.
6. Temper, mould and package chocolate.

Process for non-SOI Milk Chocolate

1. Keep all mixers and refiners covered throughout process to avoid light.
2. Batch sugar, whole milk powder, malted milk powder, and 66% of the cocoa butter, conche for 2 hours at 75° C.
3. Cool batch to 35° C. and add cocoa powder, ethyl vanillin, chocolate liquor and 21% of cocoa butter, mix 20 minutes at 35° C.
4. Refine to 20 microns.
5. Add remainder of cocoa butter, dry conche for 1.5 hour at 35° C.
6. Add anhy. milk fat and lecithin, wet conche for 1 hour at 35° C.
7. Standardize, temper, mould and package the chocolate.

Process for SOI Milk Chocolate

1. Batch all ingredients excluding 65% of cocoa butter and milk fat at a temperature of 60° C.
2. Refine to 20 microns.
3. Dry conche for 3.5 hours at 60° C.
4. Add lecithin, 10% of cocoa butter and anhy. milk fat; wet conche for 1 hour at 60° C.
5. Add remaining cocoa butter, standardize if necessary and mix for 1 hour at 35° C.
6. Temper, mould and package the chocolate.

The CP-cocoa solids and commercial chocolate liquors used in the formulations were analyzed for the pentamer and total level of monomers and cocoa procyanidins where n is 2 to 12 prior to incorporation in the formulations. These values were then used to calculate the expected levels in each chocolate formula as shown in Tables 8 and 9. In the cases for the non-SOI dark chocolate and non-SOI milk chocolate, their products were similarly analyzed for the pentamer, and the total level of monomers and the cocoa procyanidins where n is 2 to 12. The results appear in Tables 8 and 9.

The results from these formulation examples indicated that SOI and non-SOI dark and milk chocolates formulated with CP-cocoa solids contained approximately 6.5 times more expected pentamer, and 3.5 times more expected total levels in the SOI and non-SOI dark chocolates; and approximately 4.5; 7.0 times more expected pentamer and 2.5; 3.5 times more expected total levels in the SOI and non-SOI milk chocolates, respectively.

Analyses of some of the chocolate products were not performed since the difference between the expected levels of the cocoa procyanidins present in finished chocolates prepared with CP-cocoa solids were dramatically higher than those formulas prepared with commercially available cocoa solids. However, the effects of processing was evaluated in the non-SOI dark and milk chocolate products. As shown in the tables, a 25–50% loss of the pentamer occurred, while slight differences in total levels were observed. Without wishing to be bound by any theory, it is believed that these losses are due to heat and/or low chain fatty acids from the milk ingredient (e.g. acetic acid, propionic acid and butyric acid) which can hydrolyze the oligomers (e.g. a trimer can hydrolyze to a monomer and dimer). Alternatively, time consuming processing steps can allow for oxidation or irreversible binding of the cocoa procyanidins to protein sources within the formula. Thus, the invention comprehends altering methods of chocolate formulation and processing to address these effects to prevent or minimize these losses.

The skilled artisan will recognize many variations in these examples to cover a wide range of formulas, ingredients, processing, and mixtures to rationally adjust the naturally occurring levels of the cocoa procyanidins for a variety of chocolate applications.

TABLE 8

Dark Chocolate Formulas Prepared with non-Alkalized Cocoa Ingredients

| Non-SOI Dark Chocolate Using CP-cocoa solids Formulation: | SOI Dark Chocolate Using CP-Cocoa Solids Formulation: | SOI Dark Chocolate Using Commercial Cocoa Solids Formulation |
|---|---|---|
| 41.49% Sugar | 41.49% sugar | 41.49% sugar |
| 3% whole milk powder | 3% whole milk powder | 3% whole milk powder |
| 26% CP-cocoa solids | 52.65% CP-liquor | 52.65% com. liquor |
| 4.5% com. liquor | 2.35% anhy. milk fat | 2.35% anhy. milk fat |
| 21.75% cocoa butter | 0.01% vanillin | 0.01% vanillin |
| 2.75% anhy. milk fat | 0.5% lecithin | 0.5% lecithin |
| 0.01% vanillin | | |
| 0.5% lecithin | | |
| Total fat: 31% | Total fat: 31% | Total fat: 31% |
| Particle size: 20 microns | Particle size: 20 microns | Particle size: 20 microns |

Expected Levels of pentamer and total oligomeric procyanidins (monomers and n=2–12; units of μg/g)

| Pentamer: 1205 | Pentamer: 1300 | Particle size: 20 microns |
|---|---|---|
| Total: 13748 | Total: 14646 | Total: 3948 |

Actual Levels of pentamer and total oligomeric procyanidins (monomers and n=2–12; units of μg/g)

| Pentamer: 561 | Not performed | Not performed |
|---|---|---|
| Total: 14097 | | |

TABLE 9

Milk Chocolate Formulas Prepared with non-Alkalized Cocoa Ingredients

| Non-SOI Dark Chocolate Using CP-cocoa solids Formulation: | SOI Dark Chocolate Using CP-Cocoa Solids Formulation: | SOI Milk Chocolate Using Commercial Cocoa Solids Formulation |
|---|---|---|
| 46.9965% Sugar | 46.9965% Sugar | 46.9965% Sugar |
| 15.5% whole milk powder | 15.5% whole milk powder | 15.5% whole milk powder |
| 4.5% CP-cocoa solids | powder | 13.9% com. liquor |
| 5.5% com.liquor | 13.9% CP-liquor | 1.60% anhy. milk fat |
| 21.4% cocoa butter | 1.6% anhy. milk fat | 0.0035% vanillin |
| 1.6% anhy. milk fat | 0.0035% vanillin | 0.5% Lecithin |
| 0.035% vanillin | 0.5% lecithin | 17.5% cocoa butter |
| 0.5% lecithin | 17.5% cocoa butter | 4.0% malted milk powder |
| 4.0% malted milk powder | 4.0% malted powder | |
| Total fat: 31.75% | Total fat: 31.75% | Total fat: 31.75% |
| Particle size: 20 microns | Particle size: 20 microns | Particle size: 20 microns |

Expected Levels of pentamer and total oligomeric procyanidins (monomers and n=2–12; units of μg/g)

| Pentamer: 225 | Pentamer: 343 | Particle size: 49 |
|---|---|---|
| Total: 2734 | Total: 3867 | Total: 1042 |

Actual Levels of pentamer and total oligomeric procyanidins (monomers and n=2–12; units of μg/g)

| Pentamer: 163 | Not performed | Not performed |
|---|---|---|
| Total: 2399 | | |

Example 18

The Effects of the Oral Consumption of Cocoa on the Inhibition of Vascular Endothelium Dependent Relaxation (EDR) by Cholesterol It has been shown that some plant extracts containing flavonoids induce EDR in vitro in rabbit aortas. We studied the effects of chronic oral administration of cocoa on EDR and its protective activity against the loss of EDR that occurs with cholesterol feeding. New Zealand White rabbits were fed 4 diets for 7 weeks: (1) chow, (2) chow+200 mg cocoa/day, (3) 2% cholesterol for 3 weeks followed by 4 weeks of chow, (4) 2% cholesterol for 3 weeks followed by 4 weeks of chow+200 mg cocoa/day. EDR was measured on aortic rings suspended in organ baths (20 ml). The rings were pre-contracted with norepinephrine (NE) ($10^{-5}$M). EDR to acetylcholine (Ach) and cocoa pentamer extract ($10^{-7}$–$10^{-5}$M) was measured as % relaxation to NE.

| Diet | Serum Cholesterol (3 wks) | EDR to Ach (%) | EDR to Pentamer extract (%) |
|---|---|---|---|
| 1(n = 6) | 52 ± mg/dL | 49.0 ± 5.1 | 46.5 ± 4.5 |
| 2(n = 5) | 30 ± 4 mg/dL | 44.4 ± 5.1 | 44.5 ± 3.6 |
| 3(n = 9) | 1377 ± 218 mg/dL | 16.1 ± 5.0(n = 6)* | 25.5 ± 9.7(n = 3) |
| 4(n = 5) | 1084 ± 266 mg/dL | 42.4 ± 11.3 | 49.5 ± 5.7 |

*significantly different others in the column

These results would indicate that oral administration of cocoa powder protects against the loss of EDR in cholesterol fed rabbits.

What is claimed is:

1. A method of anti-platelet therapy or prophylaxis comprising administering to a subject in need thereof a composition comprising an effective amount of a procyanidin oligomer comprising from 2 to 18 monomeric units of the following formula:

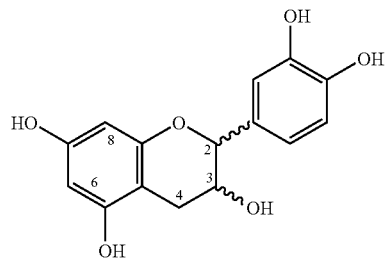

or a derivative thereof;
wherein the monomeric units are connected via interflavan linkages 4→6 and/or 4→8, and the subject is a human or a veterinary animal.

2. The method of claim 1, wherein the derivative is a gallated procyanidin oligomer.

3. The method of claim 1, wherein the procyanidin oligomer comprises from 3 to 12 monomeric units.

4. The method of claim 1, wherein the procyanidin oligomer comprises from 2 to 5 monomeric units.

5. The method of claim 1, wherein the procyanidin oligomer comprises 2 monomeric units.

6. A method of anti-platelet therapy or prophylaxis comprising administering to a subject in need thereof a composition comprising an effective amount of a procyanidin oligomer having the formula:

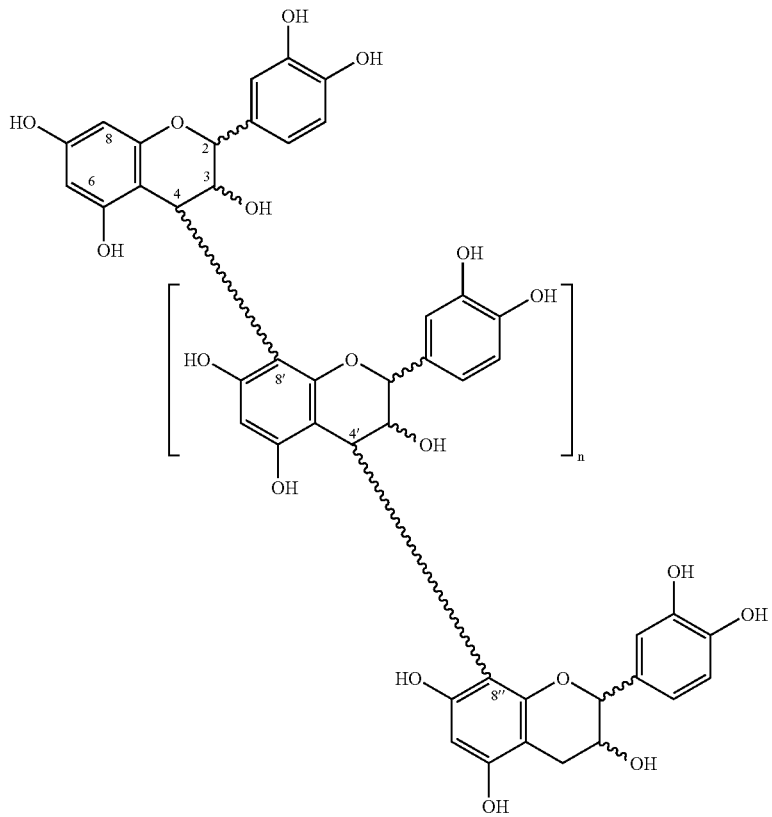

and n is 0 to 16.

7. A method of anti-platelet therapy or prophylaxis comprising administering to a subject in need thereof a composition comprising an effective amount of a procyanidin oligomer having the formula:

[chemical structure]

wherein A and B are independently oligomers having 1 to 15 monomeric units, and the total number of monomeric units in the procyanidin oligomer is 3 to 18.

8. The method of claim 1, wherein the subject is a human.

9. The method of claim 2, wherein the subject is a human.

10. The method of claim 3, wherein the subject is a human.

11. The method of claim 4, wherein the subject is a human.

12. The method of claim 5, wherein the subject is a human.

13. The method of claim 6, wherein the subject is a human.

14. The method of claim 7, wherein the subject is a human.

15. The method of claim 8, wherein the human suffers from atherosclerosis.

16. The method of claim 9, wherein the human suffers from atherosclerosis.

17. The method of claim 10, wherein the human suffers from atherosclerosis.

18. The method of claim 11, wherein the human suffers from atherosclerosis.

19. The method of claim 12, wherein the human suffers from atherosclerosis.

20. The method of claim 13, wherein the human suffers from atherosclerosis.

21. The method of claim 14, wherein the human suffers from atherosclerosis.

22. The method of claim 8, wherein the human is at risk of atherosclerosis.

23. The method of claim 9, wherein the human is at risk of atherosclerosis.

24. The method of claim 10, wherein the human is at risk of atherosclerosis.

25. The method of claim 11, wherein the human is at risk of atherosclerosis.

26. The method of claim 12, wherein the human is at risk of atherosclerosis.

27. The method of claim 13, wherein the human is at risk of atherosclerosis.

28. The method of claim 14, wherein the human is at risk of atherosclerosis.

29. The method of claim 1, wherein the composition is a pharmaceutical composition.

30. The method of claim 1, wherein the composition is a food composition.

31. The method of claim 1, wherein the composition is a dietary supplement composition.

32. The method of claim 3, wherein the composition is a pharmaceutical composition.

33. The method of claim 3, wherein the composition is a food composition.

34. The method of claim 3, wherein the composition is a dietary supplement composition.

35. The method of claim 4, wherein the composition is a pharmaceutical composition.

36. The method of claim 4, wherein the composition is a food composition.

37. The method of claim 4, wherein the composition is a dietary supplement composition.

38. The method of claim 5, wherein the composition is a pharmaceutical composition.

39. The method of claim 5, wherein the composition is a food composition.

40. The method of claim 5, wherein the composition is a dietary supplement composition.

41. The method of claim 6, wherein the composition is a pharmaceutical composition.

42. The method of claim 6, wherein the composition is a food composition.

43. The method of claim 6, wherein the composition is a dietary supplement composition.

44. The method of claim 7, wherein the composition is a pharmaceutical composition.

45. The method of claim 7, wherein the composition is a food composition.

46. The method of claim 7, wherein the composition is a dietary supplement composition.

47. The method of claim 1, wherein the derivative is a glycosylated procyanidin oligomer.

* * * * *